US011641858B2

(12) United States Patent
Urch et al.

(10) Patent No.: US 11,641,858 B2
(45) Date of Patent: *May 9, 2023

(54) AGRICULTURAL CHEMICALS

(71) Applicant: Redag Crop Protection Ltd, Wigan (GB)

(72) Inventors: Christopher John Urch, Wigan (GB); Roger John Butlin, Wigan (GB); Rebecca Kathryn Booth, Wigan (GB); Stephania Christou, Wigan (GB); Victor Ceban, Wigan (GB); Victoria Elizabeth Jackson, Wigan (GB)

(73) Assignee: REDAG CROP PROTECTION LTD., Manchester (GB)

( * ) Notice: Subject to any disclaimer, the term of this patent is extended or adjusted under 35 U.S.C. 154(b) by 677 days.

This patent is subject to a terminal disclaimer.

(21) Appl. No.: 16/090,702

(22) PCT Filed: Apr. 12, 2017

(86) PCT No.: PCT/GB2017/051026
§ 371 (c)(1),
(2) Date: Oct. 2, 2018

(87) PCT Pub. No.: WO2017/178819
PCT Pub. Date: Oct. 19, 2017

(65) Prior Publication Data
US 2020/0323209 A1 Oct. 15, 2020

(30) Foreign Application Priority Data

Apr. 13, 2016 (GB) ....................... 1606316
Jun. 14, 2016 (GB) ....................... 1610348
Nov. 16, 2016 (GB) ....................... 1619410

(51) Int. Cl.
*A01N 43/52* (2006.01)
*A01N 43/78* (2006.01)
*A01N 43/80* (2006.01)
*A01N 43/90* (2006.01)
*A01N 43/713* (2006.01)

(52) U.S. Cl.
CPC ........... *A01N 43/713* (2013.01); *A01N 43/52* (2013.01); *A01N 43/78* (2013.01); *A01N 43/80* (2013.01); *A01N 43/90* (2013.01)

(58) Field of Classification Search
CPC ........ A01N 43/40; A01N 43/48; A01N 43/52; A01N 43/713; A01N 43/90
USPC ................................ 504/244, 251, 252, 253
See application file for complete search history.

(56) References Cited

U.S. PATENT DOCUMENTS

| | | | | |
|---|---|---|---|---|
| 4,859,689 A | * | 8/1989 | Puritch | ................ A01N 43/40 514/358 |
| 2002/0049142 A1 | | 4/2002 | Mathews et al. | |
| 2003/0207926 A1 | | 11/2003 | Armstrong et al. | |
| 2004/0063937 A1 | | 4/2004 | Eberle et al. | |
| 2011/0294840 A1 | | 12/2011 | Ihara et al. | |
| 2014/0051575 A1 | | 2/2014 | Benting et al. | |

FOREIGN PATENT DOCUMENTS

| | | | | |
|---|---|---|---|---|
| CN | 104974136 A | | 10/2015 | |
| WO | WO-9957103 A1 | * | 11/1999 | .......... C07D 235/26 |
| WO | 200006566 A1 | | 2/2000 | |
| WO | 200155144 A1 | | 8/2001 | |
| WO | 2009077197 A1 | | 12/2008 | |
| WO | 2011015524 A2 | | 2/2011 | |
| WO | WO-2012136581 A1 | * | 10/2012 | .......... C07D 417/12 |
| WO | 2016055802 A2 | | 4/2016 | |

OTHER PUBLICATIONS

International Search Report and Written Opinion, for International Application No. PCT/GB2017/051026, dated Jun. 21, 2017, 15 pages.
State Intellectual Property Office of the People's Republic of China First Office Action for patent application No. 2017800233342, dated Jun. 3, 2020, 2 pages.
United Kingdom Search Report for international application No. GB1606316.6 dated Jan. 17, 2017 3 pages.

* cited by examiner

*Primary Examiner* — Alton N Pryor
(74) *Attorney, Agent, or Firm* — Morgan, Lewis & Bockius, LLP

(57) ABSTRACT

The present invention relates to compounds which are of use in the field of agriculture as fungicides.

21 Claims, No Drawings

AGRICULTURAL CHEMICALS

This application is the U.S. national stage application of International (PCT) Patent Application Serial No. PCT/GB2017/051026, filed Apr. 12, 2017, which claims the benefit of GB Application No. 1606316.6, filed Apr. 13, 2016, GB Application No. 1610348.3, filed Jun. 14, 2016, and GB Application No. 1619410.2, filed Nov. 16, 2016. The entire disclosure of each of these applications is hereby incorporated by reference.

The present invention relates to compounds which are of use in the field of agriculture as fungicides.

Given the global increase in demand for food, there is an international need for new treatments to reduce food crop losses to disease, insects and weeds. Over 40% of crops are lost before harvest, and 10% post harvest, worldwide. Losses have actually increased since the mid-1990s.

A new threat contributing to this is the emergence of chemical-resistant organisms, for example, glyphosate-resistant weeds in USA and strobilurin-resistant strains of *Septoria* fungal species.

Recent research also suggests that the geographical spread of many crop pests and diseases is increasing, possibly as a result of global warming.

WO2012/136581 and PCT/GB2015/052958 (WO2016/055802) provide a range of tetrazole containing compounds that have proved active as fungicides.

An aim of certain embodiments of the present invention is to provide pesticides (e.g. nematicides, acaricides, insecticides and fungicides) which have activity either non-selectively, i.e. broad spectrum activity, or which are active specifically against selective target organisms.

An aim of certain embodiments of the present invention is to provide compounds which are less persistent in the environment after use than prior art compounds. Alternatively or additionally the compounds of the present invention may be less prone to bioaccumulation once in the food chain than prior art compounds.

Another aim of certain embodiments of the invention is to provide compounds which are less harmful to humans than prior art compounds.

Alternatively or additionally, the compounds of the invention may be less harmful than prior art compounds to one or more of the following groups: amphibians, fish, mammals (including domesticated animals such as dogs, cats, cows, sheep, pigs, goats, etc.), reptiles, birds, and beneficial invertebrates (e.g. bees and other insects, or worms), beneficial nematodes, beneficial fungi and nitrogen-fixing bacteria.

Certain compounds of the invention may be as active or more active than prior art compounds. They may have activity against organisms which have developed a resistance to prior art compounds. However, certain embodiments of the present invention may also concern compounds which have a lower level of activity relative to prior art compounds. These lower activity compounds are still effective as fungicides but may have other advantages relative to existing compounds such as, for example, a reduced environmental impact.

Certain compounds of the invention may be more selective than the parent, i.e. they may have better, similar or even slightly lower activity than the parent against target species but have a significantly lower activity against non-target species (e.g. the crops which are being protected).

Certain embodiments of the invention provide compounds that achieve one or more of the above aims. The compounds may be active in their own right or may metabolise or react in aqueous media to yield an active compound.

SUMMARY OF THE INVENTION

In a first aspect of the invention is provided a compound of formula (I):

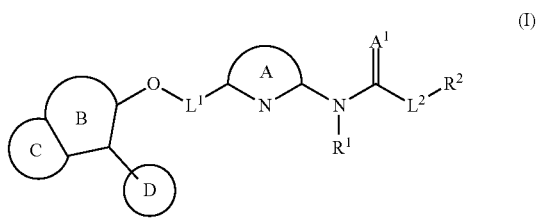

wherein Ring A is independently a 5- or 6-membered heteroaryl ring having a nitrogen in the position indicated, optionally further substituted with from 1 to 3 $R^3$ groups;

Ring B is independently a 5- or 6-membered heteroaryl ring, optionally further substituted with one or two $R^4$ groups;

Ring C is independently selected from a 5- or 6-membered heteroaryl ring and a benzene ring, optionally further substituted with from 1 to 4 $R^5$ groups;

Ring D is independently selected from 5- or 6-membered heteroaryl and phenyl, optionally further substituted with from 1 to 5 $R^6$ groups;

=$A^1$ is selected from =O and =S;

-$L^1$- is —$C_1$-$C_3$-alkylene-;

-$L^2$- is absent or is independently selected from —O—, —S— and —$NR^9$—;

$R^1$, $R^9$ and $R^{10}$ are each independently at each occurrence selected from H and $C_1$-$C_4$-alkyl;

$R^2$ is independently selected from: $C_1$-$C_6$-alkyl, $C_2$-$C_6$-alkenyl, $C_2$-$C_6$-alkynyl, $C_3$-$C_6$-cycloalkyl, $_{3-6}$-heterocycloalkyl, 5- or 6-membered heteroaryl, phenyl, —$CR^7R^7L^3R^8$, and —$C_1$-$C_3$-alkylene-$R^{2a}$; wherein $R^{2a}$ is independently selected from $C_3$-$C_6$-cycloalkyl, $_{3-6}$-heterocycloalkyl, 5- or 6-membered heteroaryl and phenyl;

-$L^3$- is independently selected from —O—, —S— and —$NR^9$—;

$R^3$, $R^4$, $R^5$ and $R^6$ are each independently at each occurrence selected from: halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl;

$R^7$ is independently at each occurrence selected from F, H and $C_1$-$C_4$-alkyl;

$R^8$ is independently selected from H, $C_1$-$C_4$-alkyl, $C_3$-$C_4$-alkenyl, $C_3$-$C_4$-alkynyl, $C_3$-$C_6$-cycloalkyl, $_{3-6}$-heterocycloalkyl, 5- or 6-membered heteroaryl, phenyl and —$C_1$-$C_3$-alkylene-$R^{8a}$; wherein $R^{8a}$ is independently selected from $C_3$-$C_6$-cycloalkyl, $_{3-6}$-heterocycloalkyl, 5- or 6-membered heteroaryl and phenyl;

$R^{11}$ is independently at each occurrence selected from H, $C_3$-$C_6$-cycloalkyl, $C_1$-$C_4$-alkyl, $C(O)$—$C_1$-$C_4$-alkyl and $S(O)_2$—$C_1$-$C_4$-alkyl;

wherein any $R^1$-$R^{11}$ group (including $R^{2a}$ and $R^{8a}$) comprises an alkyl, alkylene, haloalkyl, cycloalkyl, heterocycloalkyl, aryl (e.g. phenyl) or heteroaryl group may be optionally substituted, where chemically possible, by 1 to 5 substituents which are each independently selected at each occurrence from: oxo, =$NR^a$, =$NOR^a$, halo, nitro, cyano, $NR^aR^a$, $NR^aS(O)_2R^a$, $NR^aC(O)R^a$, $NR^aCONR^aR^a$, NR$^a$CO$_2$R$^a$, OR$^a$, SR$^a$, S(O)R$^a$, S(O)$_2$R$^a$, S(O)$_2$NR$^a$R$^a$, CO$_2$R$^a$ C(O)R$^a$, CONR$^a$R$^a$, unsubstituted C$_1$-C$_4$-alkyl, unsubstituted C$_2$-C$_4$-alkenyl, unsubstituted C$_2$-C$_4$-alkynyl and unsubstituted C$_1$-C$_4$-haloalkyl; wherein R$^a$ is independently at each occurrence selected from H, unsubstituted C$_1$-C$_4$ alkyl and unsubstituted C$_1$-C$_4$-haloalkyl;

or an agronomically acceptable salt or N-oxide thereof.

As illustrated in the embodiments below and, for the absence of doubt, where rings B and C contain at least one nitrogen, the nitrogen or the nitrogen atoms may be at any position in the ring. Thus it may be that the atom in ring B to which ring D is attached is carbon or nitrogen. Likewise, it may be that any atom that forms part of both ring B and ring C may be carbon or nitrogen.

In an embodiment, the compound of formula (I) is a compound of formula (II):

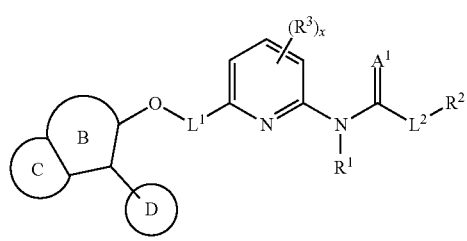

(II)

wherein Ring B, Ring C, Ring D, A$^1$, L$^1$, L$^2$, R$^1$, R$^2$ and R$^3$ are as described above for compounds of formula (I); and wherein x is an integer from 0 to 3. -L$^2$- may be absent. =A$^1$ may be =O.

In an embodiment, the compound of formula (I) is a compound of formula (III):

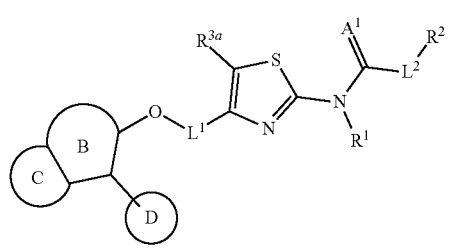

(III)

wherein Ring B, Ring C, Ring D, A$^1$, L$^1$, L$^2$, R$^1$ and R$^2$ are as described above for compounds of formula (I); and wherein R$^{3a}$ is selected from H and R$^3$. -L$^2$- may be absent. =A$^1$ may be =O.

In an embodiment, the compound of formula I is a compound of formula (IV):

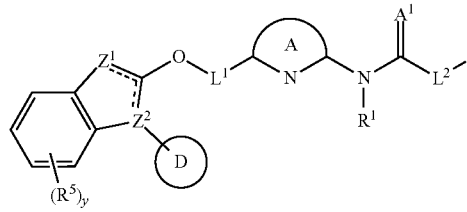

(IV)

wherein Ring A, Ring D, A$^1$, L$^1$, L$^2$, R$^1$, R$^2$ and R$^5$ are as described above for compounds of formula (I); and wherein Z$^1$ is selected from N, CR$^{4a}$ and NR$^{4b}$, Z$^2$ is selected from carbon and nitrogen; y is an integer from 0 to 4. For the absence of doubt, where Z$^2$ is nitrogen, the bond between Z$^2$ and the carbon between Z$^1$ and Z$^2$ is a single bond, the bond between Z$^1$ and the carbon between Z$^1$ and Z$^2$ is a double bond and Z$^1$ is selected from N and CR$^{4a}$. At least one of Z$^1$ and Z$^2$ is nitrogen, N or NR$^{4b}$. Likewise, where Z$^2$ is carbon, the bond between Z$^2$ and the carbon between Z$^1$ and Z$^2$ is a double bond, the bond between Z$^1$ and the carbon between Z$^1$ and Z$^2$ is a single bond and Z$^1$ is NR$^{4b}$. R$^{4a}$ is independently selected from: H, halo, nitro, cyano, NR$^{10}$R$^{11}$, NR$^{10}$S(O)$_2$R$^{10}$, NR$^{10}$C(O)R$^{10}$, NR$^{10}$CONR$^{10}$R$^{10}$, NR$^{10}$CO$_2$R$^{10}$, OR$^{10}$, SR$^{10}$, S(O)R$^{10}$, S(O)$_2$R$^{10}$, S(O)$_2$NR$^{10}$R$^{10}$, CO$_2$R$^{10}$, C(O)R$^{10}$, CONR$^{10}$R$^{10}$, C$_1$-C$_4$-alkyl, C$_2$-C$_4$-alkenyl, C$_2$-C$_4$-alkynyl, phenyl, C$_3$-C$_6$-cycloalkyl, $_{3-6}$-heterocycloalkyl, 5- or 6-membered heteroaryl and C$_1$-C$_4$-haloalkyl. R$^{4b}$ is independently selected from H, C$_1$-C$_4$-alkyl, C$_3$-C$_4$-alkenyl, C$_3$-C$_4$-alkynyl, phenyl, C$_3$-C$_6$-cycloalkyl, $_{3-6}$-heterocycloalkyl, 5- or 6-membered heteroaryl and C$_1$-C$_4$-haloalkyl. -L$^2$- may be absent. =A$^1$ may be =O.

In an embodiment, the compound of formula I is a compound of formula (IVa):

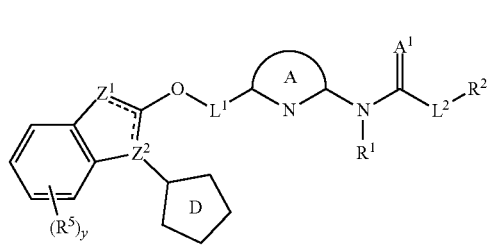

(IVa)

wherein Ring A, A$^1$, L$^1$, L$^2$, R$^1$, R$^2$ and R$^5$ are as described above for compounds of formula (I); and wherein Z$^1$ is selected from N, CR$^{4a}$ and NR$^{4b}$, Z$^2$ is selected from carbon and nitrogen; y is an integer from 0 to 4 and ring D is a tetrazole attached to a single R$^{6a}$ group. R$^{6a}$ is independently selected from H, C$_1$-C$_4$-alkyl, C$_3$-C$_4$-alkenyl, C$_3$-C$_4$-alkynyl, phenyl, C$_3$-C$_6$-cycloalkyl, $_{3-6}$-heterocycloalkyl, 5- or 6-membered heteroaryl and C$_1$-C$_4$-haloalkyl. -L$^2$- may be absent. =A$^1$ may be =O.

In an embodiment, the compound of formula I is a compound of formula (IVb):

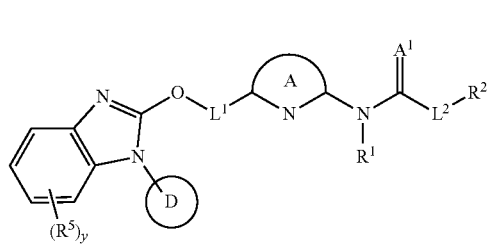

(IVb)

wherein Ring A, Ring D, A$^1$, L$^1$, L$^2$, R$^1$, R$^2$ and R$^5$ are as described above for compounds of formula (I); and wherein y is an integer from 0 to 4. -L$^2$- may be absent. =A$^1$ may be =O.

In an embodiment, the compound of formula (I) is a compound of formula (V):

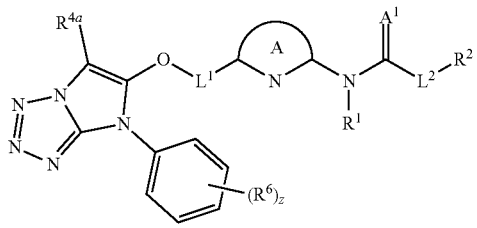

(V)

wherein Ring A, $A^1$, $L^1$, $L^2$, $R^1$, $R^2$ and $R^6$ are as described above for compounds of formula (I); and wherein $R^{4a}$ is as described above for formula (IV); and z is an integer from 0 to 5. $-L^2$ may be absent. $=A^1$ may be $=O$.

In an embodiment, the compound of formula (I) is a compound of formula (VI):

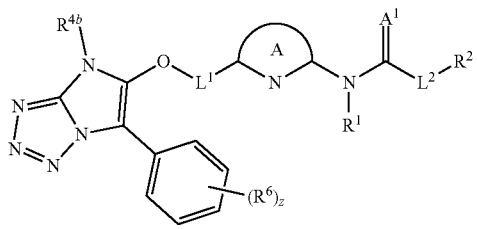

(VI)

wherein Ring A, $A^1$, $L^1$, $L^2$, $R^1$, $R^2$ and $R^6$ are as described above for compounds of formula (I); and wherein $R^{4b}$ is as described above for formula (IV); and z is as described above for formula (V). $-L^2$- may be absent. $=A^1$ may be $=O$.

In an embodiment, the compound of formula (I) is a compound of formula (VII):

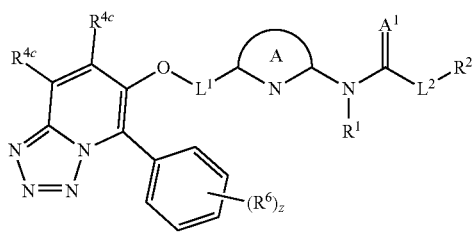

(VII)

wherein Ring A, $A^1$, $L^1$, $L^2$, $R^1$, $R^2$ and $R^6$ are as described above for compounds of formula (I); and wherein $R^{4c}$ is independently at each occurrence selected from: H, halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl; and z is an integer from 0 to 5. $-L^2$- may be absent. $=A^1$ may be $=O$.

In an embodiment, the compound of formula (I) is a compound of formula (VIII):

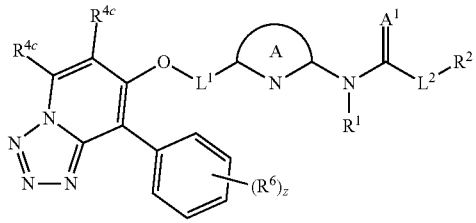

(VIII)

wherein Ring A, $A^1$, $L^1$, $L^2$, $R^1$, $R^2$ and $R^6$ are as described above for compounds of formula (I); and wherein $R^{4c}$ and z are as described above for formula (VII). $-L^2$- may be absent. $=A^1$ may be $=O$.

In an embodiment, the compound of formula I is a compound of formula (IX):

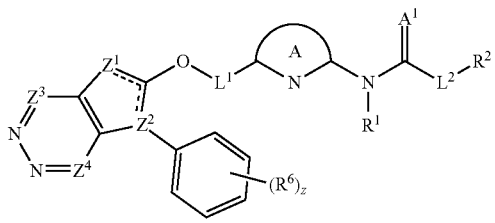

(IX)

wherein Ring A, $A^1$, $L^1$, $L^2$, $R^1$, $R^2$, and $R^6$ are as described above for compounds of formula (I); and wherein $Z^1$ and $Z^2$ are as described above for compounds of formula (IV); wherein a single one of $Z^3$ and $Z^4$ is N and the other of $Z^3$ and $Z^4$ is $CR^{5a}$; $R^{5a}$ is independently selected from: H, halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl; and z is an integer from 0 to 5. $-L^2$- may be absent. $=A^1$ may be $=O$.

The following embodiments apply to compounds of any of formulae (I)-(IX). These embodiments are independent and interchangeable. Any one embodiment may be combined with any other embodiment, where chemically allowed. In other words, any of the features described in the following embodiments may (where chemically allowable) be combined with the features described in one or more other embodiments. In particular, where a compound is exemplified or illustrated in this specification, any two or more of the embodiments listed below, expressed at any level of generality, which encompass that compound may be combined to provide a further embodiment which forms part of the present disclosure.

$=A^1$ may be $=S$. $=A^1$ may be $=O$.

Ring A may be a 6-membered heteroaryl group. Thus, ring A may be selected from pyridine, pyrimidine or pyrazine. In certain preferred examples, A is pyridine. Thus, the group

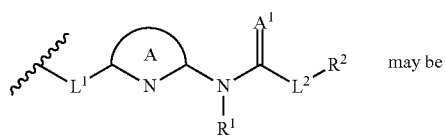 may be

-continued

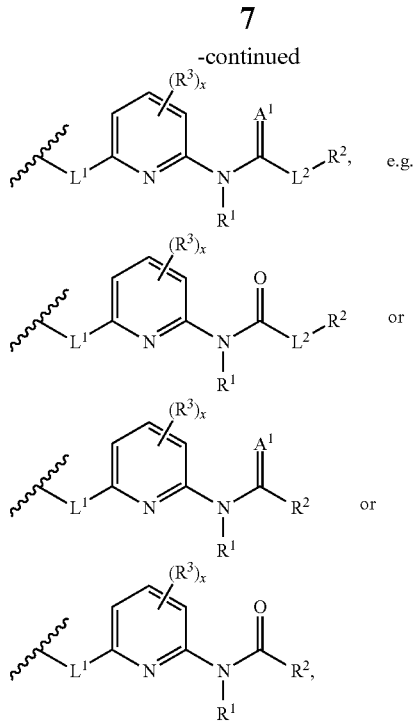

wherein x is an integer from 0 to 3.

$R^3$ is independently at each occurrence selected from: halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^3$ may be independently at each occurrence selected from halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl. $R^3$ may be independently at each occurrence selected from halo, cyano, $C_1$-$C_4$-alkyl and $C_1$-$C_4$-haloalkyl. $R^3$ may be independently at each occurrence selected from: halo, cyano, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

x may be an integer from 0 to 2. x may be an integer from 1 to 3, e.g. from 1 to 2. x may be 1. x may be 0. Thus, the group

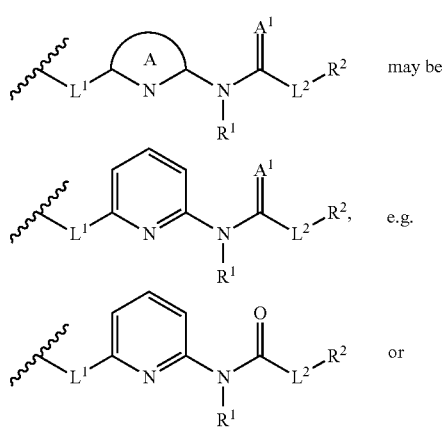

-continued

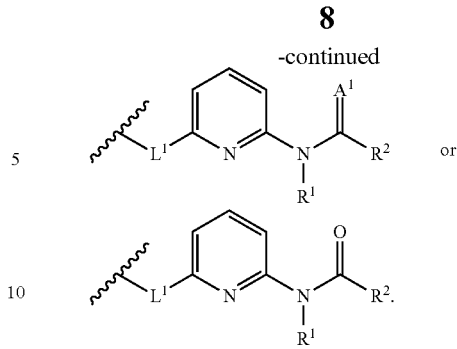

Alternatively, ring A may be a 5-membered heteroaryl group. Thus, A may be selected from oxazole, imidazole or thiazole. Ring A may be selected from oxazole and thiazole. In certain preferred examples, ring A is thiazole. Thus, the group

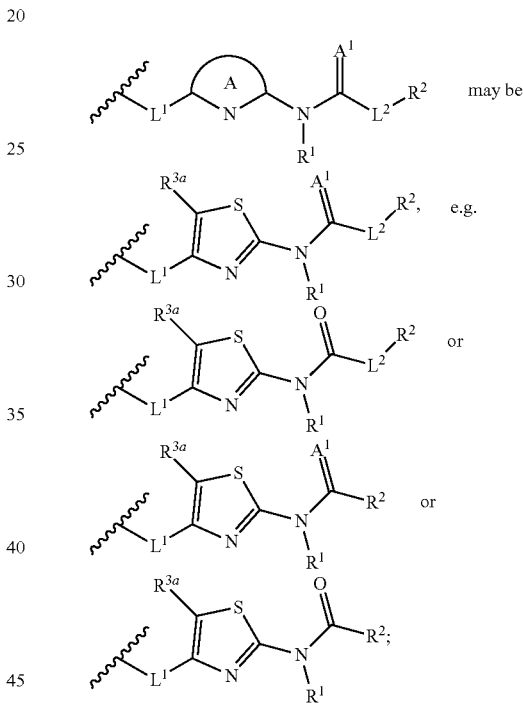

where $R^{3a}$ is independently selected from H and $R^3$.

$R^{3a}$ is thus independently selected from: H, halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^{3a}$ may be independently selected from H, halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl. $R^{3a}$ may be independently selected from: H, halo, cyano, $C_1$-$C_4$-alkyl and $C_1$-$C_4$-haloalkyl. $R^{3a}$ may be independently selected from: H, halo, cyano, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^{3a}$ may be $R^3$. $R^{3a}$ may thus be independently selected from: halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^{3a}$ may be independently selected from halo, nitro, cyanono, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl. $R^{3a}$ may be independently selected from: halo, cyano, $C_1$-$C_4$-alkyl and $C_1$-$C_4$-haloalkyl. $R^{3a}$ may be independently selected from: halo, cyano, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

$R^{3a}$ may be H. Thus, the group

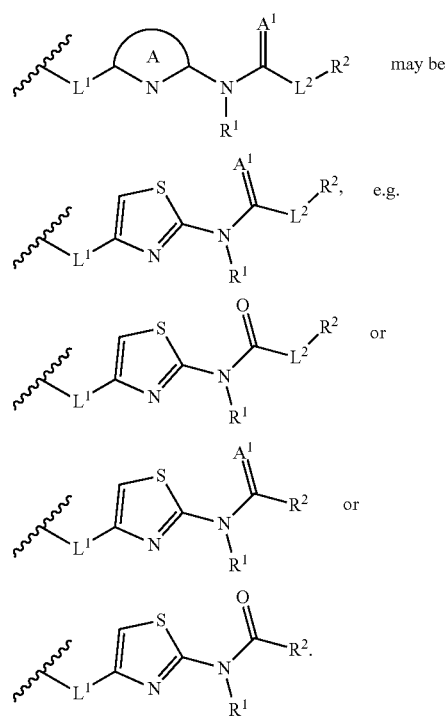

$R^1$ may be $C_1$-$C_4$-alkyl, e.g. Me or Et. Preferably, however, $R^1$ is H.

-$L^2$- may be absent. In these embodiments, $R^2$ may be independently selected from: $C_1$-$C_4$-alkyl, $C_2$-$C_4$-alkenyl, $C_2$-$C_4$-alkynyl, $C_3$-$C_6$-cycloalkyl, $_{3-6}$-heterocycloalkyl, 5- or 6-membered heteroaryl, phenyl, —$CR^7R^7L^3R^8$, and —$C_1$-$C_3$-alkylene-$R^{2a}$; wherein $R^{2a}$ is independently selected from $C_3$-$C_6$-cycloalkyl, $_{3-6}$-heterocycloalkyl, 5- or 6-membered heteroaryl and phenyl. $R^2$ may be independently selected from: $C_1$-$C_4$-alkyl, $C_2$-$C_4$-alkenyl, $C_2$-$C_4$-alkynyl, $C_3$-$C_6$-cycloalkyl, $_{3-6}$-heterocycloalkyl, 5- or 6-membered heteroaryl, phenyl and —$C_1$-$C_3$-alkylene-$R^{2a}$; wherein $R^{2a}$ is independently selected from $C_3$-$C_6$-cycloalkyl, $_{3-6}$-heterocycloalkyl, 5- or 6-membered heteroaryl and phenyl. $R^2$ may be independently selected from: $_{3-6}$-heterocycloalkyl, 5- or 6-membered heteroaryl and —$CR^7R^7L^3R^8$. $R^2$ is most preferably -$CR^7R^7L^3R^8$. $R^2$ may be $C_1$-$C_6$-alkyl. $R^2$ may be $C_1$-$C_4$-alkyl, e.g. Me or Et.

Illustrative -$L^2$-$R^2$ groups include:

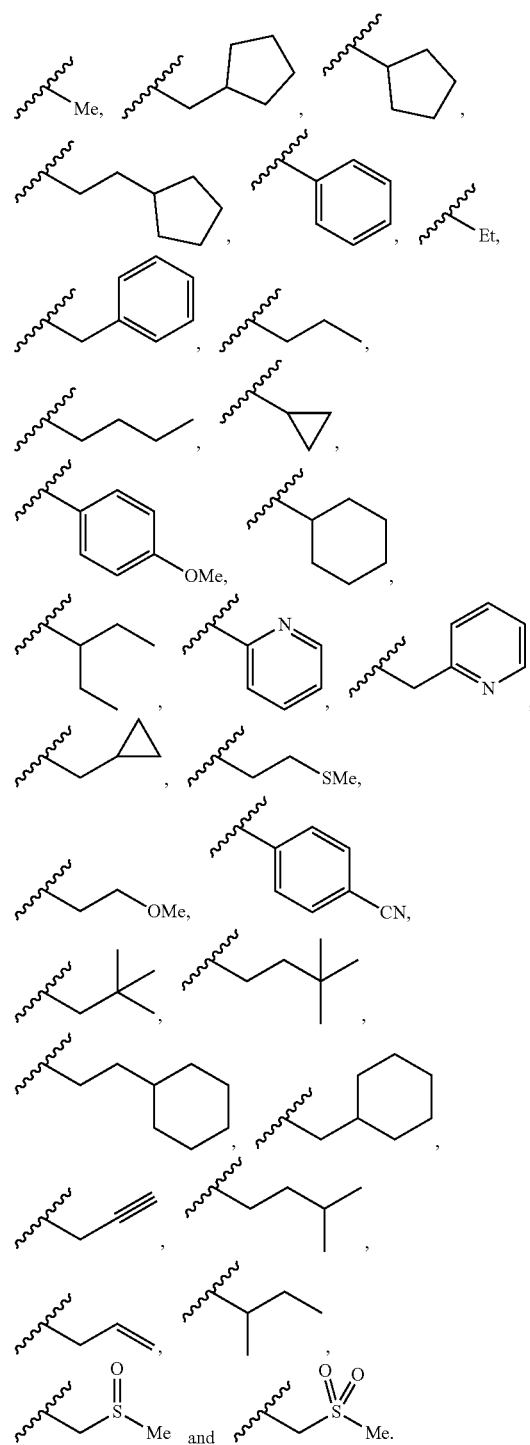

-$L^2$- may be independently selected from: —O—, —S— and —$NR^9$—. -$L^2$- may be —O—. In these embodiments, $R^2$ may be independently selected from $C_1$-$C_6$-alkyl, $C_3$-$C_6$-alkenyl, $C_3$-$C_6$-alkynyl, $C_3$-$C_6$-cycloalkyl, $_{3-6}$-heterocycloalkyl, 5- or 6-membered heteroaryl, phenyl and —$C_1$-$C_3$-alkylene-$R^{2a}$; wherein $R^{2a}$ is independently selected from $C_3$-$C_6$-cycloalkyl, $_{3-6}$-heterocycloalkyl, 5- or 6-membered heteroaryl and phenyl. $R^2$ may be $C_1$-$C_6$-alkyl. $R^2$ may be $C_3$-$C_6$-alkyl, e.g. $^tBu$, $^iPr$ or $^iBu$.

Illustrative -L²-R² groups include:

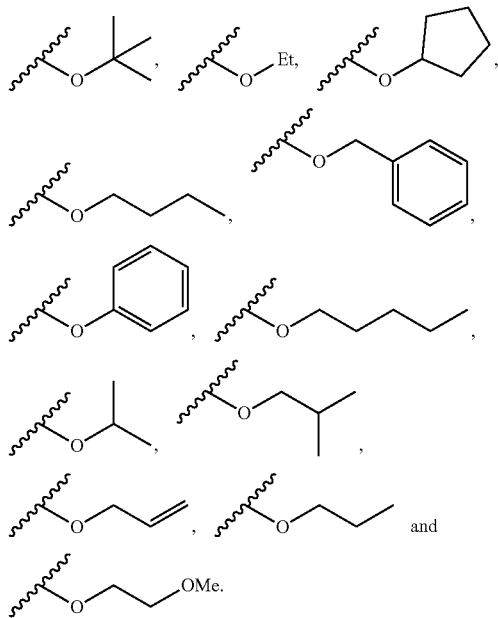

R² may be —CR⁷R⁷L³R⁸. It may be that -L²- is absent and R² is —CR⁷R⁷L³R⁸.

-L³- may be —NR⁹—, e.g. NH. -L³- may be —S—. -L³- is preferably —O—.

R⁷ is preferably at all occurrences independently selected from F, H and Me. R⁷ may at all occurrences be selected from F and H. R⁷ may at all occurrences be H. R⁷ may at all occurrences be F. R⁷ may at all occurrences be H.

R⁸ may be selected from $C_1$-$C_4$-alkyl, $C_3$-$C_4$-alkenyl, $C_3$-$C_4$-alkynyl, $C_3$-$C_6$-cycloalkyl, $_{3-6}$-heterocycloalkyl, 5- or 6-membered heteroaryl, phenyl and —$C_1$-$C_3$-alkylene-$R^{8a}$; wherein $R^{8a}$ is independently selected from $C_3$-$C_6$-cycloalkyl, $_{3-6}$-heterocycloalkyl, 5- or 6-membered heteroaryl and phenyl. R⁸ may be selected from $C_1$-$C_4$-alkyl, $C_3$-$C_4$-alkenyl, $C_3$-$C_4$-alkynyl, $C_3$-$C_6$-cycloalkyl, $_{3-6}$-heterocycloalkyl, 5- or 6-membered heteroaryl and phenyl. R⁸ may be selected from $C_3$-$C_7$ cycloalkyl, $_{3-6}$-heterocycloalkyl, phenyl and 5- or 6-membered heteroaryl. R⁸ may be selected from: H, $C_1$-$C_4$-alkyl, $C_3$-$C_4$-alkenyl, $C_3$-$C_4$-alkynyl, $C_3$-$C_6$-cycloalkyl and phenyl. R⁸ may be selected from: $C_1$-$C_4$-alkyl, $C_3$-$C_4$-alkenyl, $C_3$-$C_4$-alkynyl, $C_3$-$C_6$-cycloalkyl and phenyl. R⁸ may be selected from: $C_3$-$C_6$-cycloalkyl and phenyl. R⁸ may be unsubstituted. R⁸ may be $C_3$-$C_6$-cycloalkyl, e.g. unsubstituted $C_3$-$C_6$-cycloalkyl. R⁸ may be phenyl. Thus, R⁸ may be unsubstituted phenyl. R⁸ may be phenyl substituted with from 1 to 3 groups selected from halogen, $C_1$-$C_4$-alkyl, O—$C_1$-$C_4$-alkyl, cyano and $C_1$-$C_4$-haloalkyl. Where R⁸ is substituted, it may be that the substitutent or one of the substituents is situated at the 4-position of the phenyl ring.

R² may be CR⁷R⁷OR⁸, where R⁸ is independently selected from: H, $C_1$-$C_4$-alkyl, $C_3$-$C_4$-alkenyl, $C_3$-$C_4$-alkynyl, $C_3$-$C_6$-cycloalkyl, and phenyl. Said R⁸ groups may be unsubstituted. R² may be CR⁷R⁷OR⁸, where R⁸ is independently selected from: unsubstituted $C_3$-$C_6$-cycloalkyl and unsubstituted phenyl.

Illustrative -L²-R² groups include:

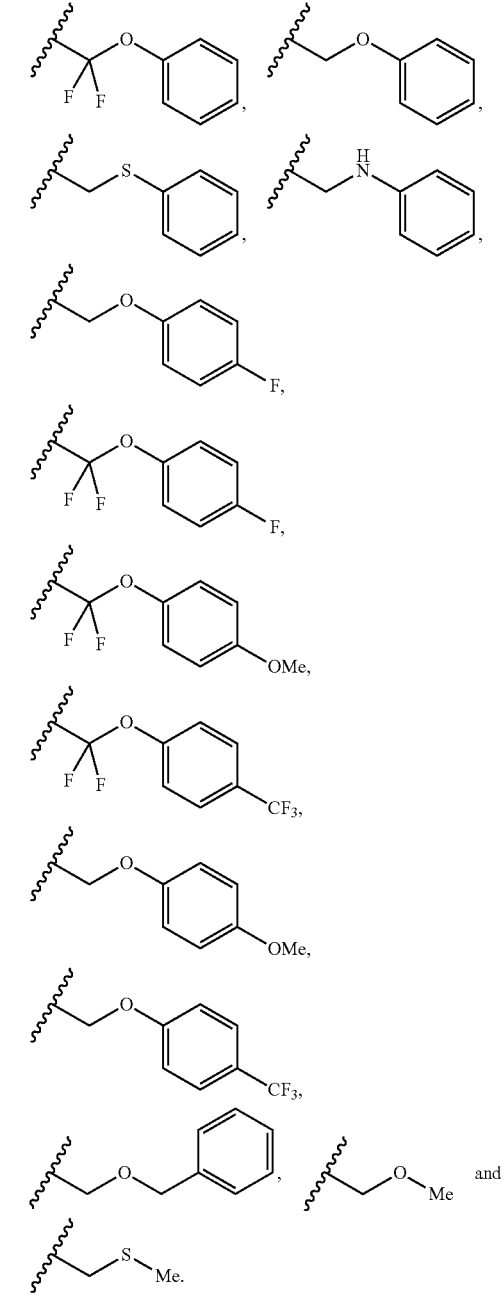

-L¹- may be $C_1$-$C_2$-alkylene. -L¹- may be —$C_1$-alkylene. -L¹- is preferably —CH₂—.

Ring D may be a 5- or 6-membered heteroaryl group. Ring D may be a 5- or 6-membered heteroaryl group having 1, 2, 3 or 4 nitrogen atoms in the ring. Ring D may be a 5-membered heteroaryl group having 1, 2, 3 or 4 nitrogen atoms in the ring. Ring D may be a 6-membered heteroaryl group having 1 or 2 nitrogen atoms in the ring.

Ring D may be substituted at a position adjacent to the point of connection of Ring D to the rest of the molecule with an R⁶ group. Ring D may be substituted at a position adjacent to the point of connection of Ring D to the rest of the molecule with an $R^{6b}$ group, wherein $R^{6b}$ is selected from $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. Ring D may be a 5- or 6-membered heteroaryl group having 1, 2, 3 or 4 nitrogen atoms in the ring, said heteroaryl group being substituted at a position adjacent to the point of connection of Ring D to the rest of the molecule with an $R^6$ group. Ring D may be a 5- or 6-membered heteroaryl group having 1, 2, 3 or 4 nitrogen atoms in the ring, said heteroaryl group being substituted at a position adjacent to the point of connection of Ring D to the rest of the molecule with an $R^{6b}$ group. Ring D may be a 5-membered heteroaryl group having 1, 2, 3 or 4 nitrogen atoms in the ring, said heteroaryl group being substituted at a position adjacent to the point of connection of Ring D to the rest of the molecule with an $R^6$ group. Ring D may be a 5-membered heteroaryl group having 1, 2, 3 or 4 nitrogen atoms in the ring, said heteroaryl group being substituted at a position adjacent to the point of connection of Ring D to the rest of the molecule with an $R^{6b}$ group. Ring D may be a 6-membered heteroaryl group having 1 or 2 nitrogen atoms in the ring, said heteroaryl group being substituted at a position ortho to the point of connection of Ring D to the rest of the molecule with an $R^6$ group. Ring D may be a 6-membered heteroaryl group having 1 or 2 nitrogen atoms in the ring, said heteroaryl group being substituted at a position ortho to the point of connection of Ring D to the rest of the molecule with an $R^{6b}$ group.

Ring D may be a tetrazole ring. Said tetrazole ring is attached to a single $R^{6a}$ group; where $R^{6a}$ is independently selected from: H, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. Said tetrazole will typically be attached to ring B via the carbon atom of the tetrazole ring. Said tetrazole ring may be substituted with a single $R^{6b}$ group, wherein $R^{6b}$ is selected from $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^{6b}$ may be attached to a nitrogen atom neighbouring said carbon atom. Thus, ring D may be:

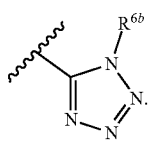

$R^{6a}$ may be independently selected from: H, $C_1$-$C_4$-alkyl, $C_2$-$C_4$-alkenyl and $C_2$-$C_4$-alkynyl. $R^{6a}$ may be independently selected from: H and $C_1$-$C_4$-alkyl. $R^{6a}$ may be independently selected from: $C_1$-$C_4$-alkyl, $C_2$-$C_4$-alkenyl and $C_2$-$C_4$-alkynyl. $R^{6a}$ may be H. Most preferably, $R^{6a}$ is $C_1$-$C_4$-alkyl, e.g. methyl.

$R^{6b}$ may be independently selected from: $C_1$-$C_4$-alkyl, $C_3$-$C_4$-alkenyl and $C_3$-$C_4$-alkynyl. Most preferably, $R^{6b}$ is $C_1$-$C_4$-alkyl, e.g. methyl.

Thus, ring D may be:

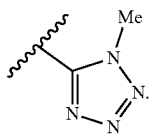

Ring D may be selected from isoxazole, pyrazole or isothiazole. Thus, Ring D may be:

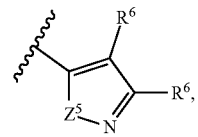

where $Z^5$ is selected from O, S and $NR^{6a}$. Ring D may be:

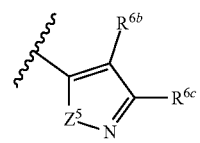

wherein $R^{6b}$ is selected from $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl and wherein $R^{6c}$ is selected from H and $R^6$. $Z^5$ may be S. $Z^5$ may be O. $Z^5$ may be $NR^{6a}$.

Alternatively, Ring D may be:

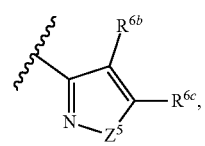

wherein $R^{6b}$ is selected from $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl; and wherein $R^{6c}$ is selected from H and $R^6$. $Z^5$ may be S. $Z^5$ may be O. $Z^5$ may be $NR^{6a}$.

Illustrative examples of Ring D include:

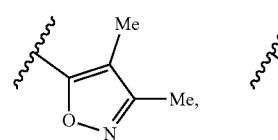 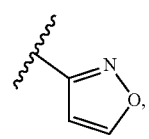

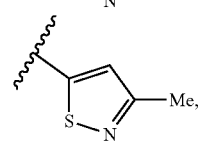 and 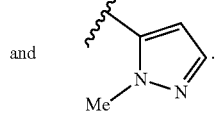

Ring D may be a 6-membered heteroaromatic ring. Ring D may be a pyridine. Ring D may be a 2-pyridine. Ring D may be a pyrazine. Ring D may be a pyrimidine. Ring D may be a pyridazine. Thus, Ring D may be

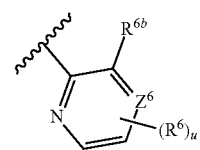

wherein $Z^6$ is independently selected from nitrogen or carbon; $R^{6b}$ is selected from $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl; and wherein u is an integer from 0 to 3. $Z^6$ may be carbon. $Z^6$ may be N. For the absence of doubt, where $Z^6$ is carbon, said carbon may be substituted with an $R^6$ group.

Ring D may be pyridyl. Ring D may be 2-pyridyl. Thus, ring D may be:

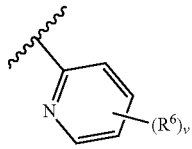

wherein v is an integer from 0 to 4.

Illustrative examples of Ring D include:

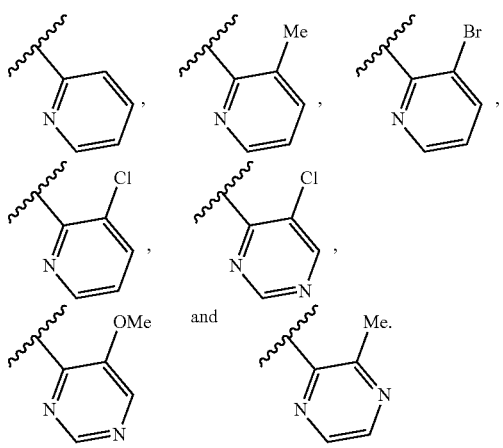

Ring D may be an imidazole. Ring D may have the structure:

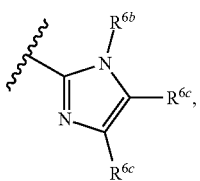

wherein $R^{6b}$ and $R^{6c}$ are as described above.

In certain illustrative examples, Ring D has the structure:

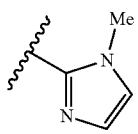

If attached to a carbon atom, $R^{6b}$ may be independently selected from: $C_1$-$C_4$-alkyl, $C_2$-$C_4$-alkenyl and $C_2$-$C_4$-alkynyl. If attached to a nitrogen atom, $R^{6b}$ may be independently selected from: $C_1$-$C_4$-alkyl, $C_3$-$C_4$-alkenyl and $C_3$-$C_4$-alkynyl. Most preferably, $R^{6b}$ is $C_1$-$C_4$-alkyl, e.g. methyl.

Ring D may be phenyl. Thus, ring D may be:

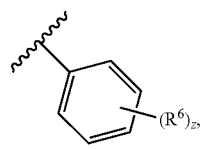

where z is an integer from 0 to 5.

Ring D may be substituted with from 1 to 5 $R^6$ groups. Ring D may be a 5- or 6-membered heteroaryl group substituted with from 1 to 5 $R^6$ groups. Ring D may be substituted with at least one $C_1$-$C_4$-alkyl group. Ring D may be a 5- or 6-membered heteroaryl group substituted with with at least one $C_1$-$C_4$-alkyl group.

$R^6$ is independently at each occurrence selected from: halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^6$ may be independently at each occurrence selected from halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl. $R^6$ may be independently at each occurrence selected from halo, cyano, $C_1$-$C_4$-alkyl and $C_1$-$C_4$-haloalkyl. $R^6$ may be independently at each occurrence selected from: halo, cyano, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

z may be an integer from 0 to 2. z may be an integer from 1 to 3, e.g. from 1 to 2. z may be 2. z may be 1. z may be 0. Thus, ring D may be unsubstituted phenyl.

Ring B and ring C together make a bicyclic heteroaryl group.

It may be that Ring B is independently a 5-membered heteroaryl ring, optionally further substituted with one $R^4$ group. Thus, it may be that the group

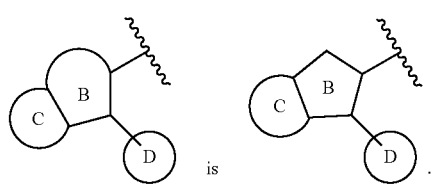

It may be that ring C is a benzene ring. Ring B and ring C may thus together form an indole or a benzimidazole. Where ring B and ring C form an indole, it may be that ring D is attached to the indole via the carbon atom of ring B. Alternatively, it may be that ring D is attached to the indole via the nitrogen atom of ring B.

Thus, it may be that the group

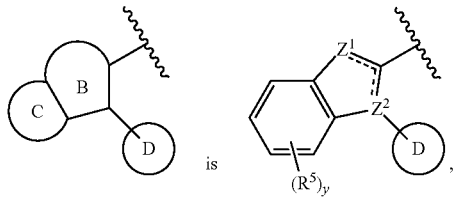

wherein $Z^1$ is selected from N, $CR^{4a}$ and $NR^{4b}$, $Z^2$ is selected from carbon and nitrogen; y is an integer from 0 to 4. For the absence of doubt, where $Z^2$ is nitrogen, the bond between $Z^2$ and the carbon between $Z^1$ and $Z^2$ is a single bond, the bond between $Z^1$ and the carbon between $Z^1$ and $Z^2$ is a double bond and $Z^1$ is selected from N and $CR^{4a}$. Likewise, where $Z^2$ is carbon, the bond between $Z^2$ and the carbon between $Z^1$ and $Z^2$ is a double bond, the bond between $Z^1$ and the carbon between $Z^1$ and $Z^2$ is a single bond and $Z^1$ is $NR^{4b}$. $R^{4a}$ is independently selected from: H, halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^{4b}$ is independently selected from H, $C_1$-$C_4$-alkyl, $C_3$-$C_4$-alkenyl, $C_3$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

$R^5$ is independently at each occurrence selected from: halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^5$ may be independently at each occurrence selected from halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl. $R^5$ may be independently at each occurrence selected from halo, cyano, $C_1$-$C_4$-alkyl and $C_1$-$C_4$-haloalkyl. $R^5$ may be independently at each occurrence selected from: halo, cyano, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

y may be an integer from 0 to 2. y may be an integer from 1 to 3, e.g. from 1 to 2. y may be 2. y may be 1. y may be 0. Thus, it may be that the group

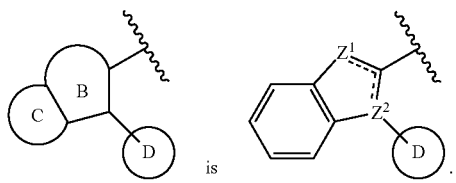

It may be that $Z^2$ is nitrogen. Thus, it may be that the group

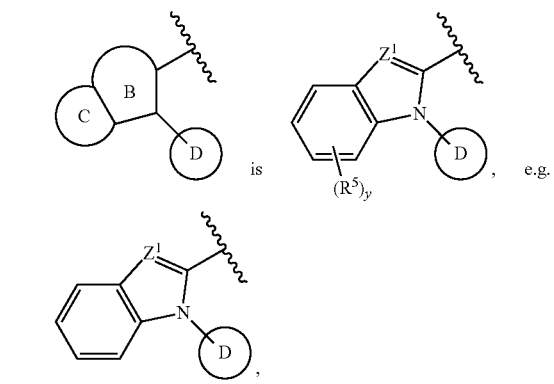

wherein $Z^1$ is independently selected from N and $CR^{4a}$.

It may be that $Z^1$ is N. Thus, it may be that the group

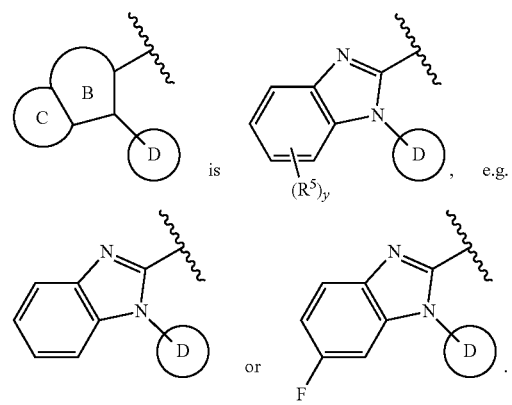

It may be that $Z^1$ is $CR^{4a}$. Thus, it may be that the group

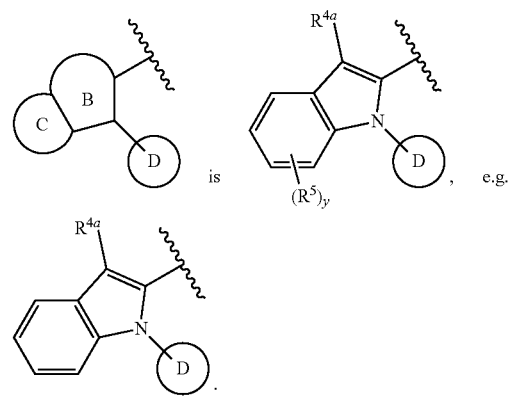

$R^{4a}$ may be independently selected from H, halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl. $R^{4a}$ may be independently selected from: H, halo, cyano, $C_1$-$C_4$-alkyl and $C_1$-$C_4$-haloalkyl. $R^{4a}$ may be independently selected from: H, halo, cyano, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

$R^{4a}$ may be $R^4$. $R^{4a}$ may thus be independently selected from: halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^{4a}$ may be independently selected from halo, nitro $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl. $R^{4a}$ may be independently selected from: halo, cyano, $C_1$-$C_4$-alkyl and $C_1$-$C_4$-haloalkyl. $R^{4a}$ may be independently selected from: halo, cyano, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

$R^{4a}$ may be H. Thus, it may be that the group

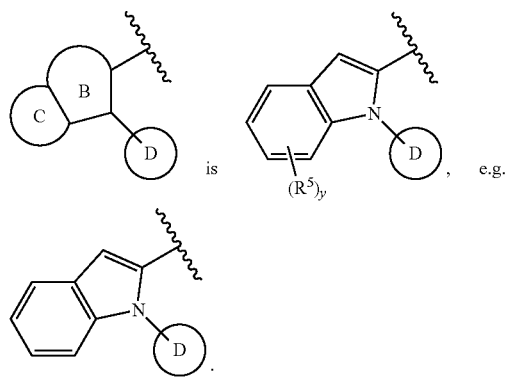

It may be that $Z^2$ is carbon. Thus, it may be that the group

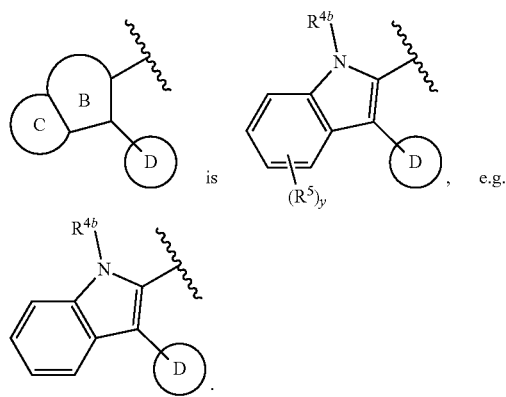

$R^{4b}$ may be independently selected from: H, $C_1$-$C_4$-alkyl, $C_3$-$C_4$-alkenyl and $C_3$-$C_4$-alkynyl. $R^{4b}$ may be independently selected from: H and $C_1$-$C_4$-alkyl. $R^{4b}$ may be independently selected from: $C_1$-$C_4$-alkyl, $C_3$-$C_4$-alkenyl and $C_3$-$C_4$-alkynyl. $R^{4b}$ may be H. $R^{4b}$ may be $C_1$-$C_4$-alkyl, e.g. methyl.

Where ring C is a benzene ring, ring D is preferably tetrazole. Any of the above embodiments in which ring C is a benzene ring may be combined with any of the above embodiments in which ring D is a tetrazole.

It may be that ring C is a tetrazole ring. Thus, it may be that the group

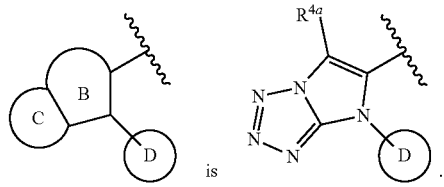

$R^{4a}$ may have any of the optional definitions provided above. $R^{4a}$ may, therefore, be H. Thus, it may be that the group

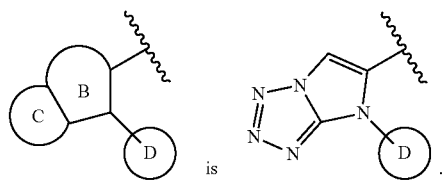

Alternatively, where ring C is tetrazole, it may be that the group

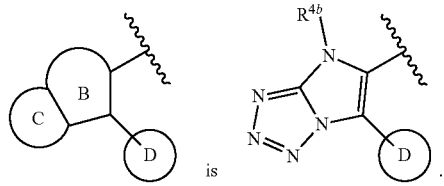

$R^{4b}$ may have any of the optional definitions provided above. $R^{4b}$ may, therefore, be H.

It may be that ring C is a 1,2,3-triazine ring. Thus, it may be that the group

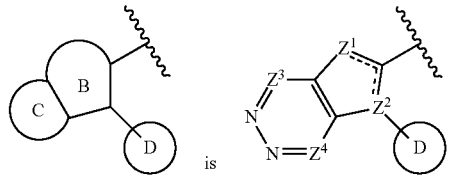

wherein $Z^1$ is selected from N, $CR^{4a}$ and $NR^{4b}$, $Z^2$ is selected from carbon and nitrogen; a single one of $Z^3$ and $Z^4$ is N and the other of $Z^3$ and $Z^4$ is $CR^{5a}$; $R^{5a}$ and $R^{4a}$ are each independently selected from: H, halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl; and $R^{4b}$ is independently selected from H, $C_1$-$C_4$-alkyl, $C_3$-$C_4$-alkenyl, $C_3$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

It may be that $Z^3$ is N and $Z^4$ is $CR^{5a}$. Thus, it may be that the group

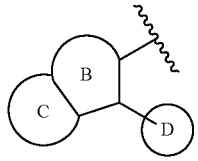 is 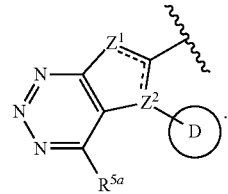

It may be that $Z^2$ is nitrogen. Thus, it may be that the group

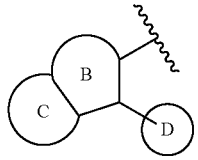 is 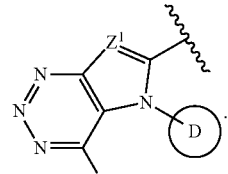

It may be that $Z^1$ is N. Thus, it may be that the group

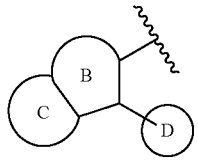 is 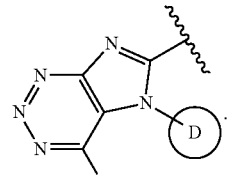

It may be that $Z^1$ is $CR^{4a}$. Thus, it may be that the group

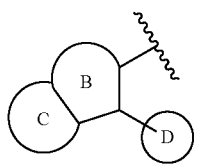 is 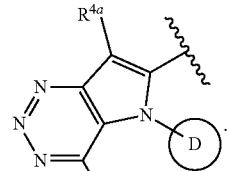

It may be that $Z^2$ is carbon. Thus, it may be that the group

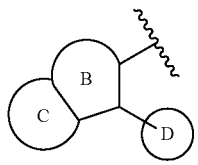 is 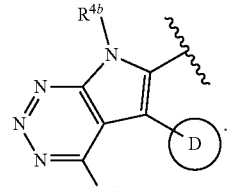

It may be that $Z^3$ is $CR^{5a}$ and $Z^4$ is N. Thus, it may be that the group

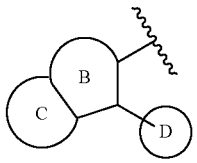 is 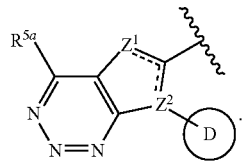

It may be that $Z^2$ is nitrogen. Thus, it may be that the group

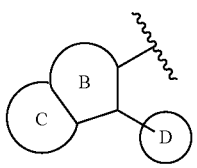 is 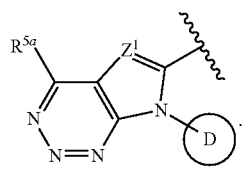

It may be that $Z^1$ is N. Thus, it may be that the group

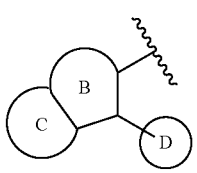 is 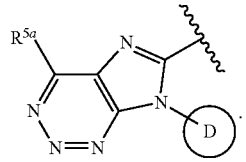

It may be that $Z^1$ is $CR^{4a}$. Thus, it may be that the group

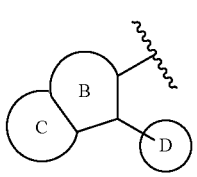 is 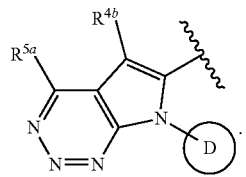

It may be that $Z^2$ is carbon. Thus, it may be that the group

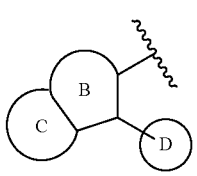 is 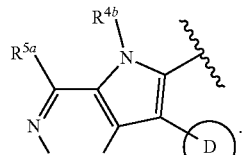

$R^{5a}$ may be independently selected from H, halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl.

$R^{5a}$ may be independently selected from: H, halo, cyano, $C_1$-$C_4$-alkyl and $C_1$-$C_4$-haloalkyl. $R^{5a}$ may be independently selected from: H, halo, cyano, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl. $R^{5a}$ may be as $R^5$. $R^{5a}$ may thus be independently selected from: halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, S(O)$_2$R$^{10}$, S(O)$_2$NR$^{10}$R$^{10}$, CO$_2$R$^{10}$, C(O)R$^{10}$, CONR$^{10}$R$^{10}$, C$_1$-C$_4$-alkyl, C$_2$-C$_4$-alkenyl, C$_2$-C$_4$-alkynyl, phenyl, C$_3$-C$_6$-cycloalkyl, $_{3-6}$-heterocycloalkyl, 5- or 6-membered heteroaryl and C$_1$-C$_4$-haloalkyl. R$^{5a}$ may be independently selected from halo, nitro, NR$^{10}$R$^{11}$, NR$^{10}$S(O)$_2$R$^{10}$, NR$^{10}$C(O)R$^{10}$, NR$^{10}$CONR$^{10}$R$^{10}$, NR$^{10}$CO$_2$R$^{10}$, OR$^{10}$, SR$^{10}$, S(O)R$^{10}$, S(O)$_2$R$^{10}$, S(O)$_2$NR$^{10}$R$^{10}$, CO$_2$R$^{10}$, C(O)R$^{10}$, CONR$^{10}$R$^{10}$, C$_1$-C$_4$-alkyl, C$_2$-C$_4$-alkenyl, C$_2$-C$_4$-alkynyl, and C$_1$-C$_4$-haloalkyl. R$^{5a}$ may be independently selected from: halo, cyano, C$_1$-C$_4$-alkyl and C$_1$-C$_4$-haloalkyl. R$^{5a}$ may be independently selected from: halo, cyano, C$_1$-C$_4$-alkyl, C$_2$-C$_4$-alkenyl, C$_2$-C$_4$-alkynyl, phenyl, C$_3$-C$_6$-cycloalkyl, $_{3-6}$-heterocycloalkyl, 5- or 6-membered heteroaryl and C$_1$-C$_4$-haloalkyl.

R$^{5a}$ may be H.

Where ring C is a 1,2,3-triazine ring, ring D is preferably phenyl. Any of the above embodiments in which ring C is a 1,2,3-triazine ring may be combined with any of the above embodiments in which ring D is a phenyl.

It may be that Ring B is independently a 6-membered heteroaryl ring, optionally further substituted with one or two R$^4$ groups. Thus, it may be that the group

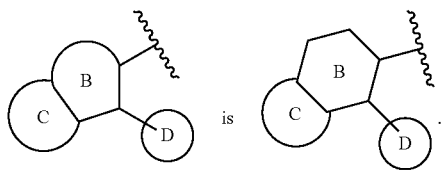

It may be that ring C is a tetrazole ring. Thus, it may be that the group

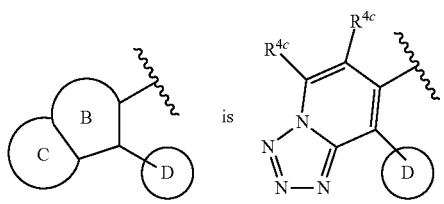

wherein R$^{4c}$ is independently at each occurrence selected from: H, halo, nitro, cyano, NR$^{10}$R$^{11}$, NR$^{10}$S(O)$_2$R$^{10}$, NR$^{10}$C(O)R$^{10}$, NR$^{10}$CONR$^{10}$R$^{10}$, NR$^{10}$CO$_2$R$^{10}$, OR$^{10}$, SR$^{10}$, S(O)R$^{10}$, S(O)$_2$R$^{10}$, S(O)$_2$NR$^{10}$R$^{10}$, CO$_2$R$^{10}$, C(O)R$^{10}$, CONR$^{10}$R$^{10}$, C$_1$-C$_4$-alkyl, C$_2$-C$_4$-alkenyl, C$_2$-C$_4$-alkynyl, phenyl, C$_3$-C$_6$-cycloalkyl, $_{3-6}$-heterocycloalkyl, 5- or 6-membered heteroaryl and C$_1$-C$_4$-haloalkyl.

Alternatively, it may be that the group

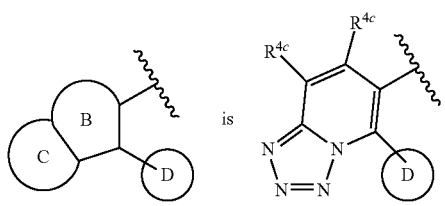

wherein R$^{4c}$ is independently at each occurrence selected from: H, halo, nitro, cyano, NR$^{10}$R$^{11}$, NR$^{10}$S(O)$_2$R$^{10}$, NR$^{10}$C(O)R$^{10}$, NR$^{10}$CONR$^{10}$R$^{10}$NR$^{10}$CO$_2$R$^{10}$, OR$^{10}$, SR$^{10}$, S(O)R$^{10}$, S(O)$_2$R$^{10}$, S(O)$_2$NR$^{10}$R$^{10}$, CO$_2$R$^{10}$, C(O)R$^{10}$, CONR$^{10}$R$^{10}$, C$_1$-C$_4$-alkyl, C$_2$-C$_4$-alkenyl, C$_2$-C$_4$-alkynyl, phenyl, C$_3$-C$_6$-cycloalkyl, $_{3-6}$-heterocycloalkyl, 5- or 6-membered heteroaryl and C$_1$-C$_4$-haloalkyl.

R$^{4c}$ may be independently at each occurrence selected from H, halo, nitro, cyano, NR$^{10}$R$^{11}$, NR$^{10}$S(O)$_2$R$^{10}$, NR$^{10}$C(O)R$^{10}$, NR$^{10}$CONR$^{10}$R$^{10}$, NR$^{10}$CO$_2$R$^{10}$, OR$^{10}$, SR$^{10}$, S(O)R$^{10}$, S(O)$_2$R$^{10}$, S(O)$_2$NR$^{10}$R$^{10}$, CO$_2$R$^{10}$, C(O)R$^{10}$, CONR$^{10}$R$^{10}$, C$_1$-C$_4$-alkyl, C$_2$-C$_4$-alkenyl, C$_2$-C$_4$-alkynyl, and C$_1$-C$_4$-haloalkyl. R$^{4c}$ may be independently at each occurrence selected from: H, halo, cyano, C$_1$-C$_4$-alkyl and C$_1$-C$_4$-haloalkyl. R$^{4c}$ may be independently at each occurrence selected from: H, halo, cyano, C$_1$-C$_4$-alkyl, C$_2$-C$_4$-alkenyl, C$_2$-C$_4$-alkynyl, phenyl, C$_3$-C$_6$-cycloalkyl, $_{3-6}$-heterocycloalkyl, 5- or 6-membered heteroaryl and C$_1$-C$_4$-haloalkyl. R$^{4c}$ may be R$^4$. R$^4$ may thus be independently at each occurrence selected from: halo, nitro, cyano, NR$^{10}$R$^{11}$, NR$^{10}$S(O)$_2$R$^{10}$, NR$^{10}$C(O)R$^{10}$, NR$^{10}$CONR$^{10}$R$^{10}$, NR$^{10}$CO$_2$R$^{10}$, OR$^{10}$, SR$^{10}$, S(O)R$^{10}$, S(O)$_2$R$^{10}$, S(O)$_2$NR$^{10}$R$^{10}$, CO$_2$R$^{10}$, C(O)R$^{10}$, CONR$^{10}$R$^{10}$, C$_1$-C$_4$-alkyl, C$_2$-C$_4$-alkenyl, C$_2$-C$_4$-alkynyl, phenyl, C$_3$-C$_6$-cycloalkyl, $_{3-6}$-heterocycloalkyl, 5- or 6-membered heteroaryl and C$_1$-C$_4$-haloalkyl. R$^{4c}$ may be independently at each occurrence selected from halo, nitro, cyano, NR$^{10}$R$^{11}$, NR$^{10}$S(O)$_2$R$^{10}$, NR$^{10}$C(O)R$^{10}$, NR$^{10}$CONR$^{10}$R$^{10}$, NR$^{10}$CO$_2$R$^{10}$, OR$^{10}$, SR$^{10}$, S(O)R$^{10}$, S(O)$_2$R$^{10}$, S(O)$_2$NR$^{10}$R$^{10}$, CO$_2$R$^{10}$, C(O)R$^{10}$, CONR$^{10}$R$^{10}$, C$_1$-C$_4$-alkyl, C$_2$-C$_4$-alkenyl, C$_2$-C$_4$-alkynyl, and C$_1$-C$_4$-haloalkyl. R$^{4c}$ may be independently at each occurrence selected from: halo, cyano, C$_1$-C$_4$-alkyl and C$_1$-C$_4$-haloalkyl. R$^{4c}$ may be independently at each occurrence selected from: halo, cyano, C$_1$-C$_4$-alkyl, C$_2$-C$_4$-alkenyl, C$_2$-C$_4$-alkynyl, phenyl, C$_3$-C$_6$-cycloalkyl, $_{3-6}$-heterocycloalkyl, 5- or 6-membered heteroaryl and C$_1$-C$_4$-haloalkyl.

R$^{4c}$ may in all occurrences be H. Thus, it may be that the group

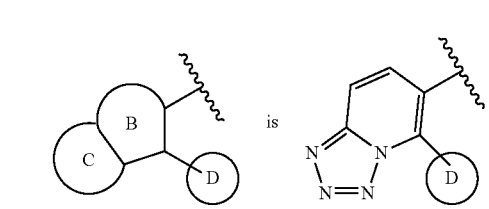

or it may be that the group is

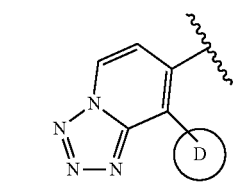

Where ring C is a tetrazole ring, ring D is preferably phenyl. Any of the above embodiments in which ring C is a tetrazole ring may be combined with any of the above embodiments in which ring D is a phenyl.

R$^{11}$ may be independently at each occurrence selected from H and C$_1$-C$_4$-alkyl.

The compound of formula (I) may be a compound selected from:
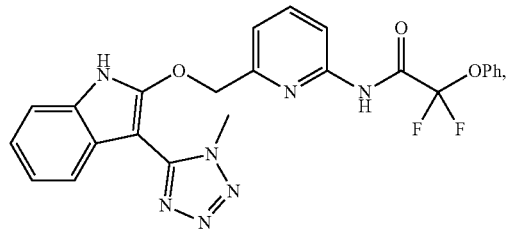
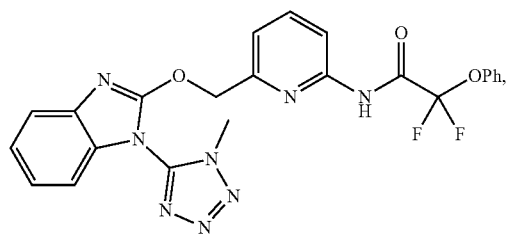
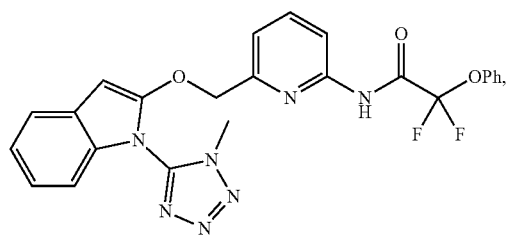
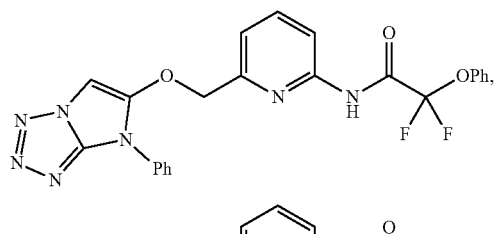
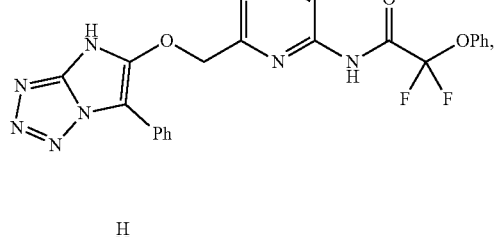
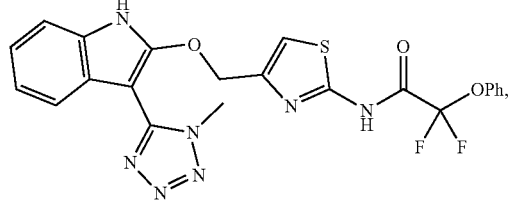
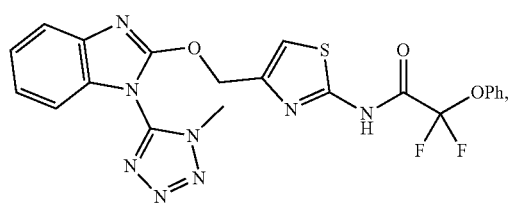
-continued
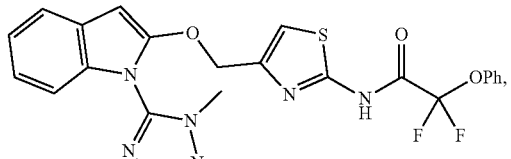
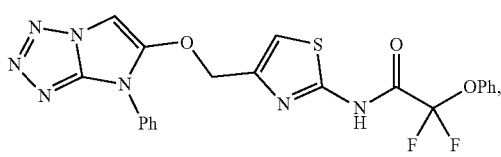
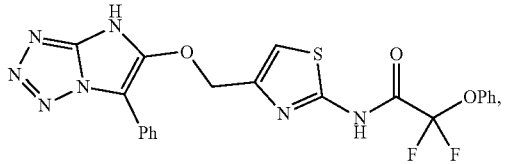
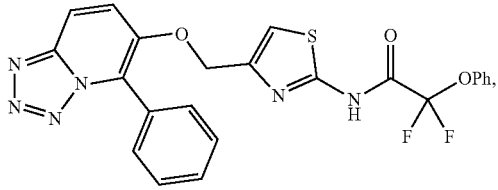
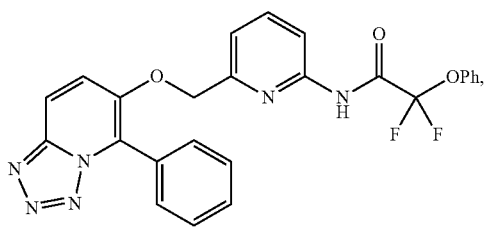
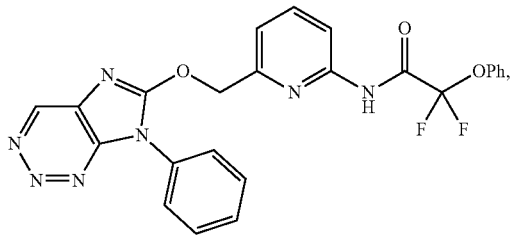
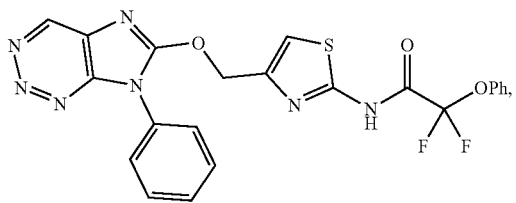
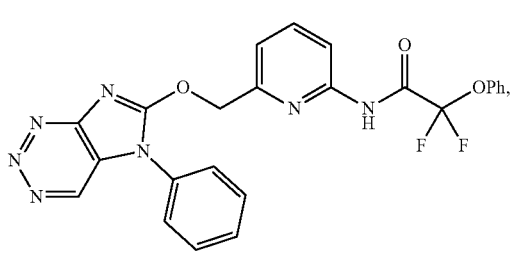

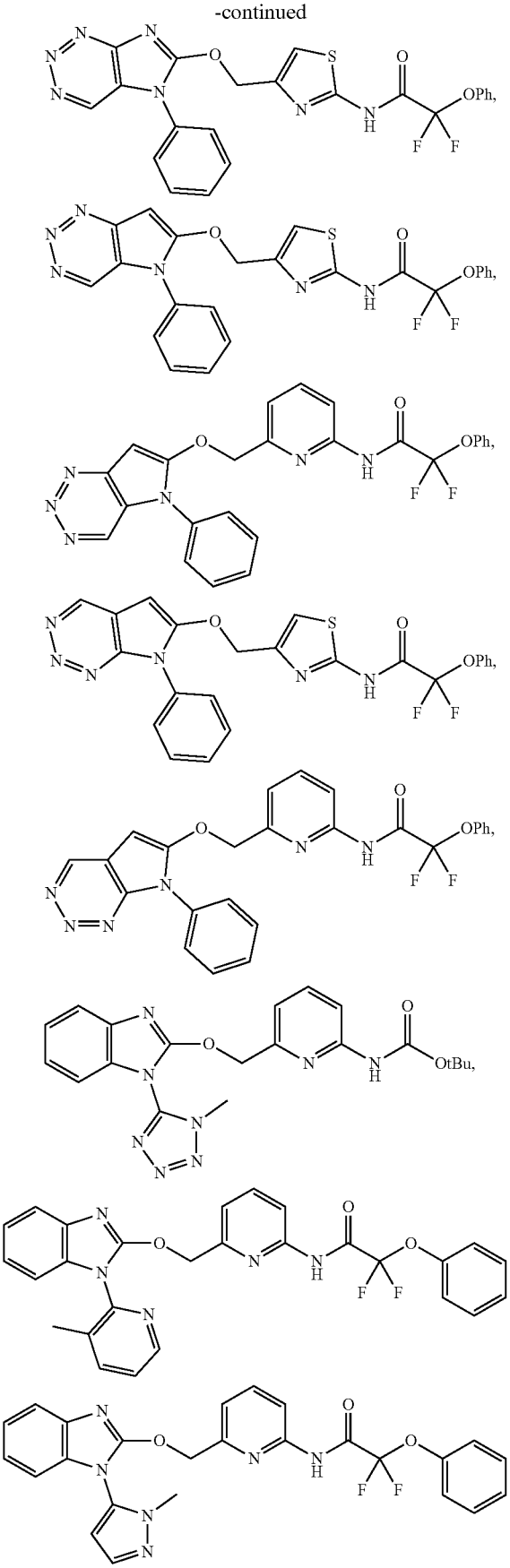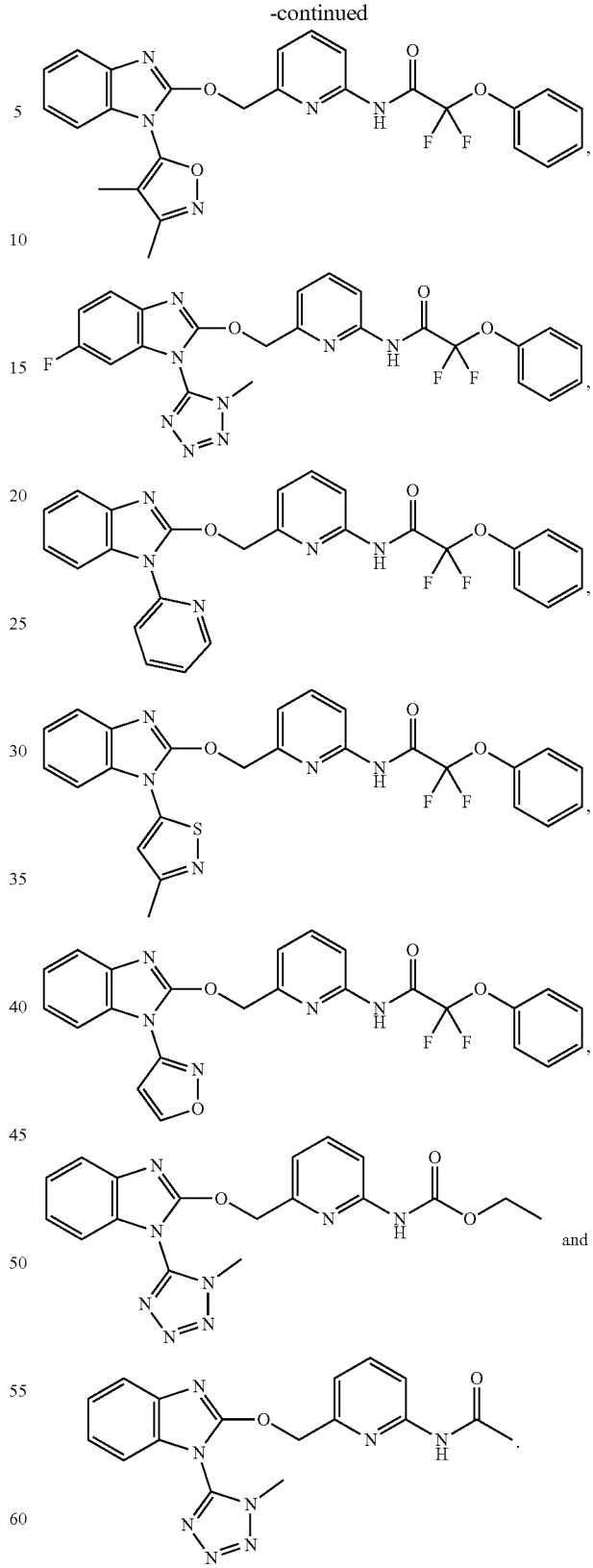
The compound of formula (I) may be any one of Examples 1 to 69.

The compound may be as described in the following numbered paragraphs:

1. A compound of formula (Ia):

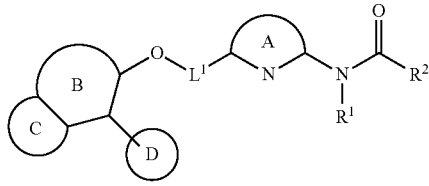

(Ia)

wherein Ring A is independently a 5- or 6-membered heteroaryl ring having a nitrogen in the position indicated, optionally further substituted with from 1 to 3 $R^3$ groups;

Ring B is independently a 5- or 6-membered heteroaryl ring, optionally further substituted with one or two $R^4$ groups;

Ring C is independently selected from a 5- or 6-membered heteroaryl ring and a benzene ring, optionally further substituted with from 1 to 4 $R^5$ groups;

Ring D is independently selected from 5- or 6-membered heteroaryl and phenyl, optionally further substituted with from 1 to 5 $R^6$ groups;

-$L^1$- is —$C_1$-$C_3$-alkylene-;

$R^1$, $R^9$ and $R^{10}$ are each independently at each occurrence selected from H and $C_1$-$C_4$-alkyl;

$R^2$ is independently selected from: $C_1$-$C_4$-alkyl, $C_2$-$C_4$-alkenyl, $C_2$-$C_4$-alkynyl, $C_3$-$C_6$-cycloalkyl, $_{3-6}$-heterocycloalkyl, 5- or 6-membered heteroaryl, phenyl and —$CR^7R^7L^3R^8$;

-$L^3$- is independently selected from —O—, —S— and —$NR^9$—;

$R^3$, $R^4$, $R^5$ and $R^6$ are each independently at each occurrence selected from: halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl;

$R^7$ is independently at each occurrence selected from F, H and $C_1$-$C_4$-alkyl;

$R^8$ is independently selected from H, $C_1$-$C_4$-alkyl, $C_2$-$C_4$-alkenyl, $C_2$-$C_4$-alkynyl, $C_3$-$C_6$-cycloalkyl, $_{3-6}$-heterocycloalkyl, 5- or 6-membered heteroaryl and phenyl; $R^{11}$ is independently at each occurrence selected from H, $C_3$-$C_6$-cycloalkyl, $C_1$-$C_4$-alkyl, $C(O)$—$C_1$-$C_4$-alkyl and $S(O)_2$—$C_1$-$C_4$-alkyl;

wherein where any $R^1$-$R^{11}$ group is an alkyl, haloalkyl, cycloalkyl, heterocycloalkyl, aryl or heteroaryl group, that alkyl, haloalkyl, cycloalkyl, heterocycloalkyl, aryl (e.g. phenyl) or heteroaryl group is optionally substituted, where chemically possible, by 1 to 5 substituents which are each independently at each occurrence selected from: oxo, =$NR^a$, =$NOR^a$, halo, nitro, cyano, $NR^aR^a$, $NR^aS(O)_2R^a$, $NR^aC(O)R^a$, $NR^aCONR^aR^a$, $NR^aCO_2R^a$, $OR^a$, $SR^a$, $S(O)R^a$, $S(O)_2R^a$, $S(O)_2NR^aR^a$, $CO_2R^a$ $C(O)R^a$, $CONR^aR^a$, $C_1$-$C_4$-alkyl, $C_2$-$C_4$-alkenyl, $C_2$-$C_4$-alkynyl and $C_1$-$C_4$-haloalkyl; wherein $R^a$ is independently at each occurrence selected from H, $C_1$-$C_4$ alkyl and $C_1$-$C_4$-haloalkyl;

or an agronomically acceptable salt or N-oxide thereof.

2. A compound of paragraph 1, wherein the group

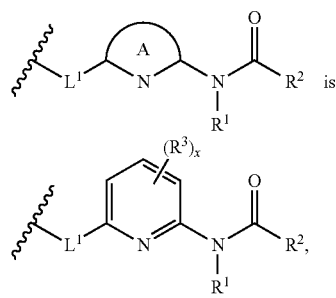

is wherein x is an integer from 0 to 3.

3. A compound of paragraph 1, wherein the group

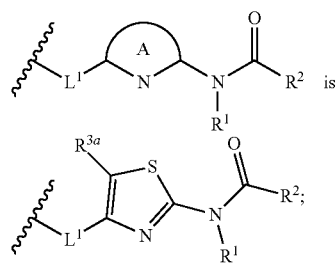

is where $R^{3a}$ is independently selected from H and $R^3$.

4. A compound of any preceding paragraph, wherein $R^1$ is H.

5. A compound of any preceding paragraph, wherein $R^2$ is —$CR^7R^7L^3R^8$.

6. A compound of paragraph 5, wherein -$L^3$- is —O—.

7. A compound of paragraph 5 or paragraph 6, wherein $R^7$ is at all occurrences be F.

8. A compound of any one of paragraphs 5 to 7, wherein $R^8$ is phenyl.

9. A compound of any preceding paragraph, wherein -L- is —$CH_2$—.

10. A compound of any preceding paragraph, wherein the group

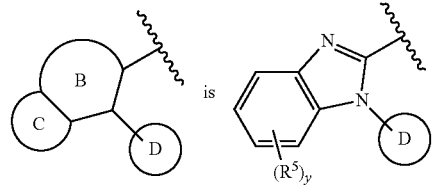

is

11. A compound of any one of paragraphs 1 to 9, wherein the group

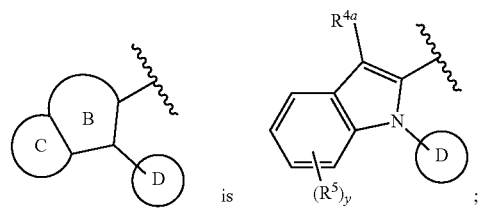

is wherein $R^{4a}$ is independently selected from H, halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl.

12. A compound of any one of paragraphs 1 to 9, wherein the group

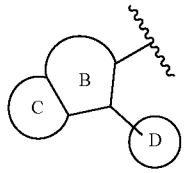 is 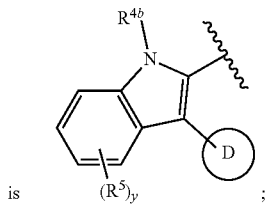 ;

wherein $R^{4b}$ is independently selected from: H, $C_1$-$C_4$-alkyl, $C_2$-$C_4$-alkenyl and $C_2$-$C_4$-alkynyl.

13. A compound of any one of paragraphs 1 to 9, wherein the group

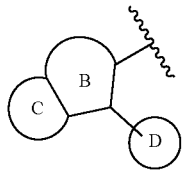 is 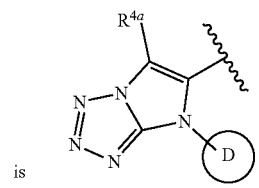 ;

wherein $R^{4a}$ is independently selected from H, halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl.

14. A compound of any one of paragraphs 1 to 9, wherein the group

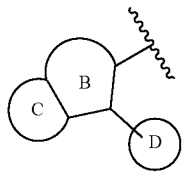 is 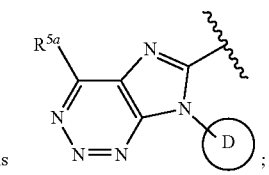 ;

wherein $R^{5a}$ is independently selected from H, halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl.

15. A compound of any one of paragraphs 1 to 9, wherein the group

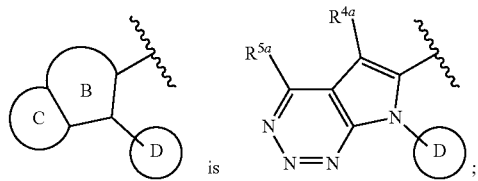 ;

wherein $R^{4a}$ is independently selected from H, halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl.

16. A compound of any one of paragraphs 1 to 9, wherein the group

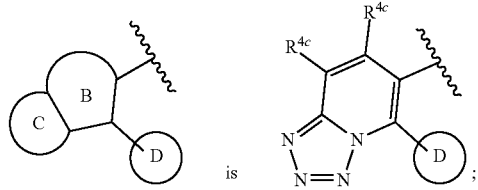 ;

wherein $R^{4c}$ is independently at each occurrence selected from: H, halo, nitro, cyano, $NR^{10}R^{11}$, $NR^{10}S(O)_2R^{10}$, $NR^{10}C(O)R^{10}$, $NR^{10}CONR^{10}R^{10}NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

17. A compound of any preceding paragraph, wherein Ring D is

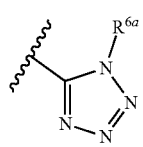

wherein $R^{6a}$ is independently selected from: H, $C_1$-$C_4$-alkyl, $C_2$-$C_4$-alkenyl and $C_2$-$C_4$-alkynyl.

18. A compound of any one of paragraphs 1 to 16, wherein Ring D is:

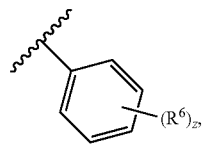

where z is an integer from 0 to 5.

19. A method for controlling fungal diseases, the method comprising applying an agronomically effective and substantially non-phytotoxic quantity of a compound of any one of paragraphs 1 to 18 to seeds of plants, to plants themselves or to an area where it is intended that plants will grow.

20. A use of a compound of any one of paragraphs 1 to 18 to control fungal diseases.

21. A fungicidal composition comprising an effective and non-phytotoxic amount of an active compound of any one of paragraphs 1 to 18.

22. A compound of formula (Ib):

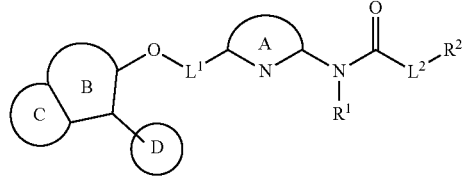

wherein Ring A is independently a 5- or 6-membered heteroaryl ring having a nitrogen in the position indicated, optionally further substituted with from 1 to 3 $R^3$ groups;

Ring B is independently a 5- or 6-membered heteroaryl ring, optionally further substituted with one or two $R^4$ groups;

Ring C is independently selected from a 5- or 6-membered heteroaryl ring and a benzene ring, optionally further substituted with from 1 to 4 $R^5$ groups;

Ring D is independently selected from 5- or 6-membered heteroaryl and phenyl, optionally further substituted with from 1 to 5 $R^6$ groups;

-$L^1$- is —$C_1$-$C_3$-alkylene-;

-$L^2$- is absent or is independently selected from —O—, —S— and —$NR^9$—;

$R^1$, $R^9$ and $R^{10}$ are each independently at each occurrence selected from H and $C_1$-$C_4$-alkyl;

$R^2$ is independently selected from: $C_1$-$C_6$-alkyl, $C_2$-$C_6$-alkenyl, $C_2$-$C_6$-alkynyl, $C_3$-$C_6$-cycloalkyl, $_{3-6}$-heterocycloalkyl, 5- or 6-membered heteroaryl, phenyl and —$CR^7R^7L^3R^8$;

-$L^3$- is independently selected from —O—, —S— and —$NR^9$—;

$R^3$, $R^4$, $R^5$ and $R^6$ are each independently at each occurrence selected from: halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl;

$R^7$ is independently at each occurrence selected from F, H and $C_1$-$C_4$-alkyl;

$R^8$ is independently selected from H, $C_1$-$C_4$-alkyl, $C_2$-$C_4$-alkenyl, $C_2$-$C_4$-alkynyl, $C_3$-$C_6$-cycloalkyl, $_{3-6}$-heterocycloalkyl, 5- or 6-membered heteroaryl and phenyl;

$R^{11}$ is independently at each occurrence selected from H, $C_3$-$C_6$-cycloalkyl, $C_1$-$C_4$-alkyl, $C(O)$—$C_1$-$C_4$-alkyl and $S(O)_2$—$C_1$-$C_4$-alkyl;

wherein where any $R^1$-$R^{11}$ group is an alkyl, haloalkyl, cycloalkyl, heterocycloalkyl, aryl or heteroaryl group, that alkyl, haloalkyl, cycloalkyl, heterocycloalkyl, aryl (e.g. phenyl) or heteroaryl group is optionally substituted, where chemically possible, by 1 to 5 substituents which are each independently selected at each occurrence from: oxo, =$NR^a$, =$NOR^a$, halo, nitro, cyano, $NR^aR^a$, $NR^aS(O)_2R^a$, $NR^aC(O)R^a$, $NR^aCONR^aR^a$, $NR^aCO_2R^a$, $OR^a$, $SR^a$, $S(O)R^a$, $S(O)_2R^a$, $S(O)_2NR^aR^a$, $CO_2R^a$ $C(O)R^a$, $CONR^aR^a$, $C_1$-$C_4$-alkyl, $C_2$-$C_4$-alkenyl, $C_2$-$C_4$-alkynyl and $C_1$-$C_4$-haloalkyl; wherein $R^a$ is independently at each occurrence selected from H, $C_1$-$C_4$ alkyl and $C_1$-$C_4$-haloalkyl;

or an agronomically acceptable salt or N-oxide thereof.

23. A compound of paragraph 22, wherein the group

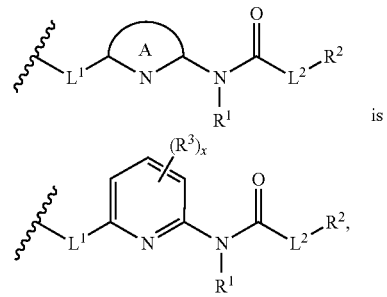

wherein x is an integer from 0 to 3.

24. A compound of paragraph 22, wherein the group

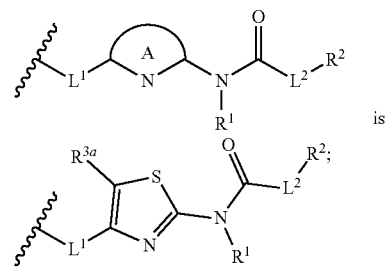

where $R^{3a}$ is independently selected from H and $R^3$.

25. A compound of any one of paragraphs 22 to 24, wherein $R^1$ is H.

26. A compound of any one of paragraphs 22 to 25, wherein -$L^2$- is absent and $R^2$ is —$CR^7R^7L^3R^8$.

27. A compound of paragraph 26, wherein -$L^3$- is —O—.

28. A compound of paragraph 28 or paragraph 27, wherein $R^7$ is at all occurrences be F.

29. A compound of any one of paragraphs 26 to 28, wherein $R^8$ is phenyl.

30. A compound of any one of paragraphs 22 to 29, wherein -$L^2$- is —O— and $R^2$ is independently selected from: $C_1$-$C_6$-alkyl, $C_2$-$C_6$-alkenyl, $C_2$-$C_6$-alkynyl, $C_3$-$C_6$-cycloalkyl, $_{3-6}$-heterocycloalkyl, 5- or 6-membered heteroaryl and phenyl.

31. A compound of any one of paragraphs 22 to 30, wherein -L- is -$CH_2$—.

32. A compound of any one of paragraphs 22 to 25, wherein the group

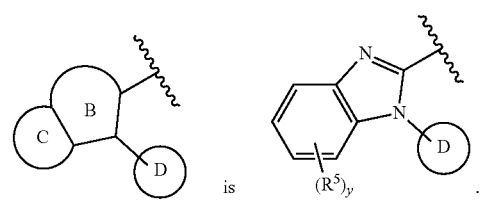

33. A compound of any one of paragraphs 22 to 31, wherein the group

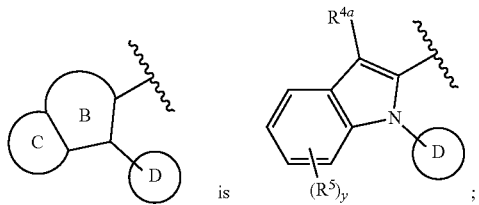

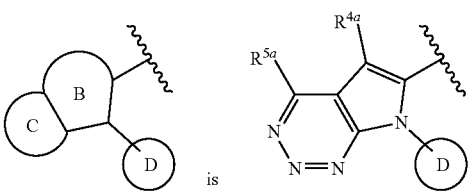

wherein $R^{4a}$ is independently selected from H, halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl.

34. A compound of any one of paragraphs 22 to 31, wherein the group

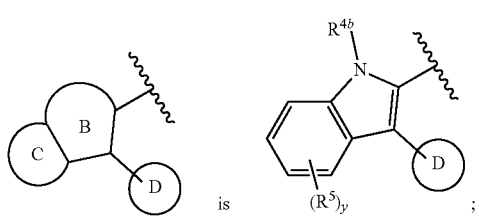

$R^{4b}$ is independently selected from: H, $C_1$-$C_4$-alkyl, $C_2$-$C_4$-alkenyl and $C_2$-$C_4$-alkynyl.

35. A compound of any one of paragraphs 22 to 31, wherein the group

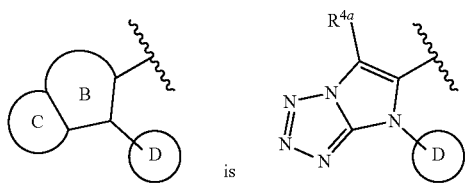

wherein $R^{4a}$ is independently selected from H, halo, nitro, cyano, $NR^{10}R^{10}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl.

36. A compound of any one of paragraphs 22 to 31, wherein the group

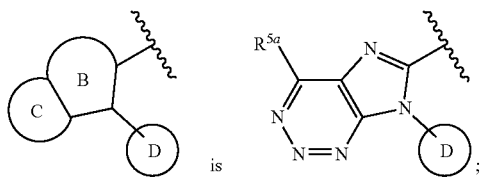

wherein $R^{5a}$ is independently selected from H, halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl.

37. A compound of any one of paragraphs 22 to 31, wherein the group wherein $R^{4a}$ is independently selected from H, halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl.

38. A compound of any one of paragraphs 22 to 31, wherein the group

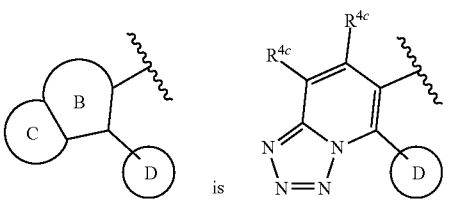

wherein $R^{4c}$ is independently at each occurrence selected from: H, halo, nitro, cyano, $NR^{10}R^{11}$, $NR^{10}S(O)_2R^{10}$, $NR^{10}C(O)R^{10}$, $NR^{10}CONR^{11}R^{10}NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_6$-cycloalkyl, $_{3-6}$-heterocycloalkyl, 5- or 6-membered heteroaryl and $C_1$-$C_4$-haloalkyl.

39. A compound of any one of paragraphs 22 to 38, wherein Ring D is a 5- or 6-membered heteroaryl group comprising 1, 2, 3 or 4 nitrogen atoms in the ring.

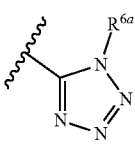

40. A compound of paragraph 39, wherein Ring D is N wherein $R^{6a}$ is independently selected from: H, $C_1$-$C_4$-alkyl, $C_2$-$C_4$-alkenyl and $C_2$-$C_4$-alkynyl.

41. A compound of any one of paragraphs 22 to 38, wherein Ring D is:

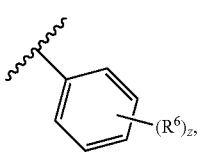

where z is an integer from 0 to 5.

43. A method for controlling fungal diseases, the method comprising applying an agronomically effective and substantially non-phytotoxic quantity of a compound of any one of paragraphs 22 to 41 to seeds of plants, to plants themselves or to an area where it is intended that plants will grow.

44. A use of a compound of any one of paragraphs 22 to 41 to control fungal diseases.

DETAILED DESCRIPTION

The term $C_m$-$C_n$ refers to a group with m to n carbon atoms.

The term "alkyl" refers to a monovalent linear or branched saturated hydrocarbon chain. For example, $C_1$-$C_6$-alkyl may refer to methyl, ethyl, n-propyl, iso-propyl, n-butyl, sec-butyl, tert-butyl, n-pentyl and n-hexyl. The alkyl groups may be unsubstituted or substituted by one or more substituents. Specific substituents for each alkyl group independently may be fluorine, $OR^a$ or $NHR^a$.

The term "alkylene" refers to a bivalent linear saturated hydrocarbon chain. For example, $C_1$-$C_3$-alkylene may refer to methylene, ethylene or propylene. The alkylene groups may be unsubstituted or substituted by one or more substituents. Specific substituents for each alkylene group independently may be methyl, fluorine, $OR^a$ or $NHR^a$.

The term "haloalkyl" refers to a hydrocarbon chain substituted with at least one halogen atom independently chosen at each occurrence from: fluorine, chlorine, bromine and iodine. The halogen atom may be present at any position on the hydrocarbon chain. For example, $C_1$-$C_6$-haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. A haloalkyl group may be a fluoroalkyl group, i.e. a hydrocarbon chain substituted with at least one fluorine atom. Thus, a haloalkyl group may have any amount of halogen substituents. The group may contain a single halogen substituent, it may have two or three halogen substituents, or it may be saturated with halogen substituents.

The term "alkenyl" refers to a branched or linear hydrocarbon chain containing at least one double bond. The double bond(s) may be present as the E or Z isomer. The double bond may be at any possible position of the hydrocarbon chain. For example, "$C_2$-$C_6$-alkenyl" may refer to ethenyl, propenyl, butenyl, butadienyl, pentenyl, pentadienyl, hexenyl and hexadienyl. The alkenyl groups may be unsubstituted or substituted by one or more substituents. Specific substituents for any saturated carbon atom in each alkenyl group independently may be fluorine, $OR^a$ or $NHR^a$.

The term "alkynyl" refers to a branched or linear hydrocarbon chain containing at least one triple bond. The triple bond may be at any possible position of the hydrocarbon chain. For example, "$C_2$-$C_6$-alkynyl" may refer to ethynyl, propynyl, butynyl, pentynyl and hexynyl. The alkynyl groups may be unsubstituted or substituted by one or more substituents. Specific substituents for any saturated carbon atom in each alkynyl group independently may be fluorine, $OR^a$ or $NHR^a$.

The term "cycloalkyl" refers to a saturated hydrocarbon ring system containing 3, 4, 5 or 6 carbon atoms. For example, "$C_3$-$C_6$-cycloalkyl" may refer to cyclopropyl, cyclobutyl, cyclopentyl, cyclohexyl. The cycloalkyl groups may be unsubstituted or substituted by one or more substituents. Specific substituents for each cycloalkyl group independently may be fluorine, $OR^a$ or $NHR^a$.

The term "$_{y-z}$-membered heterocycloalkyl" refers to a y- to z-membered heterocycloalkyl group. Thus it may refer to a monocyclic or bicyclic saturated or partially saturated group having from y to z atoms in the ring system and comprising 1 or 2 heteroatoms independently selected from O, S and N in the ring system (in other words 1 or 2 of the atoms forming the ring system are selected from O, S and N). By partially saturated it is meant that the ring may comprise one or two double bonds. This applies particularly to monocyclic rings with from 5 to 6 members. The double bond will typically be between two carbon atoms but may be between a carbon atom and a nitrogen atom. Examples of heterocycloalkyl groups include; piperidine, piperazine, morpholine, thiomorpholine, pyrrolidine, tetrahydrofuran, tetrahydrothiophene, dihydrofuran, tetrahydropyran, dihydropyran, dioxane, azepine. A heterocycloalkyl group may be unsubstituted or substituted by one or more substituents. Specific substituents for any saturated carbon atom in each heterocycloalkyl group may independently be fluorine, $OR^a$ or $NHR^a$.

Aryl groups may be any aromatic carbocyclic ring system (i.e. a ring system containing $2(2n+1)\pi$ electrons). Aryl groups may have from 6 to 10 carbon atoms in the ring system. Aryl groups will typically be phenyl groups. Aryl groups may be naphthyl groups or biphenyl groups.

In any of the above aspects and embodiments, heteroaryl groups may be any aromatic (i.e. a ring system containing $2(2n+1)\pi$ electrons) 5 or 6 membered ring system comprising from 1 to 4 heteroatoms independently selected from O, S and N (in other words from 1 to 4 of the atoms forming the ring system are selected from O, S and N). Thus, any heteroaryl groups may be independently selected from: 5 membered heteroaryl groups in which the heteroaromatic ring is substituted with 1-4 heteroatoms independently selected from O, S and N; and 6-membered heteroaryl groups in which the heteroaromatic ring is substituted with 1-3 (e.g. 1-2) nitrogen atoms. Specifically, heteroaryl groups may be independently selected from: pyrrole, furan, thiophene, pyrazole, imidazole, oxazole, isoxazole, triazole, oxadiazole, thiadiazole, tetrazole; pyridine, pyridazine, pyrimidine, pyrazine, triazine.

It may be that, in any group which is an aryl or heteroaryl group, that aryl or heteroaryl group may be unsubstituted or is optionally substituted, where chemically possible, by 1 to 5 substituents which are each independently selected at each occurrence from: halo, nitro, cyano, $NR^aR^a$, $NR^aS(O)_2R^a$, $NR^aC(O)R^a$, $NR^aCONR^aR^a$, $NR^aCO_2R^a$, $OR^a$, $SR^a$, $S(O)R^a$, $S(O)_2R^a$, $S(O)_2NR^aR^a$, $CO_2R^a$ $C(O)R^a$, $CONR^aR^a$, $CR^bR^bNR^aR^a$, $CR^bR^bOR^a$, $C_1$-$C_4$-alkyl, $C_2$-$C_4$-alkenyl, $C_2$-$C_4$-alkynyl and $C_1$-$C_4$-haloalkyl; wherein $R^a$ is as described above for formula I.

Compounds of the invention containing one or more asymmetric carbon atoms can exist as two or more stereoisomers. Where a compound of the invention contains a double bond such as a C=C or C=N group, geometric cis/trans (or Z/E) isomers are possible. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of the invention, including compounds exhibiting more than one type of isomerism, and mixtures of one or more thereof. Also included are acid addition or base salts wherein the counter ion is optically active, for example, d-lactate or -lysine, or racemic, for example, dl-tartrate or dl-arginine.

The compounds of the invention may be obtained, stored and/or used in the form of an agronomically acceptable salt. Suitable salts include, but are not limited to, salts of acceptable inorganic acids such as hydrochloric, sulphuric, phosphoric, nitric, carbonic, boric, sulphamic, and hydrobromic acids, or salts of agronomically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids. Suitable salts also include salts of inorganic and organic bases, e.g. counterions such as Na, Ca, K, Li, Mg, ammonium, trimethylsulphonium. The compounds may also be obtained, stored and/or used in the form of an N-oxide.

Cis/trans isomers may be separated by conventional techniques well known to those skilled in the art, for example, chromatography and fractional crystallisation.

Conventional techniques for the preparation/isolation of individual enantiomers when necessary include chiral synthesis from a suitable optically pure precursor or resolution of the racemate (or the racemate of a salt or derivative) using, for example, chiral high pressure liquid chromatography (HPLC). Thus, chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and for specific examples, 0 to 5% by volume of an alkylamine e.g. 0.1% diethylamine. Concentration of the eluate affords the enriched mixture.

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

The activity of the compounds of the present invention can be assessed by a variety of in silico, in vitro and in vivo assays. In silico analysis of a variety of compounds has been demonstrated to be predictive of ultimate in vitro and even in vivo activity.

The present invention also includes all environmentally acceptable isotopically-labelled compounds of formulae (I) to (IX) and their syntheses, wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Isotopically-labelled compounds can generally be prepared by conventional techniques known to those skilled in the art or by processes analogous to those described using an appropriate isotopically-labelled reagent in place of the non-labelled reagent previously employed.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

If appropriate, the compounds of the invention can, at certain concentrations or application rates, be used as fungicides.

According to another aspect of the present invention, there is provided a method for controlling the fungal diseases of plants, crops or seeds, the method comprising applying an agronomically effective and substantially non-phytotoxic quantity of a compound according to the invention to the seeds of the plants, to the plants or to the area where it is intended that the plants will grow.

The pesticide may be applied as a seed treatment, foliar application, stem application, drench or drip application (chemigation) to the seed, the plant or to the fruit of the plant or to soil or to inert substrate (e.g. inorganic substrates like sand, rockwool, glasswool; expanded minerals like perlite, vermiculite, zeolite or expanded clay), Pumbe, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics).

In a further aspect, the present invention also relates to a fungicidal composition comprising an effective and non-phytotoxic amount of an active compound of the invention. The composition may further comprise one or more additional fungicides.

The term "effective and non-phytotoxic amount" means an amount of pesticide according to the invention which is sufficient to control or destroy any of the targeted pests present or liable to appear on the crops and which does not have any significant detrimental effect on the crops or indeed has a positive effect on plant vigour and yield in the absence of target organism. The amount will vary depending on the pest to be controlled, the type of crop, the climatic conditions and the compounds included in the pesticidal composition. This amount can be determined by systematic field trials, which are within the capabilities of a person skilled in the art.

Depending on their particular physical and/or chemical properties, the active compounds of the invention can be formulated as solutions, emulsions, suspensions, powders, foams, pastes, granules, aerosols, microencapsulations in polymeric substances and in coating materials for seed, and also as ULV cold and warm fogging formulations.

The active compounds can be used neat, or in the form of a formulation, e.g. ready-to-use solutions, emulsions, water- or oil-based suspensions, powders, wettable powders, pastes, soluble powders, dusts, soluble granules, granules for broadcasting, suspoemulsion concentrates, natural substances impregnated with active compound, synthetic substances impregnated with active compound, fertilizers and also microencapsulations in polymeric substances. Application may be carried out, for example, by watering, spraying, atomizing, broadcasting, dusting, foaming, spreading, etc. It is also possible to apply the active compounds by the ultra-low volume method or to inject the preparation of active compound or the active compound itself into the soil. It is also possible to treat the seed of the plants.

Formulations containing the compounds of the invention are produced in a known manner, for example by mixing the compounds with extenders (e.g. liquid solvents and/or solid carriers), optionally with the use of surfactants (e.g. emulsifiers and/or dispersants and/or foam-formers). The formulations are prepared either in factories/production plants or alternatively before or during the application.

Auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to use, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide.

Suitable solid carriers are: for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

Further additives may be mineral and vegetable oils. It is also possible to add colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc. Other possible additives are perfumes, mineral or vegetable, optionally modified oils and waxes.

The formulations may also comprise stabilizers, e.g. low-temperature stabilizers, preservatives, antioxidants, light stabilizers or other agents which improve chemical and/or physical stability.

The formulations generally comprise between 0.01 and 98% by weight of active compound, preferably between 0.1 and 95% and particularly preferably between 0.5 and 90%.

The active compounds according to the invention can also be used as a mixture with other known fungicides, for example, to improve the activity spectrum or to reduce or slow the development of resistance.

A mixture with other known active compounds such as nematicides, acaricides, herbicides, insecticides or bactericides, or with fertilizers and growth regulators, safeners or semiochemicals is also possible.

Exemplary application rates of the active compounds according to the invention are: when treating leaves: from 0.1 to 10 000 g/ha, preferably from 10 to 1000 g/ha, particularly preferably from 50 to 300 g/ha (when the application is carried out by watering or dripping, it is even possible to reduce the application rate, especially when inert substrates such as rock wool or perlite are used); when treating seed: from 2 to 200 g per 100 kg of seed, preferably from 2.5 to 150 g per 100 kg of seed, and particularly preferably from 2.5 to 25 g per 100 kg of seed, very particularly preferably from 2.5 to 12.5 g per 100 kg of seed; when treating the soil: from 0.1 to 10 000 g/ha, preferably from 1 to 5000 g/ha.

The compositions according to the invention are suitable for protecting any plant variety which is employed in agriculture, in the greenhouse, in forests or in horticulture and, in particular, cereals (e.g. wheat, barley, rye, millet and oats), maize, cotton, soya beans, rice, potatoes, sunflowers, beans, coffee, beet (for example sugar beet and fodder beet), peanuts, vegetables (e.g. tomatoes, cucumbers, onions and lettuce), lawns, fruit and nut trees (e.g. apples pears peaches nectarines, apricots, hazelnut, pecan, macadamia, pistachio), soft fruit (e.g. strawberries, raspberries, blackcurrants, redcurrants), grapevines, bananas, cocoa and ornamental plants.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling pests, in particular fungal diseases, which are encountered in agriculture, in horticulture, in animal husbandry, in forests, in gardens and leisure facilities, in the protection of stored products and of materials, and in the hygiene sector. They may be preferably employed as crop protection agents.

Use as Fungicides

The compounds of the invention have activity as fungicides.

The following are illustrative examples of agricultural pests that may be controlled by fungicidal compounds:

Powdery mildew diseases such as: Blumeria diseases, caused for example by *Blumeria graminis*; Podosphaera diseases, caused for example by *Podosphaera leucotheca*; Sphaerotheca diseases, caused for example by *Sphaerotheca fuliginea*; Uncinula diseases, caused for example by *Uncinula necator;*

Rust diseases such as: Gymnosporangium diseases, caused for example by *Gymnosporangium sabinae*; Hemileia diseases, caused for example by *Hemileia vastatix*; Phakopsora diseases, caused for example by *Phakopsora pachyrhizi* or *Phakopsora meibomiae*; Puccinia diseases, caused for example by *Puccinia recondita*; Uromyces diseases, caused for example by *Uromyces appendiculatus;*

Oomycete diseases such as: Albugo diseases caused for example by *Albugo Candida*; Bremia diseases, caused for example by *Bremia lactucae*; Peronospora diseases, caused for example by *Peronospora pisi* or *P. brassicae*; Phytophthora diseases, caused for example by *Phytophthora infestans*; Plasmopara diseases, caused for example by *Plasmopara viticola*; Pseudoperonospora diseases, caused for example by *Pseudoperonospora humuli* or *Pseudoperonospora cubensis*; Pythium diseases, caused for example by *Pythium ultimum*; Leafspot, leaf blotch and leaf blight diseases such as: Alternaria diseases, caused for example by *Alternaria solani*; Cercospora diseases, caused for example by *Cercospora beticola*; Cladiosporum diseases, caused for example by *Cladiosporium cucumerinum*; Cochliobolus diseases, caused for example by *Cochliobolus sativus*; Colletotrichum diseases, caused for example by *Colletotrichum lindemuthanium*; Cycloconium diseases, caused for example by *Cycloconium oleaginum*; Diaporthe diseases, caused for example by *Diaporthe citri; Drechslera,* Syn: *Helminthosporium*) or *Cochliobolus miyabeanus*; Elsinoe diseases, caused for example by *Elsinoe fawcettii*; Gloeosporium diseases, caused for example by *Gloeosporium laeticolor*; Glomerella diseases, caused for example by *Glomerella cingulata*; Guignardia diseases, caused for example by *Guignardia bidwelli*; Leptosphaeria diseases, caused for example by *Leptosphaeria maculans; Leptosphaeria nodorum*; Magnaporthe diseases, caused for example by *Magnaporthe grisea*; Mycosphaerella diseases, caused for example by *Mycosphaerella graminicola; Mycosphaerella arachidtola; Mycosphaerella fibensis*; Phaeosphaeria diseases, caused for example by *Phaeosphaera nodorum*; Pyrenophora diseases, caused for example by *Pyrenophora teres*; Ramularia diseases, caused for example by *Ramularia collo-cygni*; Rhynchosporium diseases, caused for example by *Rhynchosporium secalis*; Septoria diseases, caused for example by *Septoria apii* or *Septoria lycopercisi*; Typhula diseases, caused for example by *Typhula incarnata*; Venturia diseases, caused for example by *Venturia inaequalis;*

Root and stem diseases such as: Corticium diseases, caused for example by *Corticium graminearum*; Fusarium diseases, caused for example by *Fusarium oxysporum*; Gaeumannomyces diseases, caused for example by *Gaeumannomyces graminis*; Rhizoctonia diseases, caused for example by *Rhizoctonia solani*; Sarocladium diseases caused for example by *Sarocladium oryzae*; Sclerotium diseases caused for example by *Sclerotium oryzae*; Tapesia diseases, caused for example by *Tapesia acuformis*; Thielavbpsis diseases, caused for example by *Thielaviopsis basicola;*

Ear and panicle diseases including maize cob, such as: Alternaria diseases, caused for example by *Alternaria* spp.; Aspergillus diseases, caused for example by *Aspergillus flavus*; Cladosporium diseases, caused for example by *Cladosporium* spp.; Claviceps diseases, caused for example by *Claviceps purpurea*; Fusarium diseases, caused for example by *Fusarium culmorum*; Gibberella diseases, caused for example by *Gibberella zeae*; Monographella diseases, caused for example by *Monographella nivalis;*

Smut and bunt diseases such as: Sphacelotheca diseases, caused for example by *Sphacelotheca reiliana*; Tilletia diseases, caused for example by *Tilletia caries*; Urocystis diseases, caused for example by *Urocystis occulta*; Ustilago diseases, caused for example by *Ustilago nuda;*

Fruit rot and mould diseases such as: Aspergillus diseases, caused for example by *Aspergillus flavus*; Botrytis diseases, caused for example by *Botrytis cinerea*; Penicillium diseases, caused for example by *Penicillium expansum*; Rhizopus diseases caused by example by *Rhizopus stolonifer*; Sclerotinia diseases, caused for example by *Sclerotinia sclerotiorum*; Verticilium diseases, caused for example by *Verticilium alboatrum;*

Seed and soil borne decay, mould, wilt, rot and damping off diseases such as: Alternaria diseases, caused for example by *Alternaria brassicicola*; Aphanomyces diseases, caused for example by *Aphanomyces euteiches*; Ascochyta diseases, caused for example by *Ascochyta lentis* Aspergillus diseases, caused for example by *Aspergillus flavus*; Cladosporium diseases, caused for example by *Cladosporium herbarum*; Cochliobolus diseases, caused for example by *Cochliobolus sativus* (Conidiaform: *Drechslera, Bipolaris* Syn: *Helminthosporium*); Colletotrichum diseases, caused for example by *Colletotrichum coccodes*; Fusarium diseases, caused for example by *Fusarium culmorum*; Gibberella diseases, caused for example by *Gibberella zeae*; Macrophomina diseases, caused for example by *Macrophomina phaseolina* Monographella diseases, caused for example by *Monographella nivalis*; Penicillium diseases, caused for example by *Penicillium expansum*; Phoma diseases, caused for example by *Phoma lingam*; Phomopsis diseases, caused for example by *Phomopsis sojae*; Phytophthora diseases, caused for example by *Phytophthora cactorum*; Pyrenophora diseases, caused for example by *Pyrenophora graminea* Pyricularia diseases, caused for example by *Pyricularia oryzae*; Pythium diseases, caused for example by *Pythium ultimum*; Rhizoctonia diseases, caused for example by *Rhizoctonia solani*; Rhizopus diseases, caused for example by *Rhizopus oryzae*; Sclerotium diseases, caused for example by *Sclerotium rolfsii*; Septoria diseases, caused for example by *Septoria nodorum*; Typhula diseases, caused for example by *Typhula incarnata*; Verticillium diseases, caused for example by *Verticillium dahliae*;

Canker, broom and dieback diseases such as: Nectria diseases, caused for example by *Nectria galligena*;

Blight diseases such as:

Monilinia diseases, caused for example by *Monilinia laxa*;

Leaf blister or leaf curl diseases such as: Exobasidium diseases caused for example by *Exobasidium vexans*; Taphrina diseases, caused for example by *Taphrina deformans*; —Decline diseases of wooden plants such as:

Esca diseases, caused for example by *Phaemoniella clamydospora, Phaeomoniella clamydospora, Phaeoacremonium aleophilum* and *Fomitiporia mediterranea*;

Eutypa dyeback, caused for example by *Eutypa lata*; Dutch elm disease, caused for example by *Ceratocystsc ulmi*; Ganoderma diseases caused by example by *Ganoderma boninense*;

Diseases of flowers and seeds such as: Botrytis diseases, caused for example by *Botrytis cinerea*;

Diseases of tubers such as: Rhizoctonia diseases, caused for example by *Rhizoctonia solani* Helminthosporium diseases, caused for example by *Helminthospohum solani*.

Diseases of Tubers such as

Rhizoctonia diseases caused for example by *Rhizoctonia solani*; Helminthosporium diseases caused for example by *Helminthospohum solani*;

Club root diseases such as

Plasmodiophora diseases, caused for example by *Plamodiophora brassicae*.

The compounds of the invention may be active against a broad spectrum of fungal diseases. Alternatively they may be active specifically against cereal fungal diseases or they may be specifically active against oomycete diseases. The compounds of the invention have been found to be particularly effective against oomycete fungal diseases.

Notable oomycete fungal diseases are:

*Plamopara viticola*

*Phytophthora infestans*

*Pythium ultimum*

*Bremia lactuca*

*Peronospora* spp

In additional to their fungicidal activity, the compounds of the invention may also have some activity against other microbes, e.g. bacteria.

The fungicidal compounds of the invention may also be used in the treatment of fungal diseases of humans and animals (e.g. mammals). Likewise, the bactericidal compounds of the invention may be used in the treatment of bacterial diseases of humans and animals. Thus, the invention includes a method of treating a fungal or bacterial disease, the method comprising administering a therapeutic amount of an antifungal agent of the invention to a subject (e.g. a human subject) in need thereof. The compound may be formulated for topical administration to the infected area of the body or it may be formulated for oral or parenteral administration.

Use as Nematicides

The compounds of the invention can be used as nematicides.

Phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis,* *Rotylenchus* spp., *Trichodorus* spp., *Tylenchorhynchus* spp., *Tylenchulus* spp., *Tylenchulus semipenetrans, Xiphinema* spp.

Synthesis

The skilled person will appreciate that adaptation of methods known in the art could be applied in the manufacture of the compounds of the present invention.

For example, the skilled person will be immediately familiar with standard textbooks such as "Comprehensive Organic Transformations—A Guide to Functional Group Transformations", R C Larock, Wiley-VCH (1999 or later editions); "March's Advanced Organic Chemistry—Reactions, Mechanisms and Structure", MB Smith, J. March, Wiley, (5th edition or later); "Advanced Organic Chemistry, Part B, Reactions and Synthesis", F A Carey, R J Sundberg, Kluwer Academic/Plenum Publications, (2001 or later editions); "Organic Synthesis—The Disconnection Approach", S Warren (Wiley), (1982 or later editions); "Designing Organic Syntheses" S Warren (Wiley) (1983 or later editions); "Heterocyclic Chemistry", J. Joule (Wiley 2010 edition or later); ("Guidebook To Organic Synthesis" R K Mackie and D M Smith (Longman) (1982 or later editions), etc., and the references therein as a guide.

The skilled person is familiar with a range of strategies for synthesising organic and particularly heterocyclic molecules and these represent common general knowledge as set out in text books such as Warren "Organic Synthesis: The Disconnection Approach"; Mackie and Smith "Guidebook to Organic Chemistry"; and Clayden, Greeves, Warren and Wothers "Organic Chemistry".

The skilled chemist will exercise his judgement and skill as to the most efficient sequence of reactions for synthesis of a given target compound and will employ protecting groups as necessary. This will depend inter alia on factors such as the nature of other functional groups present in a particular substrate. Clearly, the type of chemistry involved will influence the choice of reagent that is used in the said synthetic steps, the need, and type, of protecting groups that are employed, and the sequence for accomplishing the protection/deprotection steps. These and other reaction parameters will be evident to the skilled person by reference to standard textbooks and to the examples provided herein.

Sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc. (1999), and references therein.

Throughout this specification these abbreviations have the following meanings:

CDI—carbonyldiimidazole DCM—dichloromethane
DDQ—2,3-dichloro-5,6-dicyano-1,4-benzoquinone
DIPEA—diisopropylethylamine
DMAP—N,N-dimethyl-4-aminopyridine DMF—N,N-dimethylformamide
DMSO—dimethylsulphoxide
HATU—1-[Bis(dimethylamino)methylene]-1H-1,2,3-triazolo[4,5-b]pyridinium 3-oxide
Im—imidazole LDA—Lithium diisopropylamide
NBS—N-bromosuccinimide PE—petroleum ether
PMB—para-methoxybenzyl TBAF—tetrabutylammonium fluoride
TBSO—t-butyldimethylsilyloxy TCDI—thiocarbonyldiimidazole
Tf—trifluoromethylsulphonyl THF—tetrahydrofuran
TMS—trimethylsilyl Certain compounds of the invention can be made according to the general synthetic schemes below. Certain compounds of the invention can be made according to or by methods analogous to the methods described below for the synthesis of Examples 1 to 69.

General Synthetic Schemes

Certain compounds of the invention can be made starting from nitro aldehyde A. Wittig reaction (e.g. using the ylid formed from PPh$_3$, chloroform and a base, e.g. tBuOK) followed by reduction of the nitro group (e.g. using hydrogen gas and platinum) can provide amine B. Mesylation of amine B (e.g. by treating with MsCl in the presence of a base, e.g. Et$_3$N) followed by treatment with TBAF can provide indole C. Reaction with Im-CONHR$^{6b}$ in the presence of a Lewis Acid (e.g. AlMe$_3$) can provide amide D. Reaction with sodium azide can provide tetrazole E. A coupling reaction with alcohol F can provide compounds of formula G, a subset of compounds of the invention (Scheme A).

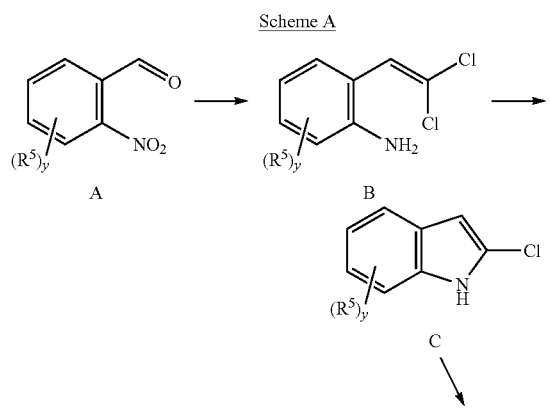

Treatment of amine B with Cs$_2$CO$_3$ can provide indole H. Conversion of the carboxylic acid to an acid chloride (e.g. using (COCl)$_2$) and reaction with NH$_2$R$^{6b}$ can provide the amide J which, on reaction with sodium azide can provide tetrazole K. A coupling reaction with alcohol F can provide compounds of formula L, a subset of compounds of the invention (Scheme B).

Certain compounds of the invention can be prepared starting with nitrobenzene M. Fluorine displacement with amine N can provide tetrazole O. Reduction of the nitro group (e.g. with NH₄HCO₂ in the presence of palladium on carbon) can provide the corresponding amine and reaction with CDI can provide urea P. Deprotonation of the urea (e.g. with NaH) and reaction with triflate Q (prepared from alcohol F) can provide benzimidazole R, a subset of compound of the invention (Scheme C).

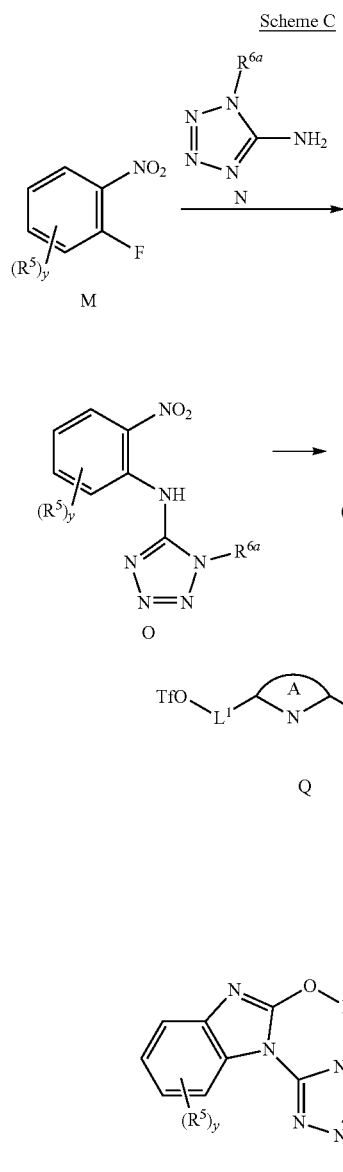

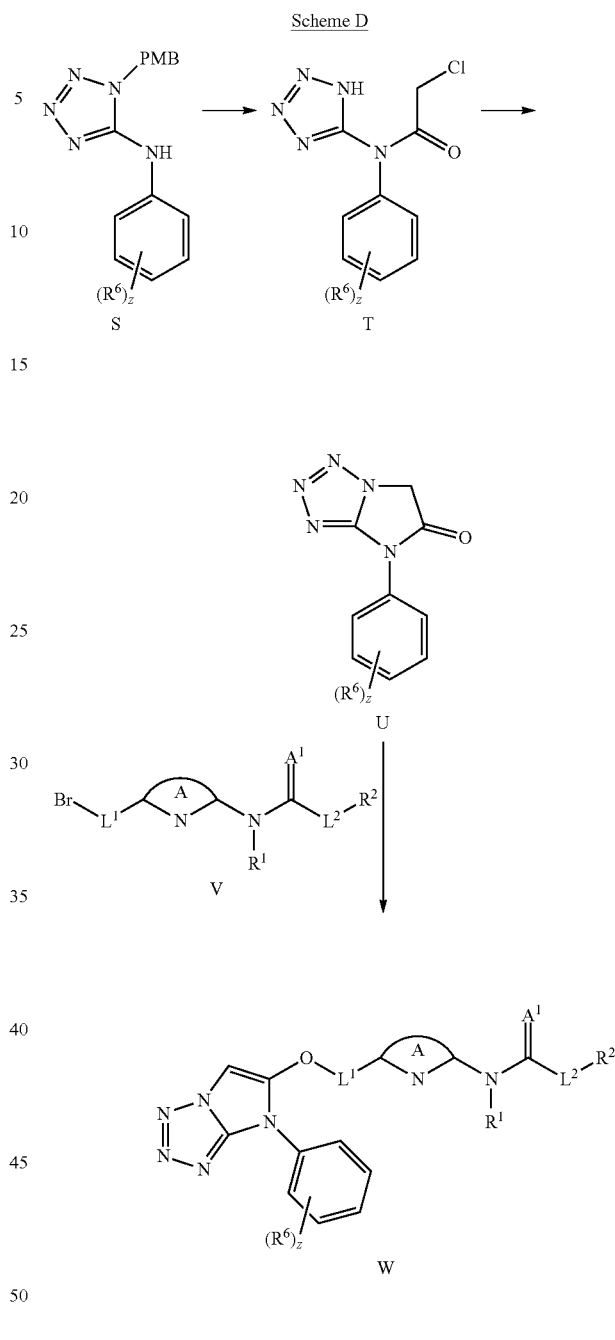

Certain compounds of the invention can be prepared starting with protected tetrazole S. Treatment with ClCH₂COCl (e.g. in the presence of DMAP and Et₃N) followed by removal of the PMB protecting group (e.g. with DDQ and a trace of water) can provide tetrazole T. Cyclisation (e.g. following treatment with a base) can provide lactam U which upon deprotonation (e.g. with LDA) and reaction with bromide V (prepared from alcohol F) can provide benzimidazole W, a subset of compound of the invention (Scheme D).

Certain compounds of the invention can be prepared starting with pyridinium salt Y. Treatment with TMSN₃ can provide tetrazole Z which can be converted to bromide AA using NBS. Treatment with alcohol F (e.g. in the presence of copper and KOH) can provide tetrazole AB, a subset of compound of the invention (Scheme E).

Certain compounds of the invention can be prepared starting with dinitrile AC. Treatment with amine AD can provide imidazole AE. Bromination (e.g. with NBS) followed by treatment with alcohol F (e.g. in the presence of a base and copper bromide) can provide imidazole AF. Treatment with NaNO₂ in HCl can provide triazide AG, a subset of compounds of the invention. Removal of the chloride from triazide AG, e.g. using hydrogen gas and palladium on carbon, can provide triazide AH, a further subset of compounds of the invention (Scheme F).
Scheme E
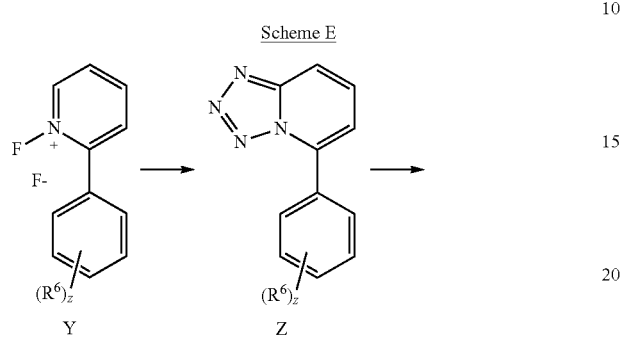
-continued
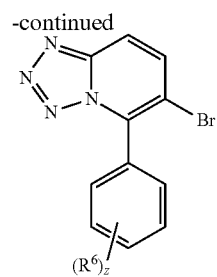
AA
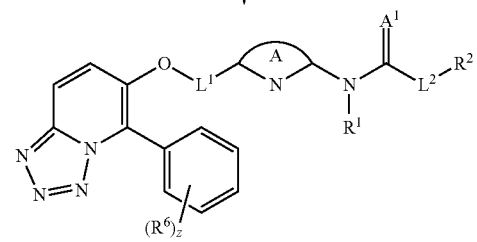
AB
Scheme F
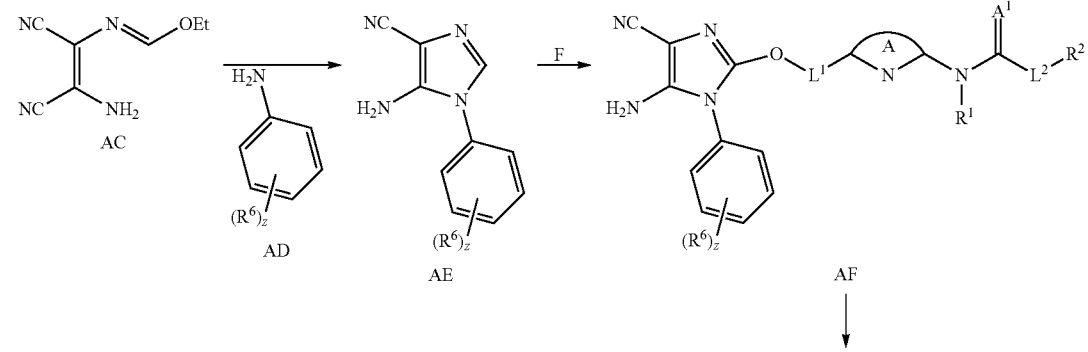
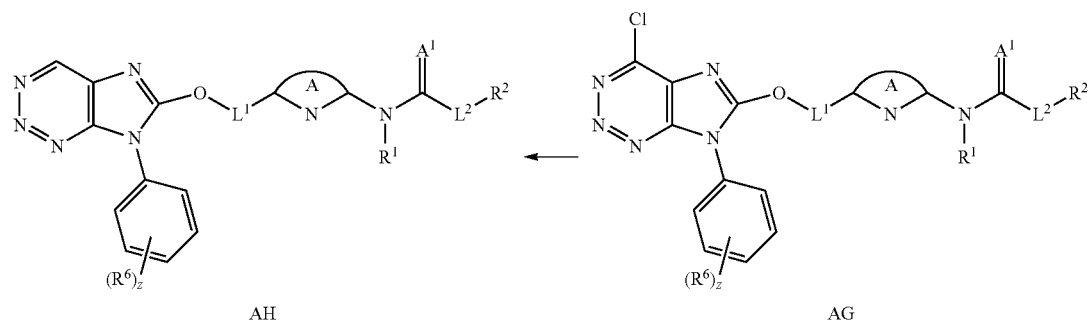

Certain compounds of the invention can be made starting from amide AI. Treatment with malononitrile (e.g. in the presence of tBuOK) can provide lactam AJ. Treatment with acidic NaNO$_2$ in HCl and subsequent removal of the chloride, e.g. using hydrogen gas and palladium on carbon, can provide triazide AK. Deprotonation (e.g. with LDA) and reaction with triflate Q can provide triazide AL, a subset of compound of the invention (Scheme G)

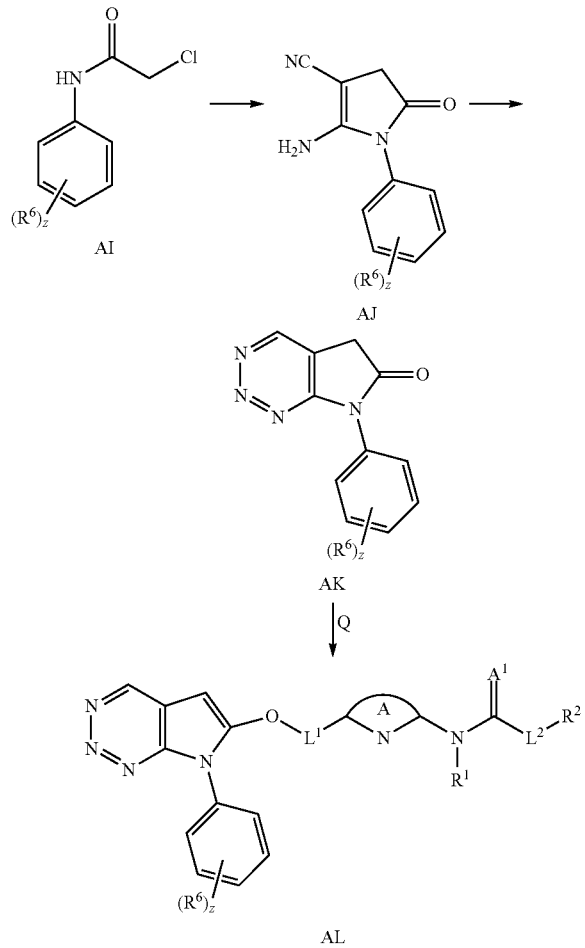

Scheme G

AI

AJ

AK

AL

Analytical Procedures

Flash chromatography was carried out using a Biotage Isolera 4, with Biotage® SNAP KP-Sil cartridges, packed with 50 μm silica particles with a surface area of 500 m$^2$/g, or alternative cartridges (e.g. Puriflash, produced by Interchim) where stated. Visualisation was carried out with UV light (254 nm) and by staining with either potassium permanganate, phosphomolybdic acid (PMA) or ninhydrin solutions.

All $^1$H NMR spectra were obtained on a Bruker AVIII 400 with 5 mm QNP or Bruker AVI 500 with 5 mm QNP or Bruker DPX 300. Chemical shifts are expressed in parts per million (δ) and are referenced to the solvent. Coupling constants J are expressed in Hertz (Hz).

MS was carried out on a Waters Alliance ZQ MS, using a YMC-Triart C18 50×2 mm, 5 micron LC column (solvent: 5-90% gradient of acetonitrile in water (with 1% by volume of 28% (by weight) aqueous ammonia solution)) by Method A, or (solvent: 5-90% gradient of acetonitrile in water (with 1% formic acid) by Method B. Flow rate 0.8 mL/min. Wavelengths were 254 and 210 nM.

Method A (5 Minute Basic pH)

Column: YMC-Triart C18 50×2 mm, 5 μm. Flow rate: 0.8 mL/min. Injection volume: 5 μL. Mobile Phase

| A | H$_2$O |
| B | CH$_3$CN |
| C | 50% H$_2$O/50% CH$_3$CN + 1.0% ammonia (aq.) |

| Time (min) | A (%) | B (%) | C (%) |
| --- | --- | --- | --- |
| 0 | 95 | 0 | 5 |
| 4 | 0 | 95 | 5 |
| 4.4 | 0 | 95 | 5 |
| 4.5 | 95 | 5 | 0 |
| 4.5 | | STOP | |

Method B (5 Minute Acidic pH)

Column: YMC-Triart C18 50×2 mm, 5 μm. Flow rate: 0.8 mL/min. Injection volume: 5 μL. Mobile Phase

| A | H$_2$O |
| B | CH$_3$CN |
| C | 50% H$_2$O/50% CH$_3$CN + 1.0% formic acid |

| Time (min) | A (%) | B (%) | C (%) |
| --- | --- | --- | --- |
| 0 | 95 | 0 | 5 |
| 4 | 0 | 95 | 5 |
| 4.4 | 0 | 95 | 5 |
| 4.5 | 95 | 5 | 0 |
| 4.5 | | STOP | |

Method C (15 Minute Basic pH)

Column YMC Triart-C18 50×2 mm, 5 μm Flow rate: 0.8 mL/min. Injection volume: 10 μL Mobile Phase

| A | H$_2$O |
| B | CH$_3$CN |
| C | 50% H$_2$O/50% CH$_3$CN + 1.0% ammonia (aq.) |

| Time (min) | A (%) | B (%) | C (%) |
| --- | --- | --- | --- |
| 0 | 95 | 0 | 5 |
| 2.0 | 95 | 0 | 5 |
| 12.0 | 0 | 95 | 5 |
| 14.0 | 0 | 95 | 5 |
| 14.2 | 95 | 0 | 5 |

Method D (15 Minute Acidic pH)

Column YMC Triart-C18 50×2 mm, 5 μm Flow rate: 0.8 mL/min. Injection volume: 10 μL Mobile Phase

| A | H$_2$O |
| B | CH$_3$CN |
| C | 50% H$_2$O/50% CH$_3$CN + 1.0% formic acid |

| Time (min) | A (%) | B (%) | C (%) |
|---|---|---|---|
| 0 | 95 | 0 | 5 |
| 2.0 | 95 | 0 | 5 |
| 12.0 | 0 | 95 | 5 |
| 14.0 | 0 | 95 | 5 |
| 14.2 | 95 | 0 | 5 |

Alternatively MS was carried on a Waters Acquity UPLC-QDA UV-MS system using Method E (high pH) or Method F (low pH):

Method E (3.5 Minute Basic pH)

Mobile phases: Water (A)/Acetonitrile (B) both with 0.1% (v/v) Ammonia

| Time | % A | % B | Flow rate (mL/min) |
|---|---|---|---|
| Initial | 98 | 2 | 1.0 |
| 0.2 | 98 | 2 | 1.0 |
| 2.5 | 2 | 98 | 1.0 |
| 3.0 | 2 | 98 | 1.0 |
| 3.1 | 98 | 2 | 1.0 |
| 3.5 | 98 | 2 | 1.0 |

Column: BEH C18 2.1×50 mm, 1.7 μm @ 50° C.

Method F (3.5 Minute Acidic pH)

Mobile phases: Water (A)/Acetonitrile (B) both with 0.1% (v/v) Formic Acid

| Time | % A | % B | Flow rate (mL/min) |
|---|---|---|---|
| Initial | 98 | 2 | 1.0 |
| 0.2 | 98 | 2 | 1.0 |
| 2.5 | 2 | 98 | 1.0 |
| 3.0 | 2 | 98 | 1.0 |
| 3.1 | 98 | 2 | 1.0 |
| 3.5 | 98 | 2 | 1.0 |

Column: CSH C18 2.1×50 mm, 1.7 μm @ 50° C.

All reagents were obtained from commercial suppliers and used as supplied unless otherwise stated.

All examples are named using ChemBioDraw Ultra 14.0.

Reactions were conducted at ambient temperature (RT) unless otherwise stated.

Synthetic Intermediates 2,2-Difluoro-2-phenoxy Acetic Acid A

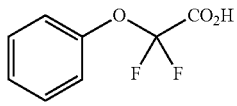 [SMILES: O=C(O)C(F)(F)Oc1ccccc1]

Sodium hydride (4.36 g, 109 mmol) was added in several portions to a stirred solution of phenol (5 g, 53.1 mmol) and chlorodifluoroacetic acid (4.50 ml, 53.1 mmol) in 1,4-dioxane (200 ml) at 0° C. and the reaction mixture was stirred at 0° C. until effervescence ceased. The reaction mixture was slowly heated to 101° C. and was allowed to reflux for 16 hours. The mixture was concentrated in vacuo. Ethyl acetate (300 mL) and water (200 mL) were added and the biphasic mixture was stirred vigorously for 30 minutes at room temperature. The pH of the separated aqueous phase was adjusted to pH 1 with 5 M hydrochloric acid and then to pH 8 with a saturated solution of sodium bicarbonate. The solution was extracted with ethyl acetate (2×150 mL) to remove unreacted phenol and these extracts were discarded. The aqueous phase was acidified to pH 1 with 5M HCl and extracted with ethyl acetate (3×150 mL). The organic layers were combined, washed with brine, dried (MgSO₄), filtered and concentrated to give 2,2-difluoro-2-phenoxyacetic acid A (7.36 g, 74%) as a pale brown oil, purity ca. 90% by NMR.

$^1$H NMR (500 MHz, CDCl₃) δ 9.36 (br. s, 1H), 7.44-7.31 (m, 2H), 7.35-7.18 (m, 3H); LCMS (method A): 0.89 min (187.2, [M-H]⁻)

6-[(tert-Butyl(dimethyl)silyl)oxymethyl]pyridin-2-amine B

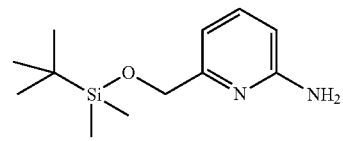 [SMILES: CC(C)(C)[Si](C)(C)OCc1cccc(N)n1]

A solution of (6-aminopyridin-2-yl)methanol (2.983 g, 24.03 mmol) in DMF (20 mL) was treated with imidazole (3.44 g, 50.5 mmol) and tert-butyldimethylchlorosilane (3.80 g, 25.2 mmol) at 25° C. After 22 h the solution was diluted with EtOAc (100 mL), washed with water (3×100 mL) and brine, dried (MgSO₄) and concentrated to give 6-(((tert-butyldimethylsilyl)oxy)methyl)pyridin-2-amine B (5.85 g, 100%) as a waxy solid.

$^1$H NMR (500 MHz, CDCl₃) δ 7.48-7.41 (m, 1H), 6.86 (dd, J=7.4, 0.8 Hz, 1H), 6.37 (dd, J=8.1, 0.7 Hz, 1H), 4.66 (s, 2H), 4.39 (s, 2H), 0.95 (s, 9H), 0.11 (s, 6H); LCMS (method A): 3.38 (239, MH⁺)

N-[6-[(tert-Butyl(dimethyl)silyl)oxymethyl]-2-pyridyl]-2,2-difluoro-2-phenoxy-acetamide C

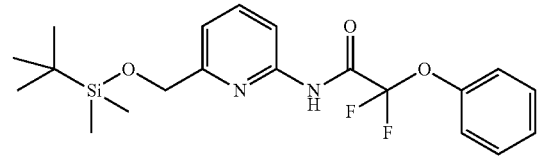 [SMILES: CC(C)(C)[Si](C)(C)OCc1cccc(NC(=O)C(F)(F)Oc2ccccc2)n1]

To a solution of 2,2-difluoro-2-phenoxy acetic acid A (284 mg, 1.51 mmol) in DCM (5 mL) and DMF (2 drops) was added oxalyl chloride (0.24 mL, 2.77 mmol) dropwise and the mixture was stirred at room temperature for 90 minutes before the volatiles were removed in vacuo. The residue was dissolved in toluene (2.5 mL) and added to a solution of 6-[(tert-butyl(dimethyl)silyl)oxymethyl]pyridin-2-amine B (300 mg, 1.26 mmol) and DIPEA (1.10 mL, 6.29 mmol) in toluene (2.5 mL). DMAP (184 mg, 1.51 mmol) was added and the mixture was heated at 90° C. for 24 hours. The reaction mixture was neutralised with 2 M HCl$_{(aq)}$ and extracted with EtOAc (3×5 mL) before the organics were washed with brine, dried over MgSO₄ and the solvent removed in vacuo. The resulting oil was triturated with Et₂O to precipitate a brown solid which was removed by filtration and purified by flash chromatography on silica gel (solvent 20% EtOAc/hexane) to afford the title compound C as a yellow oil (234 mg, 45%).

¹H NMR δ_H (CDCl₃, 300 MHz): 8.60 (br, 1H), 8.04 (d, J=8.0 Hz, 1H), 7.76 (t, J=8.0 Hz, 1H), 7.36-7.22 (m, 6H), 4.67 (s, 2H), 0.89 (s, 9H), 0.06 (s, 6H) ppm. ESI-MS 409.1 [MH]⁺.

2,2-Difluoro-N-[6-(hydroxymethyl)-2-pyridyl]-2-phenoxy-acetamide D

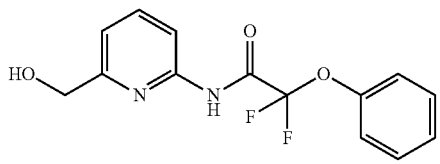 [SMILES: O=C(Nc1cccc(CO)n1)C(F)(F)Oc1ccccc1]

To a solution of N-[6-[(tert-butyl(dimethyl)silyl)oxymethyl]-2-pyridyl]-2,2-difluoro-2-phenoxy-acetamide C (785 mg, 1.92 mmol) in THF (20 mL) was added TBAF [1 M in THF] (2.30 mL, 2.30 mmol) dropwise and the reaction was stirred for 17 hours at room temperature. The reaction mixture was quenched with water (20 mL) and extracted with EtOAc (3×25 mL) before the organics were washed with brine (2×25 mL), dried over MgSO₄ and the solvent removed in vacuo. The crude material was purified by flash chromatography on silica gel (solvent 50% EtOAc/hexane) to afford the title compound D as a white solid (342 mg, 60%).

¹H NMR δ_H (CDCl₃, 300 MHz): 8.86 (br, 1H), 8.10 (d, J=8.0 Hz, 1H), 7.74 (t, J=1.0 Hz, 1H), 7.37-7.32 (m, 2H), 7.26-7.19 (m, 3H), 7.05 (d, J=7.5 Hz, 1H), 4.67 (s, 2H), 3.19 (br, 1H) ppm.

N-(4-(((tert-Butyldimethylsilyl)oxy)methy)thiazol-2-yl)-2,2-difluoro-2-phenoxyacetamide E

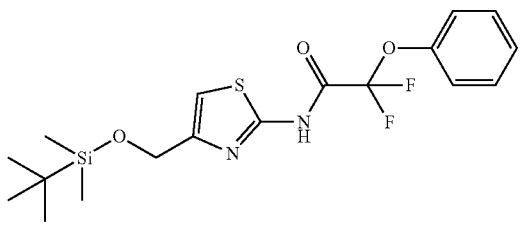 [SMILES: CC(C)(C)[Si](C)(C)OCc1csc(NC(=O)C(F)(F)Oc2ccccc2)n1]

To a solution of 2,2-difluoro-2-phenoxy acetic acid A (658 mg, 3.5 mmol) in DCM (10 mL) and DMF (5 drops) was added oxalyl chloride (0.47 mL, 5.50 mmol) dropwise and the reaction was stirred at room temperature for 2 hours before the volatiles were removed in vacuo. The residue was dissolved in toluene (10 mL) and added to a solution of 4-(((tert-butyldimethylsilyl)oxy)methyl)thiazol-2-amine (610 mg, 2.50 mmol) and DIPEA (2.18 mL, 12.50 mmol) in toluene (10 mL). DMAP (366 mg, 3.00 mmol) was added and the mixture was heated at 90° C. for 19 hours. The reaction mixture was quenched with water (25 mL), neutralised with sat. NH₄Cl_(aq) and extracted with EtOAc (3×25 mL) before the organics were dried over MgSO₄ and the solvent removed in vacuo. The resulting product was purified by flash chromatography on silica gel (solvent 20% EtOAc/hexane) to afford the title compound E as a yellow oil (437 mg, 42%).

¹H NMR δ_H (CDCl₃, 300 MHz): 7.46-7.41 (m, 2H), 7.36-7.33 (m, 1H), 7.29-7.26 (m, 2H), 7.00 (t, J=1.0 Hz, 1H), 4.73 (d, J=1.0 Hz, 2H), 0.94 (s, 9H), 0.13 (s, 6H). ESI-MS 415.5 [MH]+.

2,2-Difluoro-N-(4-(hydroxymethyl)thiazol-2-yl)-2-phenoxyacetamide F

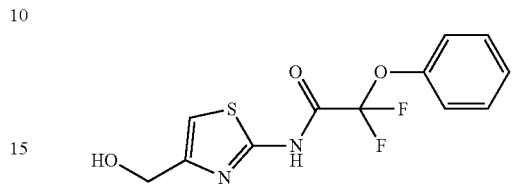

To a solution of N-(4-(((tert-butyldimethylsilyl)oxy)methy)thiazol-2-yl)-2,2-difluoro-2-phenoxyacetamide E (414 mg, 1.00 mmol) in THF (10 mL) was added TBAF [1 M in THF] (1.20 mL, 1.20 mmol) dropwise and the mixture was stirred for 90 minutes at room temperature before further TBAF [1 M in THF] (1.20 mL, 1.20 mmol) was added. After stirring for a further 3 hours the reaction was quenched with water (50 mL) and extracted with EtOAc (3×20 mL) before the organics were washed with brine (50 mL), dried over MgSO₄ and the solvent removed in vacuo. The crude material was purified by flash chromatography on silica gel (solvent EtOAc) to afford the title compound as a colourless oil (290 mg, 97%).

¹H NMR δ_H (CDCl₃, 300 MHz): 7.46-7.41 (m, 2H), 7.38-7.26 (m, 3H), 6.97 (s, 1H), 4.73 (s, 2H) ppm. ESI-MS 300.9 [MH]⁺.

2-Chloro-1-(1H-tetrazol-5-yl)-1H-benzo[d]imidazole G

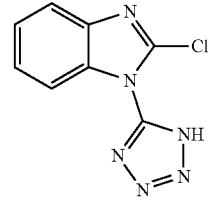 [SMILES: Clc1nc2ccccc2n1-c1nnn[nH]1]

A stirred solution of 2-chloro-1H-benzo[d]imidazole-1-carbonitrile (1.418 g, 7.98 mmol, prepared from commercially available 2-chlorobenzimidazole as described in Chem. Heterocyclic Compounds, 2013, 48(12), 1874) in DMF (15 ml) at 25° C. was treated with ammonium chloride (0.641 g, 11.98 mmol) then sodium azide (0.779 g, 11.98 mmol) and the suspension stirred for 1 h. As a precaution to destroy any excess azide a solution of sodium nitrite (0.331 g, 4.79 mmol) in water (50 mL) was then added, followed by 1N HCl to pH 1 (effervescence) and the product was extracted into EtOAc (100 mL). The organics were washed with water (2×50 mL) and brine then dried (MgSO₄) and concentrated to give an off-white solid, 0.44 g. The aq. layers were treated with more HCl (ensuring pH 1) and the solid collected, washed with water and dried to give 657 mg white solid. The liquors were re-extracted with EtOAc as before and the extracts combined with the earlier extracts to give more off-white solid (0.364 g). The solids were combined to give 2-chloro-1-(1H-tetrazol-5-yl)-1H-benzo[d]imidazole G (1.46 g, 83%, >90% purity by NMR).

¹H NMR (500 MHz, DMSO) δ 7.76 (ddd, J=3.8, 2.3, 0.7 Hz, 1H), 7.62 (ddd, J=4.6, 2.3, 0.7 Hz, 1H), 7.45-7.38 (m, 2H). LCMS (method A): 1.01 min (221, MH⁺)

2-Chloro-1-(1-methyl-1H-tetrazol-5-yl)-1H-benzo[d]imidazole H1 and 2-chloro-1-(2-methyl-2H-tetrazol-5-yl)-1H-benzo[d]imidazole H2

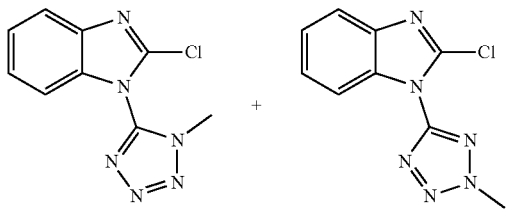 [SMILES: Cn1nnnc1-n1c(Cl)nc2ccccc21 ; Cn1nnc(-n2c(Cl)nc3ccccc32)n1]

A solution of 2-chloro-1-(1H-tetrazol-5-yl)-1H-benzo[d]imidazole G (1.377 g, 6.24 mmol) in DMF (15 ml) was treated with potassium carbonate (1.294 g, 9.36 mmol) and iodomethane (0.971 ml, 15.60 mmol) and stirred at 45° C. for 90 min. The mixture was cooled briefly, treated with 28% aq. NH₃ (10 mL), stirred 5 min then diluted with water (100 mL) and extracted with EtOAc (100 mL). The organic layer was washed with water (2×100 mL) and brine then dried (MgSO₄) and concentrated to give an oil that crystallised upon standing (1.30 g). Chromatography on SiO₂ (50 g Biotage Snap cartridge; dry-loaded on SiO₂ (12 g)) eluting with 0-40% EtOAc/PE gave 2-chloro-1-(2-methyl-2H-tetrazol-5-yl)-1H-benzo[d]imidazole H2 (1.02 g, 70%, less polar), as a white solid, and 2-chloro-1-(1-methyl-1H-tetrazol-5-yl)-1H-benzo[d]imidazole H1 (0.145 g, 8%, more polar) as a white solid, purity approx. 85%, not improved by trituration with Et₂O. 2-chloro-1-(2-methyl-2H-tetrazol-5-yl)-1H-benzo[d]imidazole H2: ¹H NMR (500 MHz, CDCl₃) δ 7.76 (ddd, J=6.2, 3.2, 0.6 Hz, 1H), 7.72 (ddd, J=6.1, 3.3, 0.6 Hz, 1H), 7.39 (d, J=3.2 Hz, 1H), 7.37 (d, J=3.2 Hz, 1H), 4.51 (s, 3H); LCMS (basic, 5 min): 2.52 (235, MH⁺)
2-chloro-1-(1-methyl-1H-tetrazol-5-yl)-1H-benzo[d]imidazole H1: ¹H NMR (500 MHz, CDCl₃) δ 7.86-7.79 (m, 1H), 7.42 (dtd, J=16.7, 7.4, 1.2 Hz, 2H), 7.13 (ddd, J=7.8, 1.3, 0.7 Hz, 1H), 4.04 (s, 3H); LCMS (method A): 2.39 min (235, MH⁺)

In order to (a) confirm the regiochemistry of the thus formed tetrazoles and (b) improve synthetic efficiency, an unambiguous synthesis of 2-chloro-1-(1-methyl-1H-tetrazol-5-yl)-1H-benzo[d]imidazole H1 was developed:

1-(1-Methyl-1H-tetrazol-5-yl)-1,3-dihydro-2H-benzo[d]imidazol-2-one I

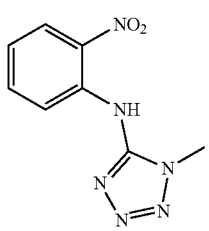 [SMILES: Cn1nnnc1Nc1ccccc1[N+](=O)[O-]]

A stirred, ice-cooled suspension of 5-amino-1-methyltetrazole (5 g, 50.5 mmol) in dry DMF (40 ml) was treated with sodium hydride (60% in mineral oil, 3.03 g, 76 mmol) and stirred a further 15 min then about ⅔ of the 1-fluoro-2-nitrobenzene (5.32 ml, 50.5 mmol) was added dropwise over 15 min so as to maintain the internal temp around 20° C. or lower (did not exceed 25° C.). More sodium hydride (1.110 g, 27.8 mmol) was then added, followed dropwise by the remainder of the fluoronitrobenzene (in DMF, 2 mL) over a further 10 min. The dark red solution was stirred whilst warming to room temperature over 2.5 h then diluted cautiously with water (250 mL) and washed with Et₂O (250 mL). The aq. layer was acidified with 5M aq. HCl (13 mL, to pH 1). The solid was collected, washed with a little water (ca. 2×15 mL) and dried in vacuo to give 1-methyl-N-(2-nitrophenyl)-1H-tetrazol-5-amine 1 (9.29 g, 84%) as a yellow solid.

¹H NMR (500 MHz, CDCl₃) δ 10.59 (s, 1H), 8.76 (dd, J=8.6, 1.2 Hz, 1H), 8.32 (dd, J=8.5, 1.5 Hz, 1H), 7.75 (s, 1H), 7.17 (s, 1H), 4.06 (s, 3H); LCMS (method B): 2.21 min (221, MH⁺).

Following the same procedure as for Synthetic Intermediate ("Int.") I, substituting 1-fluoro-2-nitrobenzene and/or 5-amino-1-methyltetrazole with the required o-fluoronitrobenzene (optionally substituted with $X_n$) and/or aminoheterocycle (Het-NH2), and generally with all of the NaH added at the start of the reaction, there were thus obtained the following intermediates:

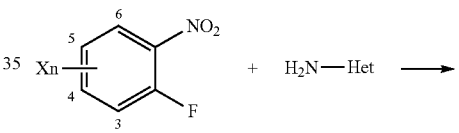

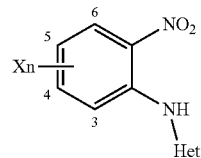

| Int. | $X_n$ | Het-NH2 | Yield | RT<sup>a</sup> | MH⁺ |
|---|---|---|---|---|---|
| I1 | — | 2-amino-3-methylpyridine | 53% | 3.16(B) | 230.1 |
| I2 | — | 5-amino-1-methylpyrazole | 39%<sup>b</sup> | 2.37(B) | 219.1 |
| I3 | — | 5-amino-3,4-dimethylisoxazole | 85%<sup>b</sup> | 2.82(B) | 234.1 |
| I4 | 4-F | 5-amino-1-methyltetrazole | 57% | 2.32(B) | 239.1 |
| I5 | — | 2-aminopyridine | 94%<sup>b</sup> | 2.57(B) | 216.1 |
| I6 | — | 5-amino-3-methylisothiazole | 68% | 2.80(B) | 236.1 |
| I7 | — | 3-aminoisoxazole | 85% | 2.74(B) | 206.1 |

<sup>a</sup>RT = LCMS retention time in minutes using indicated Method (A-D);
<sup>b</sup>Product obtained using an aqueous work-up, extracting with EtOAc, followed by chromatography on silica eluting with 0-50% EtOAc/PE.

N1-(1-Methyl-1H-tetrazol-5-yl)benzene-1,2-diamine
J

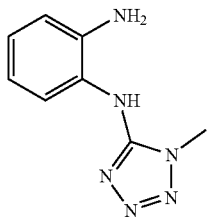

A stirred suspension of 1-methyl-N-(2-nitrophenyl)-1H-tetrazol-5-amine 1 (2.46 g, 11.17 mmol) in ethanol (80 ml) under $N_2$ was treated with 10% palladium on activated charcoal (0.1 g, 11.17 mmol) then ammonium formate (2.82 g, 44.7 mmol) and the mixture was heated under reflux for 6 h then cooled and filtered through Celite under $N_2$. The filter was washed with EtOAc and the combined filtrates were concentrated in vacuo to give crude product, 1.77 g, as a reddish solid. This material was loaded onto $SiO_2$ (5 g) and chromatographed on silica (24 g Puriflash) eluting with 0-10% MeOH/DCM to give N1-(1-methyl-1H-tetrazol-5-yl)benzene-1,2-diamine J (1.3 g, 61%), as a red solid.

$^1$H NMR (500 MHz, DMSO) δ 8.15 (s, 1H), 7.19 (dd, J=7.8, 1.5 Hz, 1H), 6.96-6.89 (m, 1H), 6.74 (dd, J=8.0, 1.4 Hz, 1H), 6.56 (td, J=7.7, 1.5 Hz, 1H), 5.05 (s, 2H), 3.84 (s, 3H); LCMS (method A): 1.38 min (191, MH$^+$).

Following the same procedure as for Synthetic Intermediate ("Int.") J, substituting the nitroaryl starting material ("SM") I with the required nitroaryl, there were thus obtained the following aniline intermediates:

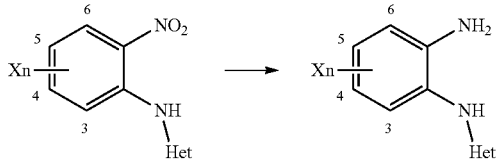

| SM | $X_n$ | Het | Aniline | Yield | RT$^a$ | MH$^+$ |
|---|---|---|---|---|---|---|
| I1 | — | 2-(3-methyl)pyridyl | J1 $^b$ | 100% | 0.94(B) | 200.1 |
| I2 | — | 1-methylpyrazol-5-yl | J2 | 85% | 1.20(B) | 189.1 |
| I4 | 4-F | 1-methyltetrazol-5-yl | J4 $^b$ | 100% | 1.12(B) | 209.1 |
| I5 | — | 2-pyridyl | J5 $^b$ | 100% | 0.96(B) | 186.2 |

$^a$RT = LCMS retention time in minutes using indicated Method (A-D);

$^b$ Product used directly in next step without need for chromatographic purification.

N1-(3,4-Dimethylisoxazol-5-yl)benzene-1,2-diamine
J3

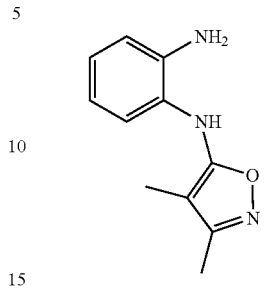

Sodium hydrogen carbonate (209 mg, 2.487 mmol) then sodium hydrosulfite (649 mg, 3.73 mmol) were added to a stirred solution of 3,4-dimethyl-N-(2-nitrophenyl)isoxazol-5-amine 13 (290 mg, 1.243 mmol) in THF (3 mL) and water (1.5 mL). The reaction mixture was stirred at 60° C. for 22 h then quenched with water (5 mL) and extracted into EtOAc (2×10 mL). The combined organics were washed with brine, dried (MgSO$_4$) and chromatographed on silica (10 g Biotage Snap KP-Sil column) eluting with 0-5% MeOH/DCM to give N1-(3,4-dimethylisoxazol-5-yl)benzene-1,2-diamine J3 (160 mg, 63%) as an orange solid.

$^1$H NMR (500 MHz, CDCl$_3$) δ 7.04 (dd, J=7.9, 1.2 Hz, 1H), 6.97 (td, J=7.7, 1.4 Hz, 1H), 6.85-6.79 (m, 2H), 5.76 (s, 1H), 2.16 (s, 3H), 1.65 (s, 3H); LCMS (method B): 1.78 min (204.2, MH$^+$).

N1-(3-Methylisothiazol-5-yl)benzene-1,2-diamine
J6

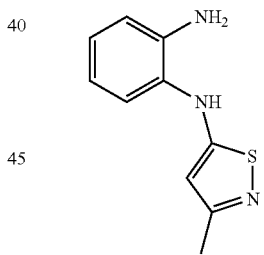

A mixture of zinc powder (556 mg, 8.50 mmol) with aqueous HCl (1M, 4 mL) was stirred for 10 min. then filtered, washed to neutrality with water then PE and dried under reduced pressure (10 min.). A mixture of 3-methyl-N-(2-nitrophenyl)isothiazol-5-amine 16 (200 mg, 0.85 mmol) and the activated zinc (556 mg, 8.50 mmol) in acetic acid (8 mL) was stirred at room temperature for 2 h. The mixture was diluted with DCM and filtered through diatomaceous earth. The filtrates were washed with saturated aq. NaHCO$_3$ and brine, dried (MgSO$_4$) and concentrated to give N1-(3-methylisothiazol-5-yl)benzene-1,2-diamine J6 (180 mg, 100%) as a dark red viscous oil, pure enough for use directly in the next step.

$^1$H NMR (500 MHz, CDCl$_3$) δ 7.25-7.22 (m, 1H), 7.04 (dd, J=7.7, 1.3 Hz, 1H), 6.82 (t, J=7.3 Hz, 2H), 6.21 (s, 1H), 2.33 (s, 3H); LCMS (method B): 1.81 min (206.1, MH$^+$).

N1-(Isoxazol-3-yl)benzene-1,2-diamine J7

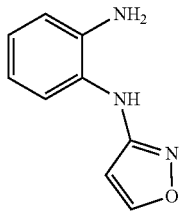 [SMILES: Nc1ccccc1Nc1ccon1]

Using the same procedure as for J3, except that the reaction time was 4 h at 60° C., N-(2-nitrophenyl)isoxazol-3-amine 17 was used as starting material instead of 13, and the product was purified by chromatography eluting with 0-100% EtOAc/PE, there was thus obtained N1-(isoxazol-3-yl)benzene-1,2-diamine J7 (31% yield) as an orange solid.

$^{1}$H NMR (500 MHz, CDCl$_3$) δ 8.12 (d, J=1.6 Hz, 1H), 7.28-7.25 (m, 1H), 7.03-6.98 (m, 1H), 6.84-6.76 (m, 2H), 6.05 (s, J=17.8 Hz, 1H), 5.99 (d, J=1.8 Hz, 1H). LCMS (method B): 1.21 min (176.2, MH$^+$).

1-(1-Methyl-1H-tetrazol-5-yl)-1,3-dihydro-2H-benzo[d]imidazol-2-one K

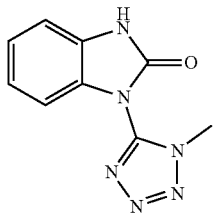 [SMILES: Cn1nnnc1-n1c(=O)[nH]c2ccccc21]

A partial solution of N$^1$-(1-methyl-1H-tetrazol-5-yl)benzene-1,2-diamine J (714 mg, 3.75 mmol) in dry THF (20 mL) was treated with N,N'-carbonyldiimidazole (791 mg, 4.88 mmol) at RT and stirred for 90 min. The resultant solution was then diluted gradually with water (100 mL) and stirred another 30 min with ice cooling. The solid was collected, washed with water (4×5 mL) and dried in vacuo to give 1-(1-methyl-1H-tetrazol-5-yl)-1,3-dihydro-2H-benzo[d]imidazol-2-one K (750 mg, 92%), as a pale pink solid.

$^{1}$H NMR (500 MHz, DMSO) δ 11.69 (s, 1H), 7.23-7.08 (m, 4H), 4.10 (s, 3H); LCMS (method B) 1.52 min (217, MH$^+$).

1-(3-Methylpyridin-2-yl)-1,3-dihydro-2H-benzo[d]imidazol-2-one K1

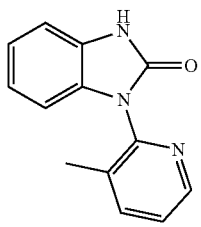 [SMILES: Cc1cccnc1-n1c(=O)[nH]c2ccccc21]

A solution of N$^1$-(3-methylpyridin-2-yl)benzene-1,2-diamine (249 mg, 1.25 mmol) in dry THF (5 mL) was treated with N,N'-carbonyldiimidazole (243 mg, 1.50 mmol) and stirred at room temperature under nitrogen for 2 h. The reaction mixture was diluted with MeOH (1 mL), loaded onto SiO$_2$ (2 g) and chromatographed on SiO$_2$ (10 g Biotage KP-Sil cartridge) eluting with 40-100% EtOAc/Heptane to give 1-(3-methylpyridin-2-yl)-1,3-dihydro-2H-benzo[d]imidazol-2-one K1 (173 mg, 62%) as a gum.

$^{1}$H NMR (500 MHz, CDCl$_3$) δ 10.27 (s, 1H), 8.55-8.50 (m, 1H), 7.79 (ddd, J=7.6, 1.7, 0.7 Hz, 1H), 7.36 (dd, J=7.7, 4.7 Hz, 1H), 7.12-7.10 (m, 1H), 7.08 (td, J=7.5, 1.2 Hz, 1H), 7.03 (td, J=7.5, 1.6 Hz, 1H), 6.86 (d, J=7.5 Hz, 1H), 2.35 (s, 3H); LCMS (method B) 1.98 min (226.1, MH$^+$).

2-Chloro-1-(1-methyl-1H-tetrazol-5-yl)-1H-benzo[d]imidazole H1

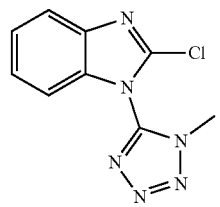 [SMILES: Cn1nnnc1-n1c(Cl)nc2ccccc21]

A stirred mixture of 1-(1-methyl-1H-tetrazol-5-yl)-1,3-dihydro-2H-benzo[d]imidazol-2-one K (24 mg, 0.111 mmol) and phosphorus(V) oxychloride (1 ml, 10.70 mmol) was treated with phosphorus pentachloride (34 mg, 0.163 mmol) and heated under N$_2$ for 1 h then cooled briefly, treated with N,N-diethylaniline (18 μL, 0.113 mmol) and heated under reflux a further 4 h. The mixture was cooled, poured onto ice and neutralised with saturated sodium hydrogen carbonate solution then extracted with EtOAc. The organic layer was washed with water and brine, dried (MgSO$_4$) and concentrated to give crude product (51 mg) which was loaded onto SiO$_2$ and chromatographed on SiO$_2$ (12 g) eluting with 50-100% EtOAc/PE to give 2-chloro-1-(1-methyl-1H-tetrazol-5-yl)-1H-benzo[d]imidazole H1 (11 mg, 0.028 mmol, 25% yield at purity 60%), contaminated with starting material. NMR and LCMS confirm identity of required product from when produced from intermediate G.

$^{1}$H NMR (500 MHz, CDCl$_3$) δ 7.82 (ddd, J=8.0, 1.3, 0.7 Hz, 1H), 7.44 (td, J=7.7, 1.4 Hz, 1H), 7.42-7.38 (m, 1H), 7.13 (ddd, J=7.8, 1.3, 0.7 Hz, 1H), 4.04 (s, 3H), +signals for starting material; LCMS (method A): 2.32 min (60%, 235 & 237, MH$^+$) and 1.58 min (34%, 217, MH$^+$ for starting material).

2-Chloro-1-(3-methylpyridin-2-yl)-1H-benzo[d]imidazole H3

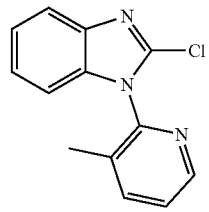 [SMILES: Cc1cccnc1-n1c(Cl)nc2ccccc21]

A mixture of 1-(3-methylpyridin-2-yl)-1,3-dihydro-2H-benzo[d]imidazol-2-one K1 (451 mg, 2.00 mmol) and sodium carbonate (318 mg, 3.00 mmol) in phosphorus(V) oxychloride (2.5 mL, 26.8 mmol) was stirred at 100° C. for 7 h. The mixture was cooled, concentrated, partitioned between saturated aq. NaHCO₃ (25 mL) and EtOAc (30 mL). The organics were washed with water (25 mL) and brine, dried (MgSO₄) and chromatographed on silica (12 g Puriflash cartridge) eluting with 30-100% EtOAc/PE to give 2-chloro-1-(3-methylpyridin-2-yl)-1H-benzo[d]imidazole H3 (114 mg, 23%) as a gum.

¹H NMR (500 MHz, CDCl₃) δ 8.57 (ddd, J=4.7, 1.8, 0.5 Hz, 1H), 7.84 (ddd, J=7.7, 1.8, 0.7 Hz, 1H), 7.80-7.74 (m, 1H), 7.47 (dd, J=7.7, 4.7 Hz, 1H), 7.35-7.29 (m, 1H), 7.26 (td, J=7.7, 1.2 Hz, 1H), 7.00-6.95 (m, 1H), 2.14 (s, 3H); LCMS (method B) 2.14 min (244.1, MH⁺).

N,N-bis(t-Butyloxycarbonyl)-6-[(t-butyl(dimethyl)silyl)oxymethyl]pyridin-2-amine L

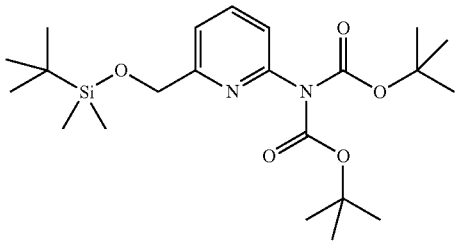 [SMILES: CC(C)(C)OC(=O)N(C(=O)OC(C)(C)C)c1cccc(CO[Si](C)(C)C(C)(C)C)n1]

4-(Dimethylamino)pyridine (0.031 g, 0.252 mmol) and di-tert-butyl dicarbonate (5.78 ml, 25.2 mmol) were added to a solution of 6-[(tert-butyl(dimethyl)silyl)oxymethyl]pyridin-2-amine B (3 g, 12.58 mmol) in DCM (30 ml) and the reaction mixture was stirred at RT for 18 h then diluted with DCM (100 mL), washed with water (100 mL) and brine (100 mL), dried (MgSO₄) and concentrated to give a dark yellow oil. Chromatography on silica eluting with 7-20% EtOAc/PE gave N,N-bis(t-butyloxycarbonyl)-6-[(t-butyl(dimethyl)silyl)oxymethyl]pyridin-2-amine L (3.22 g, 58%) as a viscous oil.

¹H NMR (500 MHz, CDCl₃) δ 7.74 (t, J=7.8 Hz, 1H), 7.43 (d, J=7.7 Hz, 1H), 7.08 (d, J=7.9 Hz, 1H), 4.79 (s, 2H), 1.43 (s, 18H), 0.95 (s, 9H), 0.11 (s, 6H); LCMS (method A) 3.38 min (239, [M-2CO₂ᵗBu+H]⁺).

N,N-bis(t-Butyloxycarbonyl)-6-hydroxymethyl]pyridin-2-amine M

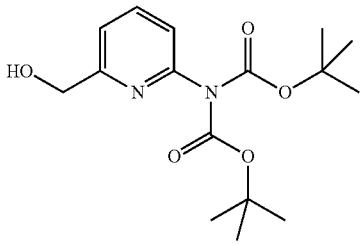 [SMILES: CC(C)(C)OC(=O)N(C(=O)OC(C)(C)C)c1cccc(CO)n1]

Tetrabutylammonium fluoride (1M in THF) (10.44 ml, 10.44 mmol) was added to a solution of N,N-bis(t-butyloxycarbonyl)-6-[(t-butyl(dimethyl)silyl)oxymethyl]pyridin-2-amine L (3.21 g, 7.33 mmol) in dry THF (50 ml) at 0° C. The reaction mixture was stirred at 0° C. for 4 h then diluted with ethyl acetate (100 mL), washed with water (100 mL) and brine, dried (MgSO₄), concentrated and triturated with PE to give N,N-bis(t-butyloxycarbonyl)-6-hydroxymethyl]pyridin-2-amine M (1.33 g, 56%) as a solid.

¹H NMR (500 MHz, CDCl₃) δ7.73 (t, J=7.8 Hz, 1H), 7.19 (d, J=7.9 Hz, 1H), 7.15 (d, J=7.6 Hz, 1H), 4.73 (s, 2H), 1.45 (s, 18H); LCMS (method A): 2.66 min (325, MH⁺).

tert-Butyl (6-(hydroxymethyl)pyridin-2-yl)carbamate N

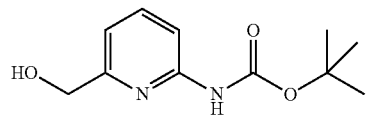 [SMILES: CC(C)(C)OC(=O)Nc1cccc(CO)n1]

A solution of N,N-bis(t-butyloxycarbonyl)-6-hydroxymethyl]pyridin-2-amine M (50 mg, 0.154 mmol) in THF (10 mL) was treated with a solution of lithium hydroxide monohydrate (12.9 mg, 0.31 mmol) in water (2.5 mL) and the reaction mixture was stirred at room temperature for 2.5 h then at 50° C. for 3 h. More lithium hydroxide monohydrate (6.5 mg) was added and the reaction mixture was stirred at 50° C. overnight. The reaction mixture was treated with saturated aqueous ammonium chloride, diluted with ethyl acetate (20 mL), washed with water (3×20 mL) and brine (20 mL), dried (MgSO₄) and chromatographed on silica eluting with 5-75% EtOAc/PE to give tert-butyl (6-(hydroxymethyl)pyridin-2-yl)carbamate N (25 mg, 72.3%) as a colourless, viscous oil.

¹H NMR (500 MHz, CDCl₃) δ 7.81 (d, J=8.3 Hz, 1H), 7.67-7.61 (m, 1H), 7.34 (s, 1H), 6.89 (d, J=7.4 Hz, 1H), 4.64 (s, 2H), 1.52 (s, 9H); LCMS (method A): 2.25 min (247.1, [M+Na]⁺).

1-(1-Methyl-1H-pyrazol-5-yl)-1H-benzo[d]imidazole O

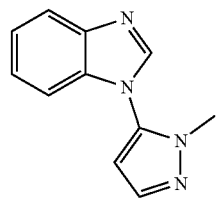

A suspension of N¹-(1-methyl-1H-pyrazol-5-yl)benzene-1,2-diamine J2 (170 mg, 0.903 mmol) in trimethylorthoformate (3.05 mL, 27.9 mmol) was treated with conc. hydrochloric acid (3.76 µL, 0.045 mmol) and stirred with heating under reflux for 2 h. The reaction mixture was allowed to cool, concentrated and chromatographed on silica (25 g Biotage Snap KP-Sil column) eluting with 0-4% MeOH/DCM to give 1-(1-methyl-1H-pyrazol-5-yl)-1H-benzo[d]imidazole O (164 mg, 92%) as a pale green solid.

¹H NMR (500 MHz, CDCl₃) δ 7.97 (s, 1H), 7.95-7.84 (m, 1H), 7.66 (d, J=2.0 Hz, 1H), 7.43-7.33 (m, 2H), 7.25-7.19 (m, 1H), 6.43 (d, J=2.0 Hz, 1H), 3.68 (s, 3H); LCMS (method B): 1.68 min (199.2, MH⁺)

2-Chloro-1-(1-methyl-1H-pyrazol-5-yl)-1H-benzo[d]imidazole P

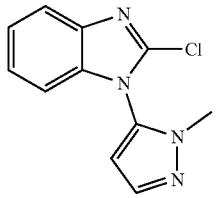 [SMILES: Cn1nccc1-n1c(Cl)nc2ccccc21]

Lithium diisopropylamide (1M solution in THF, 0.757 ml, 0.757 mmol) was added dropwise with stirring to a solution of 1-(1-methyl-1H-pyrazol-5-yl)-1H-benzo[d]imidazole O (100 mg, 0.504 mmol) in dry THF (1.5 mL) at −78° C. under nitrogen. After 1.5 h N-chlorosuccinimide (202 mg, 1.51 mmol) was then added at −78° C. and stirring was continued whilst warming to room temperature over 18 h. Saturated aq. ammonium chloride solution was added and the mixture extracted with DCM. The organic extracts were washed with brine, dried (MgSO$_4$) and chromatographed on silica (10 g Biotage snap KP Sil column) eluting with 0-100% EtOAc/PE to give 2-chloro-1-(1-methyl-1H-pyrazol-5-yl)-1H-benzo[d]imidazole P (45 mg, 38%) as a pale yellow solid.

$^1$H NMR (500 MHz, CDCl$_3$) δ 7.77 (dd, J=7.4, 0.8 Hz, 1H), 7.69 (d, J=2.0 Hz, 1H), 7.34 (dtd, J=16.6, 7.4, 1.2 Hz, 2H), 7.06 (dd, J=7.3, 1.0 Hz, 1H), 6.46 (d, J=2.0 Hz, 1H), 3.65 (s, 3H); LCMS (method B): 2.23 min (233.1, MH$^+$).

1-(1-Methyl-H-tetrazol-5-yl)-1,3-dihydro-2H-benzo[d]imidazole-2-thione Q

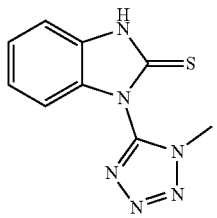

A suspension of N$^1$-(1-methyl-1H-tetrazol-5-yl)benzene-1,2-diamine J (923 mg, 4.85 mmol) in dry THF (25 ml) was treated with thiocarbonyldiimidazole ("TCDI", 1.30 g, 7.29 mmol), stirred under nitrogen at room temperature for 75 min. then diluted with water (100 mL) and cooled with ice/water. The solid was collected, washed with water and dried in vacuo to give 1-(1-methyl-1H-tetrazol-5-yl)-1,3-dihydro-2H-benzo[d]imidazole-2-thione Q (962 mg, 85%) as a pale pink solid.

$^1$H NMR (500 MHz, DMSO) δ 13.66 (s, 1H), 7.36-7.29 (m, 2H), 7.29-7.20 (m, 1H), 7.10 (d, J=8.0 Hz, 1H), 4.08 (s, 3H); LCMS (method B) 1.96 min (233.1, MH$^+$).

Following the same procedure as for Synthetic Intermediate Q, with the appropriate aniline starting material in place of N$^1$-(1-methyl-1H-tetrazol-5-yl)benzene-1,2-diamine J, except that an extractive work-up followed by chromatography on silica was carried out if a solid was not obtained upon dilution with water, there were thus obtained the following intermediates:

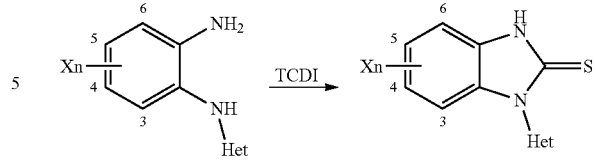

| Int. | X$_n$ | Het- | SM | Yield | RT$^a$ | MH$^+$ |
|---|---|---|---|---|---|---|
| Q1 | — | 3,4-dimethylisoxazol-5-yl- | J3 | 100%$^b$ | 2.33(B) | 246.1 |
| Q2 | 4-F | 1-methyltetrazol-5-yl- | J4 | 55%$^b$ | 2.13(B) | 251.1 |
| Q3 | — | 2-pyridyl- | J5 | 47%$^b$ | 1.99(B) | 228.1 |
| Q4 | — | 3-methylisothiazol-5-yl- | J6 | 72%$^b$ | 2.43(B) | 248.1 |
| Q5 | — | isoxazol-3-yl | J7 | 74%$^b$ | 2.31(B) | 218.0 |

$^a$RT = LCMS retention time in minutes using indicated Method (A-D);
$^b$Extractive work-up followed by chromatography.

1-(1-Methyl-1H-tetrazol-5-yl)-2-(methylthio)-1H-benzo[d]imidazole R

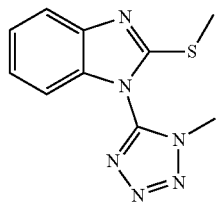 [SMILES: CSc1nc2ccccc2n1-c1nnnn1C]

A solution of 1-(1-methyl-1H-tetrazol-5-yl)-1,3-dihydro-2H-benzo[d]imidazole-2-thione Q (373 mg, 1.606 mmol) in dry DMF (3 mL) was treated with iodomethane (0.113 mL, 1.82 mmol) then caesium carbonate (740 mg, 2.271 mmol) and the mixture was stirred at ambient temperature under nitrogen for 40 min. The solution was diluted with water (20 mL) and extracted with EtOAc (25 mL). The organics were washed further with water (2×25 mL) and brine, dried (MgSO$_4$) and chromatographed on silica (25 g Biotage KP-Sil cartridge) eluting with 0-1% MeOH/DCM to give 1-(1-methyl-1H-tetrazol-5-yl)-2-(methylthio)-1H-benzo[d]imidazole R (341 mg, 86%) as a red solid, essentially pure by NMR.

$^1$H NMR (500 MHz, CDCl$_3$) δ 7.75 (d, J=8.0 Hz, 1H), 7.39-7.32 (m, 1H), 7.30-7.21 (m, 1H), 7.04 (d, J=8.0 Hz, 1H), 3.98 (s, 3H), 2.81 (s, 3H); LCMS (method B) 2.35 min (247.1, MH$^+$)

Following the same procedure as for Synthetic Intermediate R, with the appropriate starting material in place of 1-(1-methyl-H-tetrazol-5-yl)-1,3-dihydro-2H-benzo[d]imidazole-2-thione Q, there were thus obtained the following intermediates:

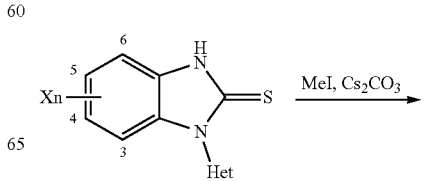

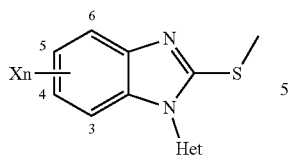

| Int. | $X_n$ | Het- | SM | Yield | RT[a] | MH+ |
|---|---|---|---|---|---|---|
| R1 | — | 3,4-dimethylisoxazol-5-yl- | Q1 | 69%[b] | 2.78(B) | 260.2 |
| R2 | 4-F | 1-methyltetrazol-5-yl- | Q2 | 59%[b] | 2.36(B) | 265.1 |
| R3 | — | 2-pyridyl- | Q3 | 70%[b,c] | 2.35(B) | 244.2 |
| R4 | — | 3-methylisothiazol-5-yl- | Q4 | 59%[c,d] | 2.86(B) | 262.1 |
| R5 | — | isoxazol-3-yl | Q5 | 99% | 2.53(B) | 232.1 |

[a]RT = LCMS retention time in minutes using indicated Method (A-D);
[b]Eluent for chromatography was 0-100% EtOAc/PE.;
[c]Contains DMF but used directly in next step;
[d]No chromatographic purification required.

1-(1-Methyl-1H-tetrazol-5-yl)-2-(methylsulfonyl)-1H-benzo[d]imidazole S

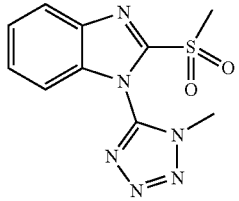 [SMILES: Cn1nnnc1-n1c(S(C)(=O)=O)nc2ccccc21]

A solution of 1-(1-methyl-1H-tetrazol-5-yl)-2-(methylthio)-1H-benzo[d]imidazole R (464 mg, 1.88 mmol) in DCM (12 mL) was treated with 3-chloroperoxybenzoic acid (75% strength, 1.04 g, 4.52 mmol) and stirred at room temperature for 4.5 h. The reaction mixture was diluted with DCM (100 mL), washed with saturated aq. NaHCO₃ solution (2×100 mL) and brine, dried (MgSO₄) and concentrated to give a colourless gum, crystallising (721 mg). Chromatography on silica (12 g Puriflash cartridge) eluting with 0-40% EtOAc/PE gave 1-(1-methyl-1H-tetrazol-5-yl)-2-(methylsulfonyl)-1H-benzo[d]imidazole S (467 mg, 89%) as a colourless solid.

¹H NMR (500 MHz, CDCl₃) δ 8.04 (ddd, J=4.1, 2.9, 0.7 Hz, 1H), 7.65-7.50 (m, 2H), 7.15 (ddd, J=4.9, 2.9, 0.7 Hz, 1H), 4.00 (s, 3H), 3.43 (s, 3H); LCMS (method B): 2.07 min (279.1, MH+).

Following the same procedure as for Synthetic Intermediate S, with the appropriate starting material in place of 1-(1-methyl-1H-tetrazol-5-yl)-2-(methylthio)-1H-benzo[d]imidazole R, there were thus obtained the following intermediates:

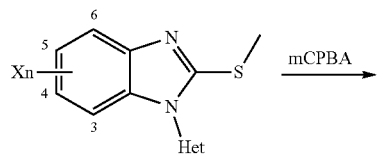

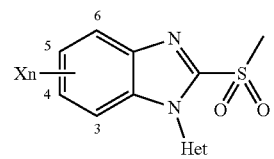

| Int. | $X_n$ | Het- | SM | Yield | RT[a] | MH+ |
|---|---|---|---|---|---|---|
| S1 | — | 3,4-dimethylisoxazol-5-yl- | R1 | 86% | 2.33(B) | 292.1 |
| S2 | 4-F | 1-methyltetrazol-5-yl- | R2 | 76% | 2.25(B) | 297.1 |
| S3 | — | 2-pyridyl- | R3 | 71% | 2.13(B) | 274.2 |
| S4 | — | 3-methylisothiazol-5-yl- | R4 | 39% | 2.40(B) | 294.1 |
| S5 | — | isoxazol-3-yl | R5 | 52% | 2.25(B) | 264.1 |

[a]RT = LCMS retention time in minutes using indicated Method (A-D).

6-(((1-(1-Methyl-1H-tetrazol-5-yl)-1H-benzo[d]imidazol-2-yl)oxy)methyl)pyridin-2-amine T

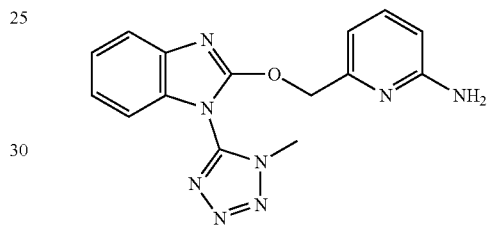

A solution of (6-aminopyridin-2-yl)methanol (72.8 mg, 0.586 mmol) in dry DMF (3 mL) was treated with sodium hydride (23.5 mg, 0.586 mmol) and the mixture was stirred at 0° C. for 5 min. A solution of 1-(1-methyl-1H-tetrazol-5-yl)-2-(methylsulfonyl)-1H-benzo[d]imidazole S (136 mg, 0.489 mmol) in dry DMF (3 ml) was added and stirring was continued for 45 min. at 0° C. The mixture was treated with saturated aq. ammonium chloride solution (2 mL, to pH 7), diluted with EtOAc (50 mL), washed with water (3×50 mL) and brine, dried (MgSO₄) and chromatographed on silica (12 g Puriflash column) eluting with 0-5% MeOH/DCM) to give 6-(((1-(1-methyl-1H-tetrazol-5-yl)-1H-benzo[d]imidazol-2-yl)oxy)methyl)pyridin-2-amine T (114 mg, 72%) as a white solid.

¹H NMR (500 MHz, CDCl₃) δ 7.61 (d, J=7.9 Hz, 1H), 7.45-7.39 (m, 1H), 7.33-7.29 (m, 2H), 7.27-7.22 (m, 1H), 6.72 (d, J=7.2 Hz, 1H), 6.47 (d, J=8.2 Hz, 1H), 5.53 (s, 2H), 4.64 (s, 2H), 4.06 (s, 3H); LCMS (method A): 2.31 min (323.2, MH+).

2,2-Difluoro-2-(4-fluorophenoxy)acetic acid A1

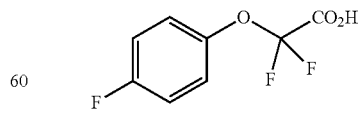

Following the same procedure as for intermediate A except that 4-fluorophenol was used as starting material instead of phenol, there was thus obtained 2,2-difluoro-2-(4-fluorophenoxy)acetic acid A1 (290 mg, 61%) as a dark yellow oil.

¹H NMR (500 MHz, CDCl₃) δ 7.21 (dd, J=9.0, 4.4 Hz, 2H), 7.10-7.02 (m, 2H); LCMS (method B): 1.33 min (205.2, (M-H)⁻).

N-(6-(((tert-Butyldimethylsilyl)oxy)methyl)pyridin-2-yl)-2-phenoxyacetamide C1

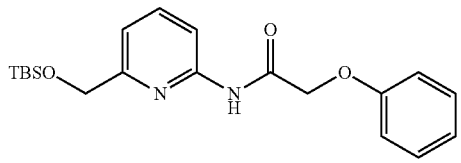 [SMILES: CC(C)(C)[Si](C)(C)OCc1cccc(NC(=O)COc2ccccc2)n1]

Phenoxyacetyl chloride (0.58 mL, 4.2 mmol) was added to a stirred solution of 6-(((tert-butyldimethylsilyl)oxy)methyl)pyridin-2-amine B (1.0 g, 5.0 mmol) and triethylamine (0.59 mL, 4.2 mmol) in DCM (15 mL). After 2 h the reaction mixture was concentrated in vacuo and the residue was chromatographed on silica (25 g Biotage KP-Sil cartridge) eluting with 10-60% EtOAc/PE to give N-(6-(((tert-butyldimethylsilyl)oxy)methyl)pyridin-2-yl)-2-phenoxyacetamide C₁ (1.5 g, 98%) as a colourless oil.

¹H NMR (500 MHz, CDCl₃) δ 8.83 (s, 1H), 8.13 (d, J=8.2 Hz, 1H), 7.75 (t, J=7.9 Hz, 1H), 7.35 (t, J=8.0 Hz, 2H), 7.29 (d, J=7.6 Hz, 1H), 7.05 (t, J=7.4 Hz, 1H), 7.01 (d, J=8.0 Hz, 2H), 4.73 (s, 2H), 4.62 (s, 2H), 0.96 (s, 9H), 0.12 (s, 6H); LCMS (method A): 4.23 min (374.6, MH⁺).

N-[6-[(tert-Butyl(dimethyl)silyl)oxymethyl]-2-pyridyl]-2,2-difluoro-2-phenoxy-acetamide C (Alternative Procedure)

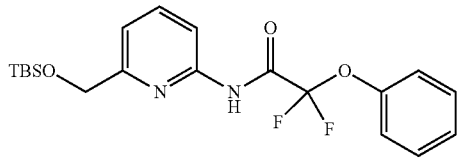 [SMILES: CC(C)(C)[Si](C)(C)OCc1cccc(NC(=O)C(F)(F)Oc2ccccc2)n1]

HATU (4.78 g, 12.6 mmol) was added to a stirred solution of 6-[(tert-butyl(dimethyl)silyl)oxymethyl]pyridin-2-amine B (2 g, 8.39 mmol) and 2,2-difluoro-2-phenoxyacetic acid A (1.99 g, 10.6 mmol) in DMF (4 mL) and N,N-diisopropylethylamine (5.85 mL, 33.6 mmol). The mixture was stirred at 50° C. for 16 hours then was diluted with water and extracted with ethyl acetate (3×50 mL). The organic extracts were combined, washed with water (3×50 mL) and brine (50 mL), dried (MgSO₄) and chromatographed on silica (25 g Biotage KP Sil cartridge) eluting with 0-20% EtOAc/PE to give the N-[6-[(tert-butyl(dimethyl)silyl)oxymethyl]-2-pyridyl]-2,2-difluoro-2-phenoxy-acetamide C (3.17 g, 92%) as a yellow oil.

N-(6-(((tert-Butyldimethylsilyl)oxy)methyl)pyridin-2-yl)-2,2-difluoro-2-(4-fluorophenoxy)acetamide C2

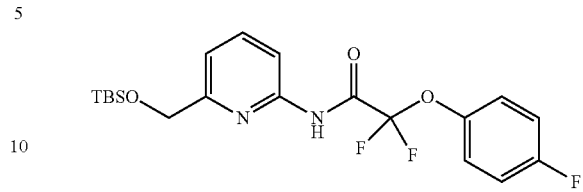

Following the Alternative Procedure for the synthesis of intermediate C, using 2,2-difluoro-2-(4-fluorophenoxy)acetic acid A1 as starting material in place of A, there was thus obtained N-(6-(((tert-butyldimethylsilyl)oxy)methyl)pyridin-2-yl)-2,2-difluoro-2-(4-fluorophenoxy)acetamide C₂ (461 mg, 92%) as a yellow oil.

¹H NMR (500 MHz, CDCl₃) δ 8.68 (s, 1H), 8.10 (d, J=8.2 Hz, 1H), 7.81 (t, J=7.9 Hz, 1H), 7.37 (d, J=7.7 Hz, 1H), 7.24 (dd, J=9.1, 4.4 Hz, 2H), 7.08 (dd, J=9.0, 8.0 Hz, 2H), 4.74 (s, 2H), 0.96 (s, 9H), 0.12 (s, 6H); LCMS (method A): 4.40 min (427.3, MH⁺).

N-(6-(Hydroxymethyl)pyridin-2-yl)-2-phenoxyacetamide D1

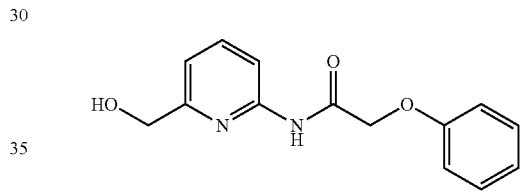

A solution of tetrabutylammonium fluoride [1M in THF] (4.1 ml, 4.1 mmol) was added to a stirred solution of N-(6-(((tert-butyldimethylsilyl)oxy)methyl)pyridin-2-yl)-2-phenoxyacetamide C1 (1.5 g, 4.1 mmol) in THF (20 mL) and the mixture was stirred for 1 h then quenched with a saturated aq. solution of NH₄Cl (40 mL) and extracted with EtOAc (2×40 mL). The organic layers were dried (MgSO₄) then chromatographed on silica (12 g Biotage Kp-Sil cartridge) eluting with 40-100% EtOAc/PE to give N-(6-(hydroxymethyl)pyridin-2-yl)-2-phenoxyacetamide D1 (530 mg, 50%) as a white solid.

¹H NMR (500 MHz, CDCl₃) δ 8.91 (s, 1H), 8.19 (d, J=8.2 Hz, 1H), 7.75 (t, J=7.9 Hz, 1H), 7.36 (t, J=8.0 Hz, 2H), 7.10-6.99 (m, 4H), 4.71 (s, 2H), 4.65 (s, 2H), 3.24 (s, 1H); LCMS (method B): 1.91 min. (260.1, MH⁺).

2,2-Difluoro-2-(4-fluorophenoxy)-N-(6-(hydroxymethyl)pyridin-2-yl)acetamide D2

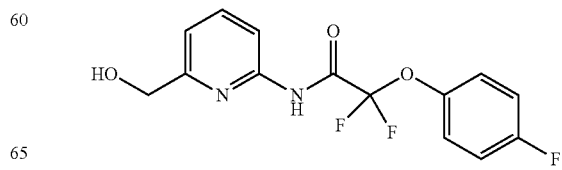

Following the same procedure as for intermediate D, except that the reaction mixture was stirred at 0° C. for 3 hours and the product was purified trituration with PE, there was thus obtained 2,2-difluoro-2-(4-fluorophenoxy)-N-(6-(hydroxymethyl)pyridin-2-yl)acetamide D2 (248 mg, 74%) as a white solid.

$^1$H NMR (500 MHz, CDCl$_3$) $^1$H NMR (500 MHz, CDCl$_3$) δ 8.77 (s, 1H), 8.15 (d, J=8.2 Hz, 1H), 7.80 (t, J=7.9 Hz, 1H), 7.28-7.25 (m, 2H), 7.14 (d, J=7.6 Hz, 1H), 7.10 (dd, J=9.1, 8.0 Hz, 2H), 4.74 (s, 2H); LCMS (method A): 2.65 min (313.1, MH$^+$).

Following the same procedure as for Synthetic Intermediate ("Int.") I, substituting 1-fluoro-2-nitrobenzene and/or 5-amino-1-methyltetrazole with the required o-fluoronitrobenzene (optionally substituted with X$_n$) and/or aminoheterocycle (Het-NH$_2$), and generally with all of the NaH added at the start of the reaction, there were thus obtained the following intermediates I8-I12:

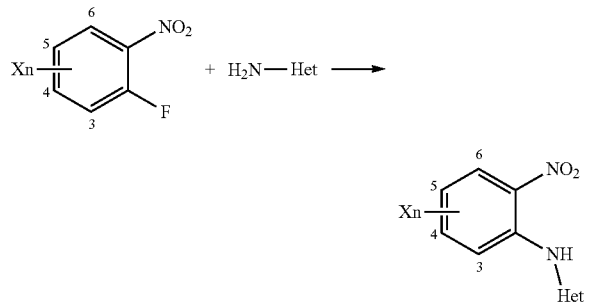

| Int. | X$_n$ | Het-NH$_2$ | Yield | RT$^a$ | MH$^+$ |
|---|---|---|---|---|---|
| I8 | — | 1-methyl-1H-imidazol-2-amine | 38%$^b$ | 1.46 (B) | 219.1 |
| I9 | 4,6-F$_2$ | 5-amino-1-methyltetrazole | 58%$^b$ | 2.35 (B) | 257.1 |
| I10 | — | 2-amino-3-methylpyrazine | 53%$^b$ | 2.80 (B) | 231.1 |
| I11 | 4-CN | 5-amino-1-methyltetrazole | 82%$^{b,c}$ | 2.16 (B) | 246.1 |
| I12 | 5-CN | 5-amino-1-methyltetrazole | 90% | 2.15 (B) | 246.1 |
| I13 | 4-Br | 5-amino-1-methyltetrazole | 81% | 2.61 (B) | 301.0 |

$^a$RT = LCMS retention time in minutes using indicated Method (A-F);
$^b$Product obtained using an aqueous work-up, extracting with EtOAc, followed by chromatography on silica eluting with 0-50% EtOAc/PE;
$^c$Did not require chromatographic purification Following the same procedure as for Synthetic Intermediate ("Int.") J, substituting the nitroaryl starting material ("SM") I with the required nitroaryl, there were thus obtained the following aniline intermediates:

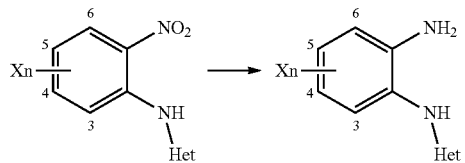

| SM | X$_n$ | Het | Aniline | Yield | RT$^a$ | MH$^+$ |
|---|---|---|---|---|---|---|
| I8 | — | 1-methylimidazol-2-yl | J8$^b$ | 100% | 0.80 (B) | 189.2 |
| I9 | 4,6-F$_2$ | 1-methyltetrazol-5-yl | J9$^b$ | 85% | 1.60 (B) | 227.1 |
| I11 | 4-CN | 1-methyltetrazol-5-yl | J11$^{b,c}$ | 78% | 1.38 (B) | 216.1 |
| I12 | 5-CN | 1-methyltetrazol-5-yl | J12$^d$ | 100% | 1.56 (B) | 216.1 |

$^a$RT = LCMS retention time in minutes using indicated Method (A-F);
$^b$Product used directly in next step without need for chromatographic purification;
$^c$Filter was washed with MeOH;
$^d$Impure product was carried through to next step N1-(3-Methylpyrazin-2-yl)benzene-1,2-diamine J10

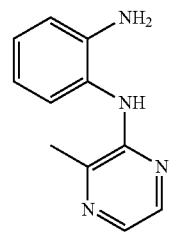

Using the same procedure as for J3, except that the reaction time was 4 h at 60° C., 3-methyl-N-(2-nitrophenyl)pyrazin-2-amine I10 was used as starting material instead of I3, and the product was used directly in next step without need for chromatographic purification, N1-(3-methylpyrazin-2-yl)benzene-1,2-diamine J10 (34% yield) was obtained as an orange solid.

$^1$H NMR (500 MHz, CDCl$_3$) δ 7.97 (d, J=2.7 Hz, 1H), 7.89 (d, J=2.8 Hz, 1H), 7.33 (dd, J=7.8, 1.3 Hz, 1H), 7.10 (td, J=7.8, 1.4 Hz, 1H), 6.91-6.84 (m, 2H), 6.03 (s, 1H), 3.87 (br s, 2H), 2.56 (s, 3H); LCMS (method B): 1.09 min (201.1, MH$^+$).

5-Bromo-N1-(1-methyl-1H-tetrazol-5-yl)benzene-1,2-diamine J13

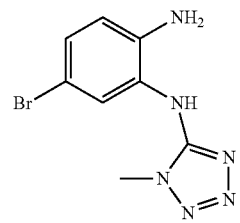

A solution of potassium carbonate (2.77 g, 20.1 mmol) and sodium hydrosulfite (3.49 g, 20.1 mmol) in water (6 mL) was added dropwise to a mixture of N-(5-bromo-2-nitrophenyl)-1-methyl-1H-tetrazol-5-amine I13 (1.00 g, 3.34 mmol) and 1,1'-di-n-octyl-4,4'-bipyridinium dibromide (0.064 g, 0.17 mmol) in dichloroethane (48 mL). The mixture was stirred and heated under reflux for 48 h then cooled, quenched with water (50 mL), acidified with citric acid and extracted into DCM (2×50 mL). The organic layers were combined, washed with brine, dried (MgSO$_4$) and purified by chromatography on silica (25 g Puriflash cartridge) eluting with 0-10% methanol/DCM) to give 5-bromo-N1-(1-methyl-1H-tetrazol-5-yl)benzene-1,2-diamine J13 (530 mg, 59%) as an orange solid.

¹H NMR (500 MHz, CDCl₃) δ 7.27 (s, 1H), 7.08 (d, J=8.0 Hz, 1H), 6.66 (d, J=8.4 Hz, 1H), 3.74 (s, 2H); LCMS (method B): 1.79 min (271.1, MH⁺).

N,N-bis(n-Butyloxycarbonyl)-6-[(t-butyl(dimethyl) silyl)oxymethyl]pyridin-2-amine L1

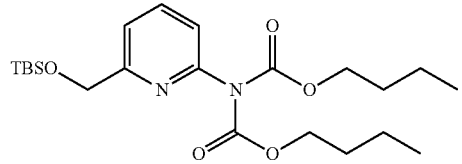 [SMILES: CCCCOC(=O)N(C(=O)OCCCC)c1cccc(CO[Si](C)(C)C(C)(C)C)n1]

n-Butyl chloroformate (0.064 mL, 0.503 mmol) was added to a solution of 6-(((tert-butyldimethylsilyl)oxy)methyl) pyridin-2-amine B (100 mg, 0.42 mmol) in DCM (5 mL) and pyridine (0.041 mL, 0.50 mmol) at 0° C. The reaction mixture was stirred at 0° C. for 2 h then diluted with water (30 mL), extracted with DCM (2×30 mL), washed with brine, dried (MgSO₄) and chromatographed on silica (12 g Puriflash cartridge) eluting with 0-50% EtOAc/PE to give N,N-bis(n-butyloxycarbonyl)-6-[(t-butyl(dimethyl)silyl) oxymethyl]pyridin-2-amine L¹ as a colourless oil (127 mg, 69%). ¹H NMR (500 MHz, CDCl₃) δ 7.80 (d, J=8.2 Hz, 1H), 7.69 (t, J=7.9 Hz, 1H), 7.17 (dd, J=7.5, 0.8 Hz, 1H), 4.68 (s, 2H), 4.18 (t, J=6.7 Hz, 2H), 4.13 (t, J=4.1 Hz, 2H), 1.70-1.62 (m, 4H), 1.46-1.36 (m, 4H), 0.97-0.91 (m, 12H), 0.88-0.82 (m, 3H), 0.12-0.09 (m, 6H); LCMS (method A): 3.97 min (339.1, MH⁺).

Butyl (6-(hydroxymethyl)pyridin-2-yl)carbamate N1

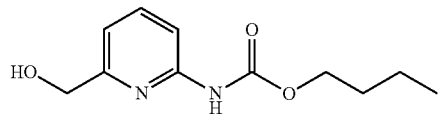 [SMILES: CCCCOC(=O)Nc1cccc(CO)n1]

A solution of N,N-bis(n-butyloxycarbonyl)-6-[(t-butyl (dimethyl)silyl)oxymethyl]pyridin-2-amine L¹ (500 mg, 1.14 mmol) in THF (10 mL) was treated with a solution of lithium hydroxide monohydrate (96 mg, 2.3 mmol) in water (2.5 mL) and butanol (2.5 mL) and heated under reflux for 16 h. Saturated aqueous NH₄Cl was added (to pH 8) and the mixture was diluted with ethyl acetate (20 mL), washed with water (3×20 mL) and brine (20 mL), dried (MgSO₄) and chromatographed on silica (40 g Puriflash cartridge) eluting with 20-50% EtOAc/PE to give butyl (6-(hydroxymethyl) pyridin-2-yl)carbamate N1 as a colourless oil (203 mg, 79%). ¹H NMR (500 MHz, CDCl₃) δ 7.86 (d, J=8.2 Hz, 1H), 7.71-7.65 (m, 1H), 7.40 (s, 1H), 6.92 (dd, J=7.5, 0.5 Hz, 1H), 4.66 (s, 2H), 4.19 (t, J=6.7 Hz, 2H), 3.39 (s, 1H), 1.71-1.63 (m, 2H), 1.47-1.38 (m, 2H), 0.95 (t, J=9.8 Hz, 3H); LCMS (method B): 2.01 min (225.1, MH⁺).

Following the same procedure as for Synthetic Intermediate Q, with the appropriate aniline starting material in place of N¹-(1-methyl-1H-tetrazol-5-yl)benzene-1,2-diamine J, except that an extractive work-up followed by chromatography on silica was carried out if a solid was not obtained upon dilution with water, there were thus obtained the following intermediates:

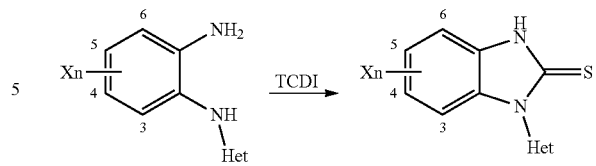

| Int. | Xₙ | Het- | SM | Yield | RT^a | MH⁺ |
|---|---|---|---|---|---|---|
| Q8 | — | 1-methylimidazol-2-yl | J8 | 56%^b | 1.51 (B) | 231.1 |
| Q9 | 4,6-F₂ | 1-methyltetrazol-5-yl | J9 | 95%^b | 2.28 (B) | 269.1 |
| Q10 | — | 3-methylpyrazin-2-yl | J10 | 92%^b | 1.87 (B) | 243.1 |
| Q11 | 4-CN | 1-methyltetrazol-5-yl | J11 | 22% | See 1H NMR^d | |
| Q12 | 5-CN | 1-methyltetrazol-5-yl | J12 | 7% | 1.34 (F) | 256.3^c |

^aRT = LCMS retention time in minutes using indicated Method (A-F);
^bExtractive work-up followed by chromatography;
^c(M − H)⁻;
^dNMR (¹H, 500 MHz, d₆-DMSO) δ 14.12 (br s, 1H), 7.77 (dd, J = 8.3, 1.5 Hz, 1H), 7.69 (d, J = 1.0 Hz, 1H), 7.46 (dd, J = 8.3, 0.5 Hz, 1H), 4.07 (s, 3H).

6-Bromo-1-(1-methyl-1H-tetrazol-5-yl)-1,3-dihydro-2H-benzo[d]imidazole-2-thione Q13

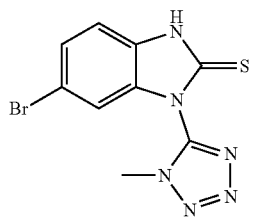 [SMILES: Cn1nnnc1-n1c(=S)[nH]c2ccc(Br)cc21]

Ethylxanthic acid potassium salt (953 mg, 5.91 mmol) was added to a solution of 5-bromo-N1-(1-methyl-1H-tetrazol-5-yl)benzene-1,2-diamine J13 (530 mg, 1.97 mmol) in EtOH (8 mL) and water (0.4 mL) and the mixture was heated under reflux for 60 h then diluted with water, quenched with saturated aqueous ammonium chloride solution and extracted with EtOAc (2×100 mL). The organic layers were combined, washed with water (3×20 mL) and brine, dried (MgSO₄) and concentrated in vacuo to give 6-bromo-1-(1-methyl-1H-tetrazol-5-yl)-1,3-dihydro-2H-benzo[d]imidazole-2-thione Q13 (492.9 mg, 80%) as a pink solid.

¹H NMR (500 MHz, CDCl₃) δ 7.21 (dd, J=8.5, 1.7 Hz, 1H), 6.97-6.95 (m, 1H), 6.94 (s, 1H), 3.95 (s, 3H); LCMS (method B): 2.52 min (313.0, MH⁺).

Following the same procedure as for Synthetic Intermediate R, with the appropriate starting material in place of 1-(1-methyl-1H-tetrazol-5-yl)-1,3-dihydro-2H-benzo[d] imidazole-2-thione Q, there were thus obtained the following intermediates:

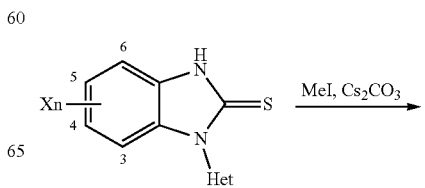

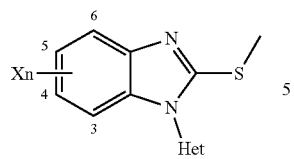

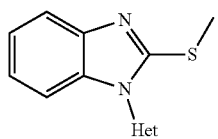

| Int. | $X_n$ | Het- | SM | Yield | RT[a] | MH+ |
|---|---|---|---|---|---|---|
| R8[b] | — | 1-methylimidazol-2-yl | Q8 | 86% | 1.80 (B) | 245.1 |
| R9[c] | 4,6-$F_2$ | 1-methyltetrazol-5-yl | Q9 | 90% | 2.59 (B) | 283.1 |
| R10[d] | — | 3-methylpyrazin-2-yl | Q10 | 97% | 2.19 (B) | 257.1 |
| R11[d] | 4-CN | 1-methyltetrazol-5-yl | Q11 | 59% | 2.15 (B) | 272.1 |
| R12[d] | 5-CN | 1-methyltetrazol-5-yl | Q12 | 48% | 2.26 (B) | 272.1 |
| R17 | 4-Br | 1-methyltetrazol-5-yl | Q13 | 82% | 2.73 (B) | 327.0 |

[a]RT = LCMS retention time in minutes using indicated Method (A-F);
[b]Contains DMF but used directly in next step;
[c]Eluent for chromatography was 0-5% MeOH/DCM;
[d]Eluent for chromatography was 0-100% EtOAc/PE.

| Int. | Het- | X | Yield | RT[a] | MH+ |
|---|---|---|---|---|---|
| R14 | 3-chloropyridin-2-yl | 2-F | 38% | 2.62 (B) | 276.2 |
| R15 | 5-chloropyrimidin-4-yl | 4-Cl | 50% | 2.58 (B) | 277.0 |
| R16 | 5-methoxypyrimidin-4-yl | 4-Cl | 18% | 2.13 (B) | 273.1 |

[a]RT = LCMS retention time in minutes using indicated Method (A-F).

Following the same procedure as for Synthetic Intermediate S, with the appropriate starting material in place of 1-(1-methyl-1H-tetrazol-5-yl)-2-(methylthio)-1H-benzo[d]imidazole R, there were thus obtained the following intermediates:

1-(3-Bromopyridin-2-yl)-2-(methylthio)-1H-benzo[d]imidazole R13

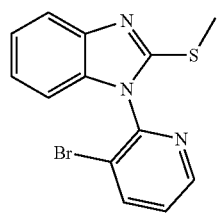 [SMILES: CSc1nc2ccccc2n1-c1ncccc1Br]

An ice-cold mixture of 3-bromo-2-fluoropyridine (0.136 mL, 1.34 mmol) and 2-methylthiobenzimidazole (200 mg, 1.22 mmol) in dry DMF (2 ml) was treated with potassium tert-butoxide (150 mg, 1.34 mmol). The mixture was heated to 80° C. for 16 h. The solution was cooled, quenched with saturated aq. $NH_4Cl$ (to pH 6-7), diluted with water (20 mL) and extracted with EtOAc (2×20 mL). The organic extracts were washed with water (20 mL) and brine, dried ($MgSO_4$) and chromatographed on silica (25 g Puriflash cartridge) eluting with 10-50% EtOAc/heptane to give 1-(3-bromopyridin-2-yl)-2-(methylthio)-1H-benzo[d]imidazole R13 (285 mg, 73%), as a white solid.

$^1$H NMR (500 MHz, $CDCl_3$) δ 8.67 (d, J=4.6 Hz, 1H), 8.19 (d, J=8.1 Hz, 1H), 7.76 (d, J=7.9 Hz, 1H), 7.42 (dd, J=8.0, 4.6 Hz, 1H), 7.31-7.26 (m, 1H), 7.19 (t, J=7.6 Hz, 1H), 6.97 (d, J=8.0 Hz, 1H), 2.80 (s, 3H); LCMS (method B): 2.76 min (319.9 and 321.9 MH+, Br isotope peaks).

Following a procedure analagous to that for Synthetic Intermediate R13, with the appropriate starting material in place of 3-bromo-2-fluoropyridine, and at a reaction temperature of 50-90° C., there were thus obtained the following intermediates:

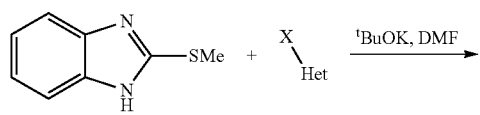

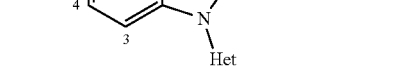

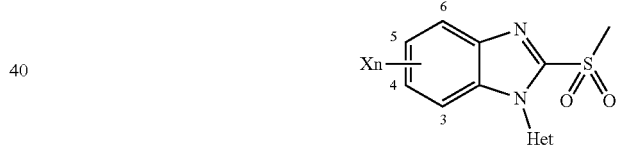

| Int. | $X_n$ | Het- | SM | Yield | RT[a] | MH+ |
|---|---|---|---|---|---|---|
| S8[b] | — | 1-methylimidazol-2-yl | R8 | 77% | 1.75 (B) | 277.1 |
| S9[c] | 4,6-$F_2$ | 1-methyltetrazol-5-yl- | R9 | 22% | 1.51 (B) | 315.1 |
| S10[b] | — | 3-methylpyrazin-2-yl | R10 | 63% | 2.00 (B) | 289.1 |
| S11[c] | 4-CN | 1-methyltetrazol-5-yl- | R11 | 48% | 2.32 (B) | 304.0 |
| S12[b,c] | 5-CN | 1-methyltetrazol-5-yl- | R12 | 40% | 1.42 (F) | 304.0 |
| S13[c] | — | 3-bromopyridin-2-yl- | R13 | 85% | 2.43 (B) | 352.0 |
| S14[c,b] | — | 3-chloropyridin-2-yl- | R14 | 65% | 2.42 (B) | 308.0 |
| S15[b] | — | 5-chloropyrimidin-4-yl- | R15 | 83% | 2.33 (B) | 309.0 |
| S16[b] | — | 5-methoxypyrimidin-4-yl | R16 | 93% | 2.02 (B) | 305.1 |
| S17 | 4-Br | 1-methyltetrazol-5-yl- | R17 | 70% | 2.78 (B) | 359.0 |

[a]RT = LCMS retention time in minutes using indicated Method (A-D);
[b]Eluent for chromatography was 0-100% EtOAc/PE;
[c]Eluent for chromatography was 0-7% MeOH/DCM.

1-(5-Chloropyrimidin-4-yl)-2-(phenylthio)-1H-benzo[d]imidazole U

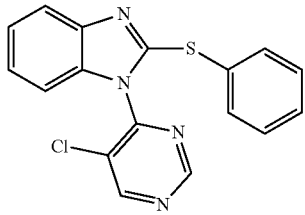 [SMILES: Clc1cncnc1-n1c(Sc2ccccc2)nc2ccccc21]

A solution of 1-(5-chloropyrimidin-4-yl)-2-(methylsulfonyl)-1H-benzo[d]imidazole S15 (49.5 mg, 0.16 mmol) in dry DMF (1 mL) was treated with 90% sodium thiophenolate (24 mg, 0.16 mmol) and stirred at RT for 90 min then was diluted with EtOAc (20 mL), washed with water (3×20 mL) and brine, dried (MgSO$_4$) and chromatographed on silica (12 g Puriflash cartridge) eluting with 20-50% EtOAc/PE to give 1-(5-chloropyrimidin-4-yl)-2-(phenylthio)-1H-benzo[d]imidazole U (43 mg, 79%) as a colourless gum. $^1$H NMR (500 MHz, CDCl$_3$) δ 9.14 (s, 1H), 8.91 (s, 1H), 7.80 (d, J=7.9 Hz, 1H), 7.41-7.18 (m, 7H), 7.06 (d, J=8.0 Hz, 1H); LCMS (Method B): 2.9 min (339.1 and 341.0, MH$^+$).

Following the same procedure as for Synthetic Intermediate U, with the appropriate starting material in place of 1-(5-chloropyrimidin-4-yl)-2-(methylsulfonyl)-1H-benzo[d]imidazole S15, there were thus obtained the following intermediates U1-U3:

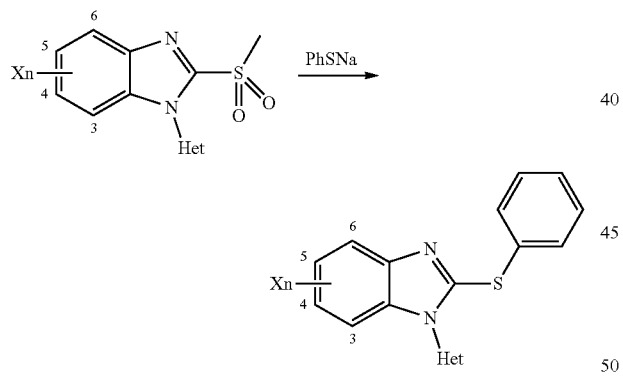

| Int. | X$_n$ | Het- | SM | Yield | RT$^a$ | MH$^+$ |
|---|---|---|---|---|---|---|
| U1$^b$ | — | 5-methoxypyrimidin-4-yl | S16 | 54% | 2.69 (B) | 335.1 |
| U2 | — | 1-methyltetrazol-5-yl- | S | 97% | 2.77 (B) | 309.1 |
| U3 | 4-Br | 1-methyltetrazol-5-yl- | S17 | 45% | 3.14 (B) | 389.0 |

$^a$RT = LCMS retention time in minutes using indicated Method (A-F);
$^b$Another 0.25 equiv. NaSPh was added and the total reaction time was 21 h.

Following the same procedure as for Synthetic Intermediate S, with the appropriate PhS-substituted starting material in place of 1-(1-methyl-1H-tetrazol-5-yl)-2-(methylthio)-1H-benzo[d]imidazole R, there were thus obtained the following PhSO$_2$-substituted intermediates V-V3:

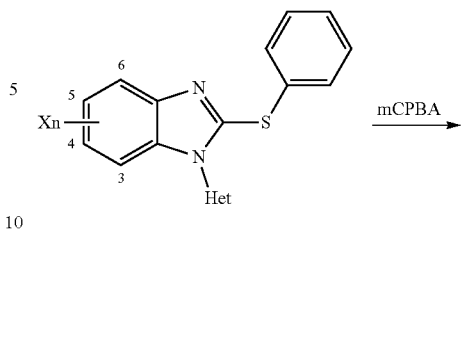

| Int. | X$_n$ | Het- | SM | Yield | RT$^a$ | MH$^+$ |
|---|---|---|---|---|---|---|
| V | — | 5-chloropyrimidin-4-yl | U | 79% | 2.77 (B) | 371.1 |
| V1 | — | 5-methoxypyrimidin-4-yl | U1 | 49% | 2.63 (B) | 367.1 |
| V2$^b$ | — | 1-methyltetrazol-5-yl- | U2 | 77% | 2.77 (B) | 341.1 |
| V3 | 4-Br | 1-methyltetrazol-5-yl- | U3 | 65% | 3.06 (B) | 321.0 |

$^a$RT = LCMS retention time in minutes using indicated Method (A-F).
$^b$initial reaction time was 18 h then more mCPBA (0.4 equiv.) was added for another 5 h reaction time.

3-(5-Chloropyrimidin-4-yl)indolin-2-one W

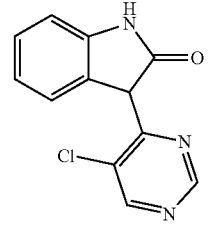

An ice-cooled suspension of 60% sodium hydride (118 mg, 2.95 mmol) in mineral oil in dry DMF (2 mL) was treated with 2-oxindole (190 mg, 1.43 mmol) and stirred under N$_2$ for 5 min to give an orange solution then 4,5-dichloropyrimidine (204 mg, 1.37 mmol) was added in dry DMF (1 mL). After 20 min. the mixture was quenched with saturated aq. NH$_4$Cl solution to pH 7. The product was extracted into EtOAc (50 mL) and the organics were washed with water (3×50 mL) and brine then dried (MgSO$_4$), loaded onto silica (2 g) and chromatographed on SiO$_2$ (12 g Claricep i-Series cartridge) eluting with 1.5-5% MeOH/DCM. Trituration with DCM gave 3-(5-chloropyrimidin-4-yl)indolin-2-one W (183 mg, 54%) as a solid. $^1$H NMR (500 MHz, CDCl$_3$) b 9.02 (s, 1H), 8.76 (s, 1H), 8.20 (s, 1H), 7.28 (ddd, J=7.8, 4.4, 3.4 Hz, 1H), 7.10 (d, J=7.5 Hz, 1H), 7.01 (td, J=7.6, 0.9 Hz, 1H), 6.96 (d, J=7.8 Hz, 1H), 5.33 (s, 1H); LCMS (Method B): 1.82 min (246.0 and 248.0, MH$^+$).

(6-(2,2-Difluoro-2-phenoxyacetamido)pyridin-2-yl) methyl methanesulfonate X

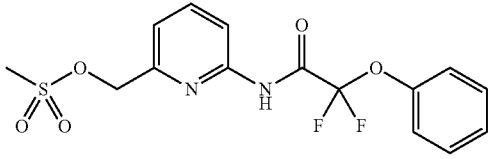 [SMILES: CS(=O)(=O)OCc1cccc(NC(=O)C(F)(F)Oc2ccccc2)n1]

An ice-cooled solution of 2,2-difluoro-N-(6-(hydroxymethyl)pyridin-2-yl)-2-phenoxyacetamide (108 mg, 0.367 mmol) in DCM (1 mL) was treated with methanesulfonyl chloride (0.030 mL, 0.39 mmol) then triethylamine (0.054 mL, 0.39 mmol) and stirred for 40 min. The mixture was diluted with DCM (20 mL), washed with water (20 mL) and brine, dried (MgSO$_4$) and chromatographed on silica (12 g Puriflash cartridge) eluting with 30-50% EtOAc/PE to give (6-(2,2-difluoro-2-phenoxyacetamido)pyridin-2-yl)methyl methanesulfonate X (132 mg, 87%), as a colourless gum. $^1$H NMR (500 MHz, CDCl$_3$) δ 8.78 (s, 1H), 8.25 (d, J=8.3 Hz, 1H), 7.86 (t, J=7.9 Hz, 1H), 7.45-7.37 (m, 2H), 7.32 (t, J=4.8 Hz, 1H), 7.31-7.26 (m, 3H), 5.24 (s, 2H), 3.08 (s, 3H); LCMS (Method B): 2.95 min (373.1, MH$^+$).

3-Methyl-N-(2-nitropyridin-3-yl)pyridin-2-amine Y

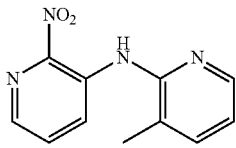

An ice-cold suspension of 2-amino-3-methylpyridine (0.186 ml, 1.85 mmol) and 3-fluoro-2-nitropyridine (289 mg, 2.03 mmol) in dry DMF (3 ml) was treated with potassium tert-butoxide (415 mg, 3.70 mmol) and the mixture was stirred at RT for 18 h. The reaction was quenched with water (40 mL) and extracted with EtOAc (2×40 mL). The organic layer was washed with water (40 mL) and brine, dried (MgSO$_4$) and concentrated to give a dark gum. This residue was purified on silica (24 g Puriflash cartridge) eluting with 0-50% EtOAc/Heptane to give 3-methyl-N-(2-nitropyridin-3-yl)pyridin-2-amine Y (148 mg, 35%) as a pale orange solid.

$^1$H NMR (500 MHz, CDCl$_3$) δ 10.06 (s, 1H), 9.57 (dd, J=8.6, 1.0 Hz, 1H), 8.21 (d, J=4.3 Hz, 1H), 8.15 (dd, J=4.0, 1.3 Hz, 1H), 7.59 (dd, J=8.6, 4.1 Hz, 1H), 7.54 (d, J=7.3 Hz, 1H), 6.95 (dd, J=7.3, 5.0 Hz, 1H), 2.42 (s, 3H); LCMS (method A): 2.27 min (231.0, MH$^+$).

N3-(3-Methylpyridin-2-yl)pyridine-2,3-diamine Z

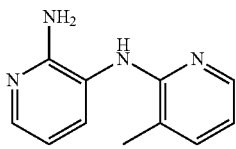

Following the same procedure as for Synthetic Intermediate J, substituting the nitroaryl starting material I with Y, there was obtained N3-(3-methylpyridin-2-yl)pyridine-2,3-diamine Z (93% yield) as an off white solid. The product was used directly in next step without need for chromatographic purification.

$^1$H NMR (500 MHz, CDCl$_3$) δ 8.05 (dd, J=5.0, 1.2 Hz, 1H), 7.95 (dd, J=5.0, 1.5 Hz, 1H), 7.57 (dd, J=7.7, 1.5 Hz, 1H), 7.38 (dd, J=7.2, 0.8 Hz, 1H), 6.75 (dd, J=7.6, 5.0 Hz, 1H), 6.72 (dd, J=7.2, 5.0 Hz, 1H), 5.71 (s, 1H), 4.68 (s, 2H), 2.25 (s, 3H); LCMS (method A): 1.42 min (201.1, MH$^+$)

1-(3-Methylpyridin-2-yl)-1,3-dihydro-2H-imidazo[4,5-b]pyridine-2-thione AA

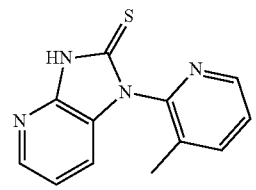 [SMILES: Cc1cccnc1-n1c(=S)[nH]c2ncccc21]

Following the same procedure as for Synthetic Intermediate Q, with aniline Z in place of N$^1$-(1-methyl-1H-tetrazol-5-yl)benzene-1,2-diamine J, except that an extractive work-up was followed by trituration with Pet Ether, there was obtained 1-(3-methylpyridin-2-yl)-1,3-dihydro-2H-imidazo[4,5-b]pyridine-2-thione AA (61% yield) as a pale yellow solid.

$^1$H NMR (500 MHz, d$_4$-MeOH) δ 8.48 (dd, J=4.8, 1.3 Hz, 1H), 8.19 (dd, J=4.8, 1.6 Hz, 1H), 7.99-7.96 (m, 1H), 7.66 (s, 1H), 7.56 (dd, J=7.7, 4.8 Hz, 1H), 7.15 (dd, J=8.0, 4.9 Hz, 1H), 7.12 (dd, J=7.9, 1.6 Hz, 1H), 2.21 (s, 3H); LCMS (method A) 1.63 min (243.0, MH$^+$)

1-(3-Methylpyridin-2-yl)-2-(methylthio)-1H-imidazo[4,5-b]pyridine AB

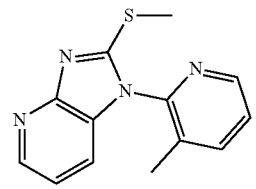 [SMILES: CSc1nc2ncccc2n1-c1ncccc1C]

Following the same procedure as for Synthetic Intermediate R, with AA as a starting material in place of 1-(1-methyl-1H-tetrazol-5-yl)-1,3-dihydro-2H-benzo[d]imidazole-2-thione Q, there was obtained 1-(3-methylpyridin-2-yl)-2-(methylthio)-1H-imidazo[4,5-b]pyridine AB (65% yield) as a yellow gum, used in the next step without need for chromatographic purification.

$^1$H NMR (500 MHz, CDCl$_3$) δ 8.55 (dd, J=4.7, 1.3 Hz, 1H), 8.46 (dd, J=4.8, 1.5 Hz, 1H), 7.82 (dd, J=7.7, 1.0 Hz, 1H), 7.45 (dd, J=7.7, 4.7 Hz, 1H), 7.23 (dd, J=7.9, 1.5 Hz, 1H), 7.08 (dd, J=7.9, 4.8 Hz, 1H), 2.83 (s, 3H), 2.14 (s, 3H); LCMS (method A): 1.68 min (257.0, MH$^+$) 1-(3-Methylpyridin-2-yl)-2-(methylsulfonyl)-1H-imidazo[4,5-b]pyridine AC

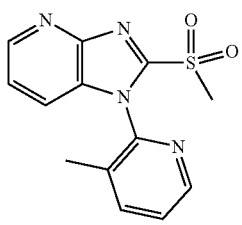 [SMILES: Cc1cccnc1-n1c(S(C)(=O)=O)nc2ncccc21]

Following the same procedure as for Synthetic Intermediate S, with AB as starting material in place of 1-(1-methyl-1H-tetrazol-5-yl)-2-(methylthio)-1H-benzo[d]imidazole R, and with purification on silica (25 g Biotage KP-Sil cartridge) eluting with 0-5% MeOH/DCM, there was obtained 1-(3-methylpyridin-2-yl)-2-(methylsulfonyl)-1H-imidazo[4,5-b]pyridine AC (59% yield) as a yellow gum.

$^1$H NMR (500 MHz, CDCl$_3$) δ 8.78 (dd, J=4.6, 1.5 Hz, 1H), 8.53 (dd, J=4.7, 1.3 Hz, 1H), 7.85 (dd, J=7.6, 0.9 Hz, 1H), 7.50 (dd, J=7.7, 4.8 Hz, 1H), 7.46 (dd, J=8.3, 1.6 Hz, 1H), 7.39 (dd, J=8.3, 4.6 Hz, 1H), 3.52 (s, 3H), 2.16 (s, 3H); LCMS (method A) 1.80 min (289.0, MH$^+$).

Exemplary Compounds

Example 1—2,2-Difluoro-N-(6-(((1-(1-methyl-1H-tetrazol-5-yl)-1H-benzo[d]imidazol-2-yl)oxy)methyl)pyridin-2-yl)-2-phenoxyacetamide 1

1

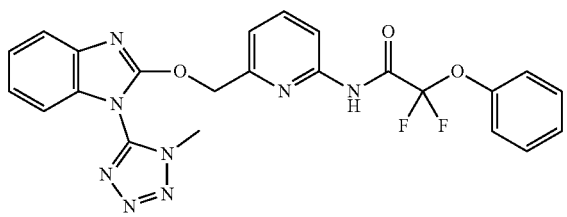

A solution of 2,2-difluoro-N-(6-(hydroxymethyl)pyridin-2-yl)-2-phenoxyacetamide D (67.7 mg, 0.230 mmol) in dry DMF (1 ml) was treated with sodium hydride (60% in mineral oil, 20 mg, 0.500 mmol), stirred at RT under N$_2$ for 5 min (gave a brown solution), treated with a solution of 2-chloro-1-(1-methyl-1H-tetrazol-5-yl)-1H-benzo[d]imidazole H1 (54 mg, 0.230 mmol) in with DMF (1 ml) (effervesced) and heated to 50° C. for 30 min. The mixture was treated with saturated aq. ammonium chloride (2 mL, to pH 8), diluted with EtOAc (20 mL) and washed with water (3×20 mL) and brine to give a gum (111 mg) which was chromatographed on SiO$_2$ (12 g Puriflash column) eluting with 30-50% EtOAc/Hexane to give 2,2-difluoro-N-(6-(((1-(1-methyl-1H-tetrazol-5-yl)-1H-benzo[d]imidazol-2-yl)oxy)methyl)pyridin-2-yl)-2-phenoxyacetamide 1 (54 mg, 48%) as a gum, triturated with ether to give a white solid (40 mg).

$^1$H NMR (500 MHz, CDCl$_3$) δ 8.85 (s, 1H), 8.21 (d, J=8.3 Hz, 1H), 7.81 (t, J=7.9 Hz, 1H), 7.61 (d, J=8.0 Hz, 1H), 7.43-7.37 (m, 2H), 7.34-7.27 (m, 4H), 7.25-7.22 (m, 3H), 5.66 (s, 2H), 4.05 (s, 3H). Contains ca. 0.5 mol EtOAc; LCMS (Method A): 3.29 min (493.1, MH$^+$).

Using the method described in Example 1, substituting either or both of the alcohol D or the 2-chloro-heterocycle derivative H1 with the appropriate building block (Het-Cl and ROH in the following table), there were thus obtained the following Examples (Ex. 2-4):

| Ex. | Het-Cl | ROH | Yield | $^1$H NMR δ(CDCl$_3$) | RT$^a$ | Structure |
|---|---|---|---|---|---|---|
| 2 | H1$^b$ | N | 45% | 7.92 (d, J = 8.4 Hz, 1H), 7.70-7.65 (m, 1H), 7.62 (d, J = 7.9 Hz, 1H), 7.35-7.23 (m, 1H), 7.17 (s, 1H), 7.04 (d, J = 7.4 Hz, 1H), 5.58 (s, 1H), 4.04 (s, 1H), 1.52 (s, 9H). | 3.09 (B) | 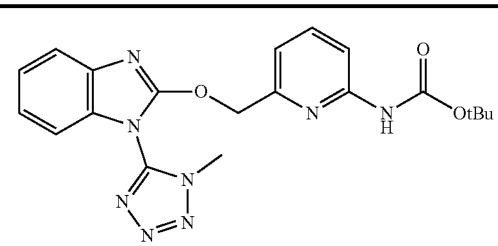 |
| 3 | H3$^{c,d}$ | D | 22% | 8.88 (s, 1H), 8.53 (d, J = 3.5 Hz, 1H), 8.14 (d, J = 8.2 Hz, 1H), 7.78 (ddd, J = 7.7, 1.8, 0.7 Hz, 1H), 7.76-7.72 (m, 1H), 7.61 (d, J = 7.8 Hz, 1H), 7.39 (ddd, J = 8.9, 7.7, 6.0 Hz, 3H), 7.32-7.26 (m, 2H), 7.24-7.18 (m, 2H), 7.13 (td, J = 7.7, 1.1 | 8.93 (D) | 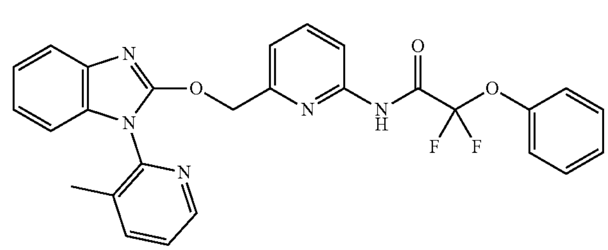 [SMILES: Cc1cccnc1-n1c(OCc2cccc(NC(=O)C(F)(F)Oc3ccccc3)n2)nc2ccccc21] |

| Ex. | Het-Cl | ROH | Yield | $^1$H NMR δ(CDCl$_3$) | RT$^a$ | Structure |
|---|---|---|---|---|---|---|
| | | | | Hz, 1H), 6.97 (d, J = 7.6 Hz, 1H), 5.64 (d, J = 36.5 Hz, 2H), 2.22 (s, 3H). | | |
| 4 | P$^{d,e}$ | D | 36% | 8.72 (s, 1H), 8.20 (d, J = 8.2 Hz, 1H), 7.80 (t, J = 7.9 Hz, 1H), 7.65 (d, J = 2.0 Hz, 1H), 7.62 (d, J = 7.8 Hz, 1H), 7.41 (dt, J = 10.7, 2.2 Hz, 2H), 7.29 (ddd, J = 8.6, 7.5, 3.7 Hz, 4H), 7.23-7.16 (m, 2H), 7.01 (d, J = 7.8 Hz, 1H), 6.39 (d, J = 2.0 Hz, 1H), 5.62 (s, 2H), 3.70 (s, 3H). | 3.20 (B) | 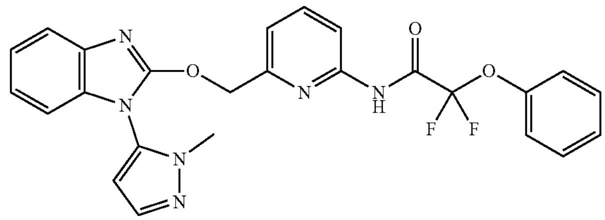 [SMILES: Cn1nccc1-n1c(OCc2cccc(NC(=O)C(F)(F)Oc3ccccc3)n2)nc2ccccc21] |

$^a$RT = LCMS retention time in minutes using indicated Method (A-D);
$^b$Reaction conducted at RT for 1 h;
$^c$Reaction conducted at 60° C. with two further additions of NaH until complete (20 h);
$^d$Additional purification was by preparative LC-MS;
$^e$Reaction conducted at 0° C. for 1 h.

Example 5—N-(6-(((1-(3,4-Dimethylisoxazol-5-yl)-1H-benzo[d]imidazol-2-yl)oxy)methyl)pyridin-2-yl)-2,2-difluoro-2-phenoxyacetamide 5

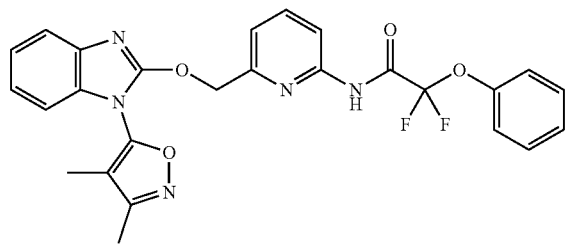

A solution of 2,2-difluoro-N-(6-(hydroxymethyl)pyridin-2-yl)-2-phenoxyacetamide D (27.8 mg, 0.094 mmol) in dry DMF (0.4 ml) in an ice bath, was treated with sodium hydride (5.2 mg, 0.13 mmol) with stirring under nitrogen for 10 min, then a solution of 3,4-dimethyl-5-(2-(methylsulfonyl)-1H-benzo[d]imidazol-1-yl)isoxazole S1 (25 mg, 0.086 mmol) in dry DMF (0.5 ml) was added dropwise. The reaction was stirred in an ice bath for 1 h and at room temperature overnight then quenched with water, neutralised with saturated aq. ammonium chloride solution and extracted with EtOAc (2×10 mL). The combined extracts were washed with water and brine, dried (MgSO$_4$) and concentrated to give a yellow oil. This oil was purified by chromatography on silica (10 g Biotage Snap KP-Sil column) eluting with 0-50% EtOAc/PE, followed by mass-directed preparative LC-MS to give N-(6-(((1-(3,4-dimethylisoxazol-5-yl)-1H-benzo[d]imidazol-2-yl)oxy)methyl)pyridin-2-yl)-2,2-difluoro-2-phenoxyacetamide 5 (20 mg, 46%) as a colourless gum.

$^1$H NMR (500 MHz, CDCl$_3$) δ 8.78 (s, 1H), 8.20 (d, J=8.3 Hz, 1H), 7.81 (t, J=7.9 Hz, 1H), 7.59 (d, J=7.9 Hz, 1H), 7.43-7.37 (m, 2H), 7.32-7.25 (m, 5H), 7.20 (td, J=7.6, 1.1 Hz, 1H), 7.17-7.13 (m, 1H), 5.63 (s, 2H), 2.33 (s, 3H), 1.91 (s, 3H); LCMS (Method B): 3.54 min (506.3, MH$^+$).

Using the method described in Example 5, substituting either or both of alcohol D or methylsulphonyl-heterocycle derivative S1 with the appropriate building block (Het-X and ROH in table), using up to 2.5 equiv. NaH with monitoring for at least ca. 70% conversion, and omitting the prep. LC-MS where it was not necessary, there were thus obtained the following Examples (Ex. 6-9):

| Ex. | Het-X | ROH | Yield | $^1$H NMR δ(CDCl$_3$) | RT$^a$ | Structure |
|---|---|---|---|---|---|---|
| 6 | S2 | D | 40% | 11.71 (s, 1H), 7.99-7.91 (m, 2H), 7.59 (dd, J = 8.8, 4.7 Hz, 1H), 7.51-7.44 (m, 2H), 7.40-7.36 (m, 3H), 7.34 (t, J = 7.3 Hz, 1H), 7.30 (dd, J = 8.8, 2.6 Hz, 1H), 7.18-7.12 (m, 1H), 5.67 (s, 2H), 4.09 (s, 3H) | 3.28 (B) | 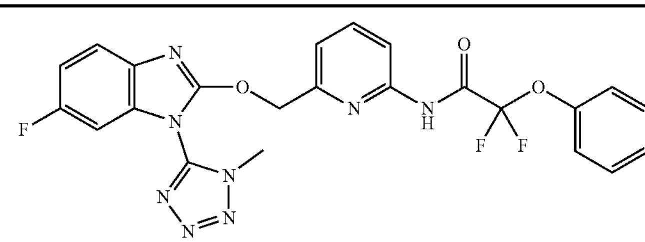 |

| Ex. | Het-X | ROH | Yield | ¹H NMR δ(CDCl₃) | RT$^a$ | Structure |
|---|---|---|---|---|---|---|
| 7 | S3 | D | 35% | 8.79 (s, 1H), 8.65 (ddd, J = 4.8, 1.8, 0.7 Hz, 1H), 8.20 (d, J = 8.3 Hz, 1H), 7.91-7.85 (m, 1H), 7.82-7.78 (m, 2H), 7.72-7.68 (m, 1H), 7.59 (dd, J = 7.7, 0.7 Hz, 1H), 7.40 (dt, J = 10.7, 2.2 Hz, 2H), 7.30 (ddd, J = 12.9, 8.2, 5.7 Hz, 5H), 7.25-7.19 (m, 2H), 5.70 (s, 2H) | 3.48 (B) | 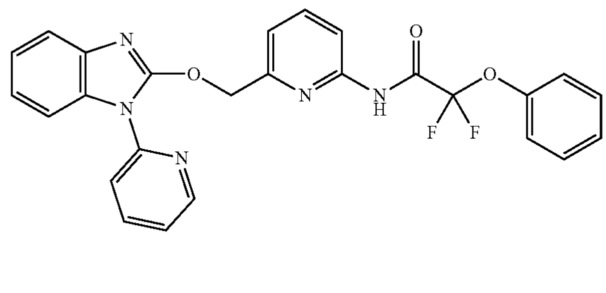 [SMILES: O=C(Nc1cccc(COc2nc3ccccc3n2-c2ccccn2)n1)C(F)(F)Oc1ccccc1] |
| 8 | S4 | D | 25% | 8.78 (s, 1H), 8.24 (d, J = 8.1 Hz, 1H), 7.85 (t, J = 7.9 Hz, 1H), 7.64-7.58 (m, 1H), 7.56-7.52 (m, 1H), 7.43-7.36 (m, 3H), 7.32-7.27 (m, 6H), 5.72 (s, 2H), 2.55 (s, J = 3.5 Hz, 3H) | 3.65 (B) | 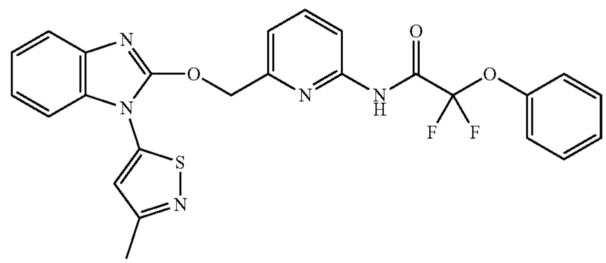 [SMILES: Cc1cc(-n2c(OCc3cccc(NC(=O)C(F)(F)Oc4ccccc4)n3)nc3ccccc32)sn1] |
| 9 | S5 | D | 28% | 8.64 (s, 1H), 8.31 (d, J = 1.7 Hz, 1H), 8.10 (d, J = 8.2 Hz, 1H), 7.97-7.90 (m, 1H), 7.71 (t, J = 7.9 Hz, 1H), 7.46-7.40 (m, 1H), 7.29-7.24 (m, 2H), 7.20 (d, J = 7.2 Hz, 1H), 7.17-7.12 (m, 5H), 6.78 (d, J = 1.7 Hz, 1H), 5.57 (s, 2H) | 3.54 (B) | 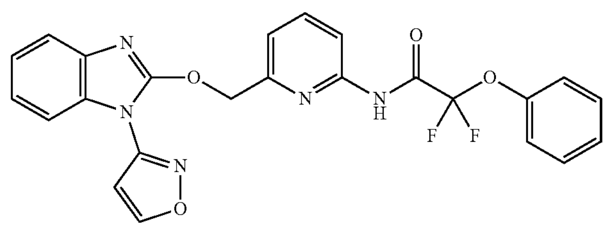 [SMILES: O=C(Nc1cccc(COc2nc3ccccc3n2-c2ccon2)n1)C(F)(F)Oc1ccccc1] |

$^a$RT = LCMS retention time in minutes using indicated Method (A-D).

Example 10—N-(6-(((1-(1-Methyl-1H-tetrazol-5-yl)-1H-benzo[d]imidazol-2-yl)oxy)methyl)pyridin-2-yl)acetamide 10

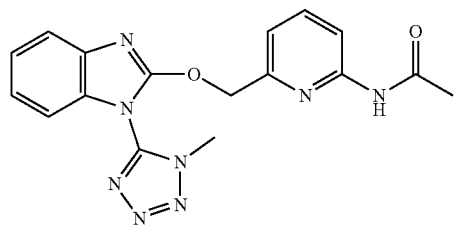 [SMILES: CC(=O)Nc1cccc(COc2nc3ccccc3n2-c2nnnn2C)n1]

Acetyl chloride (8.82 μL, 0.124 mmol) was added to a solution of 6-(((1-(1-methyl-1H-tetrazol-5-yl)-1H-benzo[d]imidazol-2-yl)oxy)methyl)pyridin-2-amine T (40 mg, 0.124 mmol) in DCM (2 mL) and pyridine (0.015 mL, 0.186 mmol) and the mixture was stirred at room temperature for 1 h. The reaction mixture was acidified with aq. citric acid solution (1.5 M), diluted with DCM, washed with water (3×10 mL) and brine, dried (MgSO₄) and chromatographed on silica (10 g Biotage Snap ultra cartridge) eluting with 20-100% EtOAc/PE to give N-(6-(((1-(1-methyl-1H-tetrazol-5-yl)-1H-benzo[d]imidazol-2-yl)oxy)methyl)pyridin-2-yl)acetamide 10 (17 mg, 38%) as a white solid.

¹H NMR (500 MHz, CDCl₃) δ 8.13 (d, J=8.3 Hz, 1H), 8.03 (s, 1H), 7.69 (t, J=7.9 Hz, 1H), 7.60 (d, J=7.9 Hz, 1H), 7.34-7.29 (m, 1H), 7.29-7.22 (m, 2H), 7.07 (d, J=7.5 Hz, 1H), 5.61 (s, 2H), 4.04 (s, 3H), 2.21 (s, 3H); LCMS (method C): 6.29 min (365.1, MH⁺).

Example 11—Ethyl (6-(((1-(1-methyl-1H-tetrazol-5-yl)-1H-benzo[d]imidazol-2-yl)oxy)methyl)pyridin-2-yl)carbamate 11

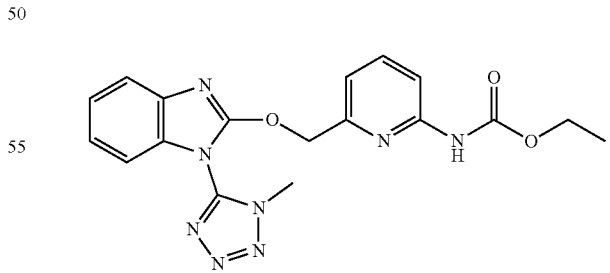

Ethyl chloroformate (0.020 ml, 0.207 mmol) was added to a solution of 6-(((1-(1-methyl-1H-tetrazol-5-yl)-1H-benzo[d]imidazol-2-yl)oxy)methyl)pyridin-2-amine T (37 mg, 0.115 mmol) and 4-(dimethylamino)pyridine (1.12 mg, 9.18 μmol) in 1,4-dioxane (2 mL) and pyridine (0.012 mL, 0.149 mmol) and the reaction mixture was stirred at room temperature for 4 h. Aqueous sodium bicarbonate solution (10 g/L, 7 mL) was added and the mixture was extracted with ethyl acetate (12 mL), dried (MgSO$_4$) and chromatographed on silica (12 g Puriflash cartridge) eluting with 30-100% EtOAc/PE to give ethyl (6-(((1-(1-methyl-1H-tetrazol-5-yl)-1H-benzo[d]imidazol-2-yl)oxy)methyl)pyridin-2-yl)carbamate 11 (8.2 mg, 18%) as a colourless gum.

$^1$H NMR (500 MHz, CDCl$_3$) δ 7.95 (d, J=8.4 Hz, 1H), 7.73-7.68 (m, 1H), 7.61 (d, J=7.9 Hz, 1H), 7.35 (d, J=7.1 Hz, 1H), 7.34-7.23 (m, 4H), 7.06 (d, J=7.3 Hz, 1H), 5.59 (s, 2H), 4.24 (q, J=7.1 Hz, 2H), 4.04 (s, 3H), 1.32 (td, J=7.1, 3.9 Hz, 3H); LCMS (method D): 7.34 min (395.2, MH$^+$).

Following the procedure of Example 11, using the appropriate starting materials, there were thus obtained the following Examples (Ex. 12-21):

| Ex. | R'OCOCl | Yield | $^1$H NMR δ(CDCl$_3$) | RT$^a$ | Structure |
|---|---|---|---|---|---|
| 12$^b$ | cyclopentyl-OCOCl | 6% | 7.95 (d, J = 8.4 Hz, 1H), 7.73-7.67 (m, 1H), 7.61 (d, J = 7.9 Hz, 1H), 7.35-7.21 (m, 4H), 7.06 (d, J = 7.4 Hz, 1H), 5.59 (s, 2H), 5.21 (dt, J = 8.9, 3.1 Hz, 1H), 4.04 (s, 3H), 1.94-1.83 (m, 2H), 1.82-1.69 (m, 4H), 1.68-1.57 (m, 2H). | 1.40 (A) | |
| 13$^c$ | n-butyl-OCOCl | 39% | 7.96 (d, J = 8.4 Hz, 1H), 7.73-7.68 (m, 1H), 7.62 (d, J = 7.9 Hz, 1H), 7.35-7.26 (m, 4H), 7.07 (d, J = 7.3 Hz, 1H), 5.59 (s, 2H), 4.19 (t, J = 6.7 Hz, 2H), 4.05 (s, 3H), 1.71-1.63, (m, 2H), 1.47-1.37 (m, 2H), 0.95 (t, J = 7.4 Hz, 3H). | 3.24 (A) | |
| 14 | benzyl-OCOCl | 51% | 7.97 (d, J = 8.4 Hz, 1H), 7.73-7.69 (m, 1H), 7.61 (dd, J = 7.9, 0.8 Hz, 1H), 7.43-7.26 (m, 9H), 7.07 (d, J = 7.3 Hz, 1H), 5.58 (s, 2H), 5.22 (s, 2H), 4.04 (s, 3H). | 3.24 (A) | |

| Ex. | R'OCOCl | Yield | $^1$H NMR δ(CDCl$_3$) | RT$^a$ | Structure |
|---|---|---|---|---|---|
| 15 | 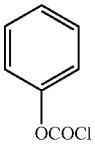 | 71% | 7.97 (d, J = 8.4 Hz, 1H), 7.81 (s, 1H), 7.77-7.71 (m, 1H), 7.65-7.60 (m, 1H), 7.43-7.38 (m, 2H), 7.35-7.26 (m, 4H), 7.21-7.17 (m, 2H), 7.12 (d, J = 7.4 Hz, 1H), 5.64 (s, 2H), 4.07 (s, 3H). | 3.16 (A) | 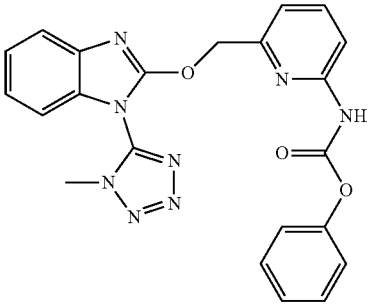 [SMILES: Cn1nnnc1-n1c(OCc2cccc(NC(=O)Oc3ccccc3)n2)nc2ccccc21] |
| 16 |  | 30% | 7.95 (d, J = 8.4 Hz, 1H), 7.73-7.68 (m, 1H), 7.64-7.60 (m, 1H), 7.35-7.27 (m, 4H), 7.06 (t, J = 6.7 Hz, 1H), 5.59 (s, 2H), 4.18 (t, J = 6.7 Hz, 2H), 4.04 (s, 3H), 1.75-1.68 (m, 2H), 1.40-1.33 (m, 4H), 0.95-0.87 (m, 3H). | 3.44 (A) | 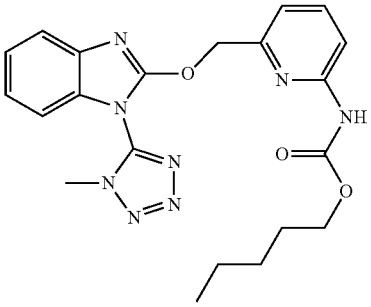 [SMILES: CCCCCOC(=O)Nc1cccc(COc2nc3ccccc3n2-c2nnnn2C)n1] |
| 17 |  | 33% | 7.96 (d, J = 8.3 Hz, 1H), 7.73-7.67 (m, 1H), 7.62 (d, J = 8.0 Hz, 1H), 7.35-7.27 (m, 4H), 7.06 (t, J = 5.3 Hz, 1H), 5.59 (s, 2H), 5.03 (heptet, J = 6.3 Hz, 1H), 4.05 (s, 3H), 1.31 (d, J = 6.3 Hz, 6H). | 3.02 (A) | 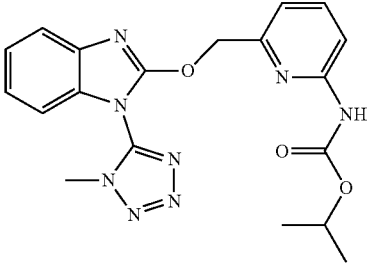 [SMILES: CC(C)OC(=O)Nc1cccc(COc2nc3ccccc3n2-c2nnnn2C)n1] |
| 18 | 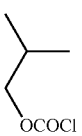 | 37% | 7.96 (d, J = 8.4 Hz, 1H), 7.71 (t, J = 7.9 Hz, 1H), 7.62 (d, J = 7.9 Hz, 1H), 7.35-7.27 (m, 4H), 7.07 (d, J = 7.3 Hz, 1H), 5.60 (s, 2H), 4.04 (s, 3H), 3.97 (d, J = 6.6 Hz, 2H), 1.99 (heptet, J = 6.7 Hz, 1H), 0.97 (d, J = 6.7 Hz, 6H). | 3.23 (A) | 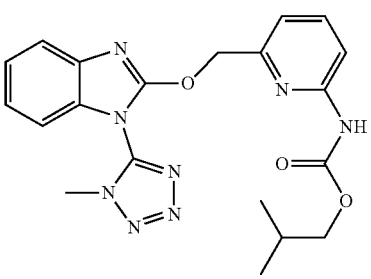 [SMILES: CC(C)COC(=O)Nc1cccc(COc2nc3ccccc3n2-c2nnnn2C)n1] |
| 19 |  | 26% | 7.96 (d, J = 8.4 Hz, 1H), 7.71 (t, J = 7.9 Hz, 1H), 7.62 (d, J = 7.9 Hz, 1H), 7.40-7.26 (m, 4H), 7.08 (d, J = 7.5 Hz, 1H), 6.02-5.90 (m, 1H), 5.60 (s, 2H), 5.38 (d, J = 17.3 Hz, 1H), 5.28 (d, J = 10.4 Hz, 1H), 4.69 (d, J = 5.6 Hz, 2H), 4.05 (s, 3H). | 2.98 (A) | 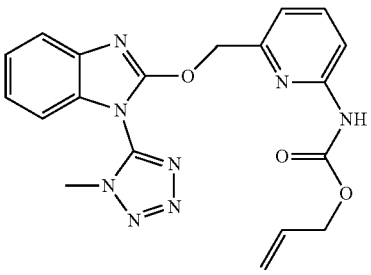 [SMILES: C=CCOC(=O)Nc1cccc(COc2nc3ccccc3n2-c2nnnn2C)n1] |

| Ex. | R'OCOCl | Yield | $^1$H NMR δ(CDCl$_3$) | RT[a] | Structure |
|---|---|---|---|---|---|
| 20[b] | (methoxyethyl chloroformate structure) | 13% | 7.96 (d, J = 8.4 Hz, 1H), 7.72 (t, J = 7.9 Hz, 1H), 7.62 (d, J = 8.0 Hz, 1H), 7.42 (s, 1H), 7.35-7.27 (m, 3H), 7.08 (d, J = 7.5 Hz, 1H), 5.59 (s, 2H), 4.38-4.32 (m, 2H), 4.05 (s, 3H), 3.67-3.63 (m, 2H), 3.42 (s, 3H). | 2.63 (A) | (structure) |
| 21 | (propyl chloroformate structure) | 53% | 7.96 (d, J = 8.4 Hz, 1H), 7.71 (t, J = 7.9 Hz, 1H), 7.62 (d, J = 7.9 Hz, 1H), 7.35-7.23 (m, 4H), 7.07 (d, J = 7.4 Hz, 1H), 5.60 (s, 2H), 4.15 (t, J = 6.7 Hz, 2H), 4.04 (s, 3H), 1.76-1.67 (m, 2H), 0.98 (t, J = 7.4 Hz, 3H). | 3.06 (A) | (structure) |

[a]RT = LCMS retention time in minutes using indicated Method (A-F);
[b]Final purification was by HPLC (basic eluent);
[c]Alternatively Example 13 was prepared in 48% yield by the method of Example 5 using S and N1 as starting materials.

Example 22—2-Cyclopentyl-N-(6-(((1-(1-methyl-1H-tetrazol-5-yl)-1H-benzo[d]imidazol-2-yl)oxy)methyl)pyridin-2-yl)acetamide 22

22

Cyclopentylacetyl chloride (23 mg, 0.16 mmol) was added to a solution of 6-(((1-(1-methyl-1H-tetrazol-5-yl)-1H-benzo[d]imidazol-2-yl)oxy)methyl)pyridin-2-amine T (50 mg, 0.16 mmol) in DCM (0.7 mL) and triethylamine (0.022 ml, 0.16 mmol) and the mixture was stirred at room temperature overnight. The reaction mixture was chromatographed on silica (25 g Puriflash cartridge) eluting with 40-100% EtOAc/PE to give 2-cyclopentyl-N-(6-(((1-(1-methyl-1H-tetrazol-5-yl)-1H-benzo[d]imidazol-2-yl)oxy)methyl)pyridin-2-yl)acetamide 22 (50 mg, 75%) as a white solid.

$^1$H NMR (500 MHz, CDCl$_3$) δ 8.17 (d, J=8.3 Hz, 1H), 7.98 (s, 1H), 7.73-7.66 (m, 1H), 7.63-7.57 (m, 1H), 7.32 (ddd, J=7.9, 6.8, 1.8 Hz, 1H), 7.30-7.26 (m, 2H), 7.10-7.05 (m, 1H), 5.61 (s, 2H), 4.05 (s, 3H), 2.42 (d, J=7.5 Hz, 2H), 2.36-2.26 (m, 1H), 1.90-1.82 (m, 2H), 1.68-1.62 (m, 2H), 1.60-1.51 (m, 2H), 1.23-1.15 (m, 2H); LCMS (method A): 3.23 min (433.2, MH$^+$).

Following the procedure of Example 22, using the appropriate starting materials there were obtained the following Examples (Ex. 23-36):

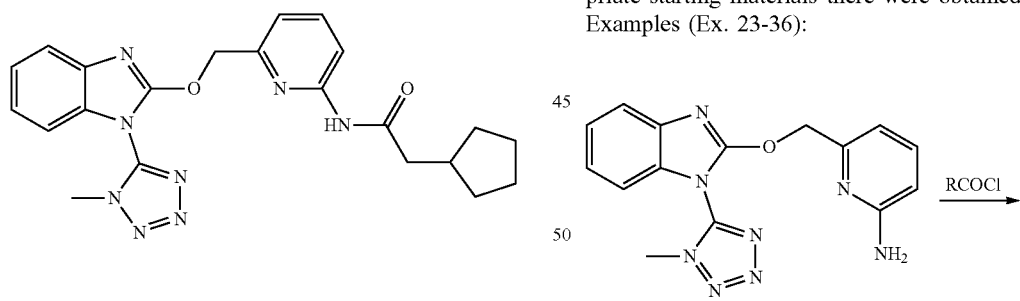

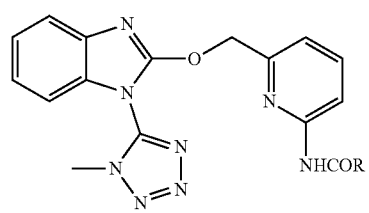

| Ex. | RCOCl | Yield | $^1$H NMR δ(CDCl$_3$) | RT$^a$ | Structure |
|---|---|---|---|---|---|
| 23$^{b,c,d}$ | cyclopentyl-COCl | 18% | 8.18 (d, J = 8.3 Hz, 1H), 7.94 (s, 1H), 7.75-7.67 (m, 1H), 7.63-7.56 (m, 1H), 7.32 (ddd, J = 7.9, 6.9, 1.8 Hz, 1H), 7.29 (ddd, J = 8.0, 1.8, 0.7 Hz, 1H), 7.26 (dd, J = 14.9, 1.1 Hz, 1H), 7.07 (d, J = 6.9 Hz, 1H), 5.61 (s, 2H), 4.05 (s, 3H), 2.76 (p, J = 8.1 Hz, 1H), 2.04-1.93 (m, 2H), 1.92-1.83 (m, 2H), 1.82-1.73 (m, 2H), 1.66-1.62 (m, 2H) | 1.87 (A) | |
| 24$^{b,d}$ | PhCH$_2$OCH$_2$OCOCl | 9% | 8.87 (s, 1H), 8.22 (d, J = 8.3 Hz, 1H), 7.74 (dd, J = 15.4, 7.5 Hz, 1H), 7.64-7.58 (m, 1H), 7.41-7.27 (m, 8H), 7.16 (d, J = 7.2 Hz, 1H), 5.61 (s, 2H), 4.67 (s, 2H), 4.11 (s, 2H), 3.99 (s, 3H) | 8.20 (C) | |
| 25$^{b,c,e}$ | PhOCH$_2$COCl | 49% | 8.86 (s, 1H), 8.27 (d, J = 8.1 Hz, 1H), 7.78 (t, J = 7.9 Hz, 1H), 7.65-7.57 (m, 1H), 7.36 (ddd, J = 6.7, 5.6, 1.9 Hz, 2H), 7.33-7.27 (m, 2H), 7.25 (d, J = 5.8 Hz, 1H), 7.19 (d, J = 7.0 Hz, 1H), 7.11-7.04 (m, 1H), 7.03-6.93 (m, 2H), 5.63 (s, 2H), 4.64 (s, 2H), 4.01 (s, 3H) | 1.86 (E) | |
| 26$^{b,c}$ | cyclopentyl-CH$_2$CH$_2$COCl | 46% | 8.17 (d, J = 8.3 Hz, 1H), 8.02 (s, 1H), 7.47-7.67 (m, 1H), 7.64-7.57 (m, 1H), 7.37-7.27 (m, 2H), 7.07 (d, J = 6.9 Hz, 1H), 5.61 (s, 2H), 4.05 (s, 3H), 2.45-2.40 (m, 2H), 1.85-1.76 (m, 3H), 1.76-1.71 (m, 2H), 1.63-1.57 (m, 2H), 1.52 (tdd, J = 6.6, 5.1, 2.7 Hz, 2H), 1.18-1.06 (m, 2H) | 2.04 (E) | |

| Ex. | RCOCl | Yield | $^1$H NMR δ(CDCl$_3$) | RT$^a$ | Structure |
|---|---|---|---|---|---|
| 27$^{c,d}$ |  | 32% | 8.61 (s, 1H), 8.37 (d, J = 8.3 Hz, 1H), 7.98-7.91 (m, 2H), 7.78 (t, J = 7.9 Hz, 1H), 7.60 (ddt, J = 6.6, 2.6, 1.1 Hz, 2H), 7.56-7.51 (m, 2H), 7.33 (ddd, J = 7.9, 6.7, 2.0 Hz, 1H), 7.29 (ddd, J = 9.3, 2.6, 0.9 Hz, 2H), 7.15 (d, J = 7.3 Hz, 1H), 5.65 (s, 2H), 4.06 (s, 3H) | 3.02 (A) | 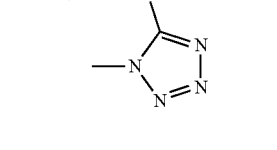 |
| 28 |  | 100% | 8.19 (d, J = 8.4 Hz, 2H), 7.71 (t, J = 7.9 Hz, 1H), 7.64-7.58 (m, 1H), 7.33 (ddd, J = 8.0, 6.7, 2.0 Hz, 1H), 7.30-7.26 (m, 2H), 7.08 (d, J = 7.2 Hz, 1H), 5.62 (s, 2H), 4.05 (s, 3H), 2.46 (q, J = 7.5 Hz, 2H), 1.24 (t, J = 7.5 Hz, 3H) | 2.61 (A) | 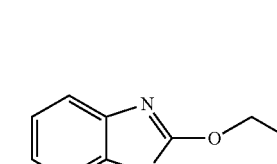 |
| 29$^d$ |  | 20% | 8.17 (d, J = 8.3 Hz, 1H), 7.85 (s, 1H), 7.72-7.65 (m, 1H), 7.61-7.56 (m, 1H), 7.44-7.37 (m, 2H), 7.34 (dd, J = 7.5, 2.1 Hz, 3H), 7.33-7.26 (m, 3H), 7.07 (d, J = 7.0 Hz, 1H), 5.56 (s, 2H), 3.95 (s, 3H), 3.77 (s, 2H) | 3.05 (A) | 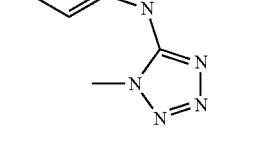 |
| 30 | 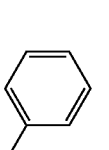 | 82% | 8.18 (d, J = 8.3 Hz, 1H), 8.05 (s, 1H), 7.70 (t, J = 7.9 Hz, 1H), 7.65-7.57 (m, 1H), 7.35-7.26 (m, 3H), 7.07 (d, J = 7.4 Hz, 1H), 5.61 (s, 2H), 4.05 (s, 3H), 2.40 (t, J = 7.4 Hz, 2H), 1.81-1.71 (m, 2H), 1.00 (t, J = 7.4 Hz, 3H) | 2.80 (A) | 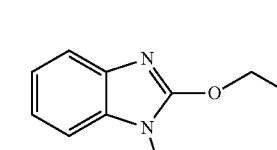 |
| 31 |  | 65% | 8.18 (d, J = 8.3 Hz, 1H), 8.07 (s, 1H), 7.71 (t, J = 7.9 Hz, 1H), 7.64-7.57 (m, 1H), 7.33 (ddd, J = 7.9, 6.7, 2.0 Hz, 1H), 7.30-7.26 (m, 2H), 7.08 (d, J = 7.3 Hz, 1H), 5.62 (s, 2H), 4.05 (s, 3H), 2.44-2.40 (m, 2H), 1.75-1.67 (m, 2H), 1.45-1.36 (m, 2H), 0.94 (t, J = 7.4 Hz, 3H) | 3.02 (A) | 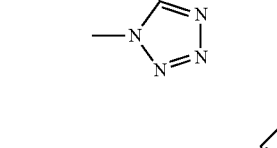 |

-continued

| Ex. | RCOCl | Yield | $^1$H NMR δ(CDCl$_3$) | RT$^a$ | Structure |
|---|---|---|---|---|---|
| 32 | cyclopropane-COCl | 34% | 8.21 (s, 1H), 8.13 (d, J = 8.3 Hz, 1H), 7.72-7.64 (m, 1H), 7.63-7.59 (m, 1H), 7.35-7.31 (m, 1H), 7.30-7.26 (m, 2H), 7.06 (d, J = 7.4 Hz, 1H), 5.62 (s, 2H), 4.05 (s, 3H), 1.61-1.58 (m, 1H), 1.13-1.06 (m, 2H), 0.95-0.88 (m, 2H) | 2.73 (A) | 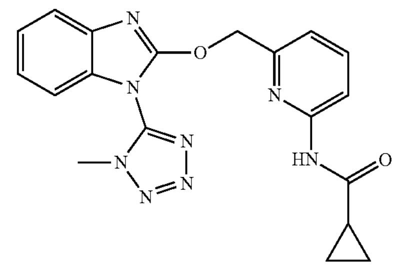 [SMILES: Cn1nnnc1-n1c(OCc2cccc(NC(=O)C3CC3)n2)nc2ccccc21] |
| 33 | MeOCH$_2$COCl | 76% | 8.81 (s, 1H), 8.21 (d, J = 8.1 Hz, 1H), 7.73 (t, J = 7.9 Hz, 1H), 7.62-7.57 (m, 1H), 7.31 (ddd, J = 7.9, 7.1, 1.6 Hz, 1H), 7.27 (ddd, J = 8.0, 1.6, 0.6 Hz, 1H), 7.26-7.22 (m, 1H), 7.17-7.14 (m, 1H), 5.61 (s, 2H), 4.05 (s, 3H), 4.02 (s, 2H), 3.50 (s, 3H) | 2.53 (A) | 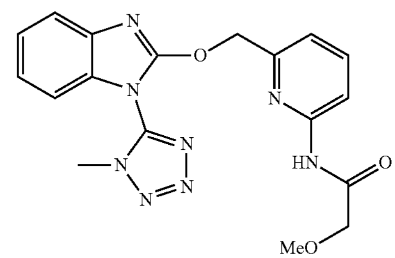 [SMILES: COCC(=O)Nc1cccc(COc2nc3ccccc3n2-c2nnnn2C)n1] |
| 34 | 4-MeO-C$_6$H$_4$-COCl | 97% | 8.58 (s, 1H), 8.34 (d, J = 8.3 Hz, 1H), 7.97-7.90 (m, 2H), 7.75 (t, J = 7.9 Hz, 1H), 7.65-7.57 (m, 1H), 7.34-7.29 (m, 1H), 7.29-7.26 (m, 2H), 7.12 (d, J = 7.4 Hz, 1H), 7.02-6.95 (m, 2H), 5.64 (s, 2H), 4.05 (s, 3H), 3.88 (s, 3H) | 2.97 (A) | 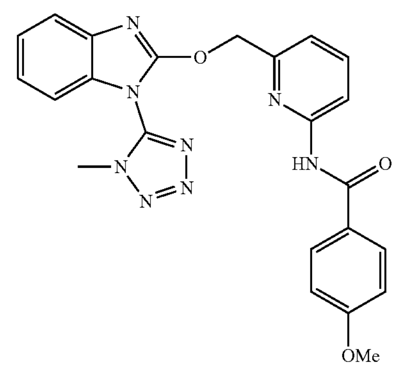 [SMILES: COc1ccc(C(=O)Nc2cccc(COc3nc4ccccc4n3-c3nnnn3C)n2)cc1] |
| 35 | cyclohexane-COCl | 96% | 8.19 (d, J = 8.3 Hz, 1H), 8.01 (s, 1H), 7.70 (t, J = 7.9 Hz, 1H), 7.64-7.58 (m, 1H), 7.34-7.30 (m, 1H), 7.30-7.24 (m, 2H), 7.08 (d, J = 7.4 Hz, 1H), 5.62 (s, 2H), 4.04 (s, 3H), 2.30 (m, 1H), 1.99-1.92 (m, 2H), 1.89-1.79 (m, 2H), 1.77-1.63 (m, 2H), 1.59-1.48 (m, 2H), 1.36-1.28 (m, 2H) | 3.32 (A) | 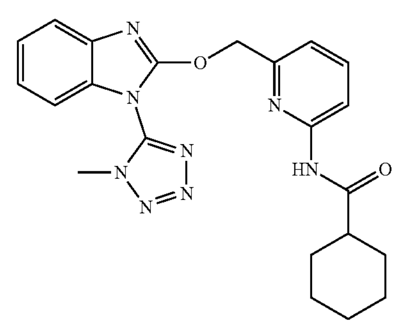 [SMILES: Cn1nnnc1-n1c(OCc2cccc(NC(=O)C3CCCCC3)n2)nc2ccccc21] |

| Ex. | RCOCl | Yield | $^1$H NMR δ(CDCl$_3$) | RT$^a$ | Structure |
|---|---|---|---|---|---|
| 36$^f$ | (structure with COCl) | 76% | 8.22 (d, J = 8.3 Hz, 1H), 7.99 (s, 1H), 7.70 (t, J = 7.9 Hz, 1H), 7.60 (dd, J = 7.1, 0.8 Hz, 1H), 7.34-7.29 (m, 1H), 7.28-7.24 (m, 2H), 7.08 (d, J = 7.4 Hz, 1H), 5.62 (s, 2H), 4.05 (s, 3H), 2.19-2.10 (m, 1H), 1.76-1.66 (m, 2H), 1.61-1.54 (m, 2H), 0.93 (t, J = 7.4 Hz, 6H) | 3.08 (A) | (structure) |

$^a$RT = LCMS retention time in minutes using indicated Method (A-F);
$^b$Reaction time is 6 hours;
$^c$A standard aqueous work-up, extracting product into EtOAc or DCM, was conducted before flash chromatography;
$^d$Final purification by HPLC (basic eluent) gave the pure compound;
$^e$Alternatively Example 25 was prepared in 72% yield by the method of Example 5 using S and D1 as starting materials;
$^f$Reaction time is 3 hours.

Example 37—N-(6-(((1-(1-Methyl-1H-tetrazol-5-yl)-1H-benzo[d]imidazol-2-yl)oxy)methyl)pyridin-2-yl)acetamide 37

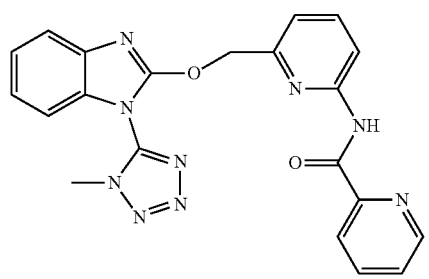

HATU (118 mg, 0.310 mmol) was added to a solution of picolinic acid (38 mg, 0.31 mmol), 6-(((1-(1-methyl-1H-tetrazol-5-yl)-1H-benzo[d]imidazol-2-yl)oxy)methyl)pyridin-2-amine T (100 mg, 0.31 mmol) and N,N-diisopropylethylamine (270 mL, 1.6 mmol) in THF (1 mL). The reaction mixture was stirred for 16 h then was chromatographed on silica (12 g Puriflash cartridge) eluting with 40-100% EtOAc/PE to give N-(6-(((1-(1-methyl-1H-tetrazol-5-yl)-1H-benzo[d]imidazol-2-yl)oxy)methyl)pyridin-2-yl)picolinamide 37 (97 mg, 73%) as a white solid.

$^1$H NMR (500 MHz, CDCl$_3$) δ 10.51 (s, 1H), 8.66 (ddd, J=4.7, 1.6, 0.9 Hz, 1H), 8.41 (d, J=8.0 Hz, 1H), 8.29 (dt, J=7.8, 1.0 Hz, 1H), 7.93 (td, J=7.7, 1.7 Hz, 1H), 7.80 (t, J=7.9 Hz, 1H), 7.70-7.57 (m, 1H), 7.52 (ddd, J=7.6, 4.8, 1.2 Hz, 1H), 7.35-7.28 (m, 2H), 7.27-7.24 (m, 1H), 7.18 (s, 1H), 5.67 (s, 2H), 4.12 (s, 3H); LCMS (method A): 3.08 min (428.1, MH$^+$).

Following the procedure of Example 37, using the appropriate starting materials there were obtained the following Examples 38-51:

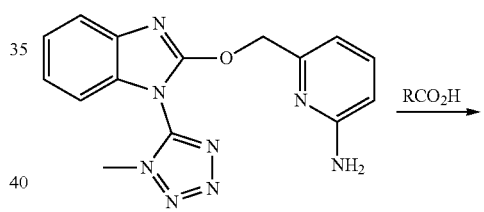

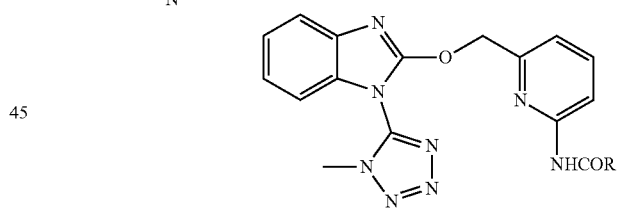

| Ex. | R' | Yield | $^1$H NMR δ(CDCl$_3$) | RT$^a$ | Structure |
|---|---|---|---|---|---|
| 38$^{b,c}$ | (pyridyl-CH$_2$-CO$_2$H) | 32% | 10.16 (s, 1H), 8.58 (ddd, J = 5.0, 1.8, 0.9 Hz, 1H), 8.18 (d, J = 8.2 Hz, 1H), 7.76-7.68 (m, 2H), 7.64-7.59 (m, 1H), 7.36-7.29 (m, 3H), 7.29-7.26 (m, 2H), 7.10 (d, J = 6.8 Hz, 1H), 5.63 (s, 2H), 4.10 (s, 3H), 3.93 (s, 2H) | 2.57 (A) | (structure) |

-continued

| Ex. | R' | Yield | ¹H NMR δ(CDCl₃) | RT[a] | Structure |
|---|---|---|---|---|---|
| 39[b,d] | SMe-CH₂-CO₂H | 38% | 9.12 (s, 1H), 8.19 (d, J = 8.3 Hz, 1H), 7.75 (t, J = 7.9 Hz, 1H), 7.62 (d, J = 7.9 Hz, 1H), 7.36-7.26 (m, 3H), 7.15 (d, J = 7.6 Hz, 1H), 5.64 (s, 2H), 4.10 (s, 3H), 3.37 (s, 2H), 2.20 (s, 3H) | 2.72 (A) | 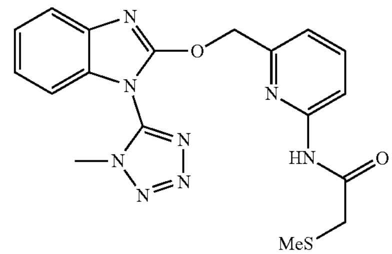 [SMILES: CSCC(=O)Nc1cccc(COc2nc3ccccc3n2-c2nnnn2C)n1] |
| 40[b,d] | cyclopropyl-CH₂-CO₂H | 19% | 8.29 (s, 1H), 8.21 (d, J = 8.3 Hz, 1H), 7.72 (t, J = 7.9 Hz, 1H), 7.61 (d, J = 7.9 Hz, 1H), 7.35-7.31 (m, 1H), 7.30-7.26 (m, 2H), 7.10 (d, J = 7.2 Hz, 1H), 5.63 (s, 2H), 4.06 (s, 3H), 2.36 (d, J = 7.2 Hz, 2H), 1.15-1.06 (m, 1H), 0.70 (ddd, J = 8.0, 5.8, 4.6 Hz, 2H), 0.30 (q, J = 4.7 Hz, 2H) | 2.82 (A) | 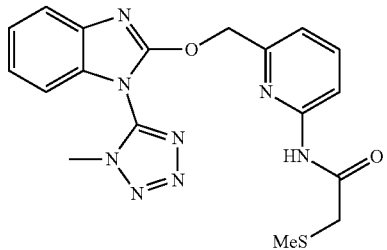 |
| 41[b,d] | MeS-CH₂CH₂-CO₂H | 17% | 8.41 (s, 1H), 8.18 (d, J = 8.5 Hz, 1H), 7.73 (t, J = 7.9 Hz, 1H), 7.61 (d, J = 7.9 Hz, 1H), 7.35-7.30 (m, 1H), 7.27 (dd, J = 6.6, 3.8 Hz, 2H), 7.08 (d, J = 7.6 Hz, 1H), 5.64 (s, 2H), 4.07 (s, 3H), 2.88 (t, J = 7.1 Hz, 2H), 2.74 (t, J = 7.0 Hz, 2H), 2.17 (s, 3H) | 2.80 (A) | 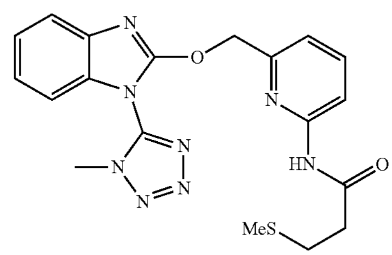 |
| 42 | MeO-CH₂CH₂-CO₂H | 9% | 8.68 (s, 1H), 8.18 (d, J = 8.3 Hz, 1H), 7.77-7.67 (m, 1H), 7.65-7.56 (m, 1H), 7.35-7.26 (m, 3H), 7.09 (d, J = 7.1 Hz, 1H), 5.62 (s, 2H), 4.07 (s, 3H), 3.77-3.69 (m, 2H), 3.41 (s, 3H), 2.71-2.63 (m, 2H) | 1.56 (E) | 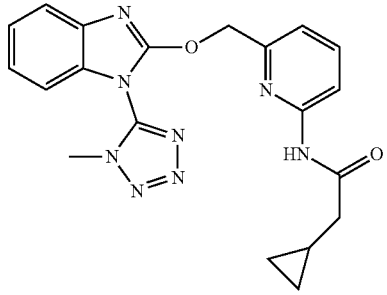 [SMILES: Cn1nnnc1-n1c(OCc2cccc(NC(=O)CC3CC3)n2)nc2ccccc21] |
| 43[e] | 4-CN-C₆H₄-COCl | 23% | 11.15 (s, 1H), 8.18-8.10 (m, 3H), 8.03-7.96 (m, 2H), 7.97-7.89 (m, 1H), 7.59 (d, J = 7.4 Hz, 1H), 7.37 (dd, J = 7.3, 0.7 Hz, 1H), 7.31 (ddd, J = 9.1, 5.4, 1.6 Hz, 2H), 7.27-7.21 (m, 1H), 5.68 (s, 2H), 4.11 (s, 3H) | 2.99 (A) | 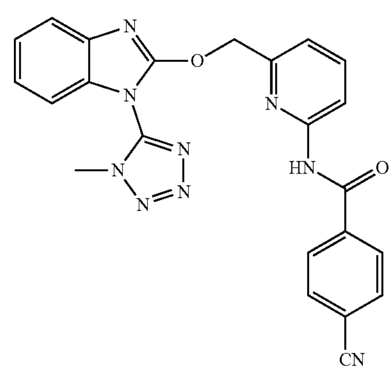 [SMILES: Cn1nnnc1-n1c(OCc2cccc(NC(=O)c3ccc(C#N)cc3)n2)nc2ccccc21] |

-continued

| Ex. | R' | Yield | ¹H NMR δ(CDCl₃) | RT[a] | Structure |
|---|---|---|---|---|---|
| 44[f] | (CH₃)₃C-CH₂-CO₂H (neopentyl carboxylic acid) | 21% | 8.22 (d, J = 8.3 Hz, 1H), 7.73 (t, J = 7.9 Hz, 1H), 7.61 (dt, J = 7.9, 0.9 Hz, 1H), 7.32 (ddd, J = 8.0, 5.9, 2.8 Hz, 1H), 7.28-7.26 (m, 2H), 7.09 (d, J = 7.4 Hz, 1H), 5.63 (s, 2H), 4.06 (s, 3H), 2.29 (s, 2H), 1.09 (s, 9H) | 3.22 (A) | 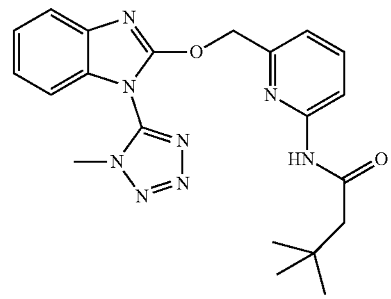 [SMILES: Cn1nnnc1-n1c(OCc2cccc(NC(=O)CC(C)(C)C)n2)nc2ccccc21] |
| 45[f] | (CH₃)₃C-CH₂CH₂-CO₂H | 40% | 8.18 (d, J = 8.4 Hz, 1H), 7.71 (t, J = 7.9 Hz, 1H), 7.61 (d, J = 7.9 Hz, 1H), 7.36-7.30 (m, 1H), 7.27 (d, J = 1.3 Hz, 2H), 7.08 (d, J = 7.4 Hz, 1H), 5.63 (s, 2H), 4.05 (s, 3H), 2.43-2.35 (m, 2H), 1.70-1.63 (m, 2H), 0.94 (s, 9H) | 3.42 (A) | 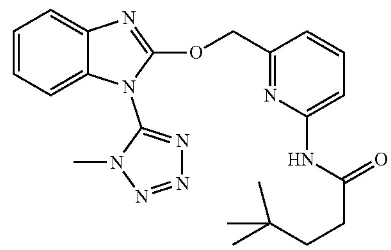 [SMILES: Cn1nnnc1-n1c(OCc2cccc(NC(=O)CCC(C)(C)C)n2)nc2ccccc21] |
| 46[e] | cyclohexyl-CH₂-CO₂H | 29% | 8.18 (d, J = 8.3 Hz, 1H), 7.97 (s, 1H), 7.70 (t, J = 7.9 Hz, 1H), 7.61 (d, J = 7.9 Hz, 1H), 7.35-7.30 (m, 1H), 7.30-7.26 (m, 2H), 7.07 (d, J = 7.4 Hz, 1H), 5.62 (s, 2H), 4.05 (s, 3H), 2.28 (d, J = 7.1 Hz, 2H), 1.92-1.83 (m, 1H), 1.78 (d, J = 13.7 Hz, 2H), 1.73-1.68 (m, 3H), 1.35-1.23 (m, 2H), 1.17 (ddd, J = 16.7, 8.3, 3.6 Hz, 1H), 1.02 (ddd, J = 24.1, 12.4, 3.0 Hz, 2H) | 1.98 (E) | 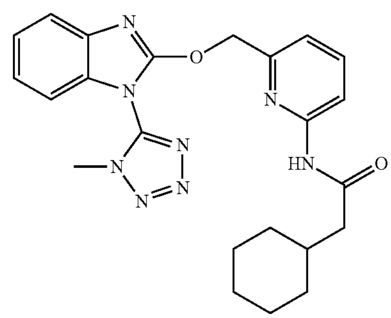 [SMILES: Cn1nnnc1-n1c(OCc2cccc(NC(=O)CC3CCCCC3)n2)nc2ccccc21] |
| 47[e] | cyclohexyl-CH₂CH₂-CO₂H | 13% | 8.17 (d, J = 8.3 Hz, 1H), 7.96 (s, 1H), 7.70 (t, J = 7.9 Hz, 1H), 7.64-7.56 (m, 1H), 7.35-7.30 (m, 1H), 7.29-7.26 (m, 2H), 7.07 (d, J = 7.3 Hz, 1H), 5.62 (s, 2H), 4.04 (s, 3H), 2.45-2.39 (m, 2H), 1.72 (t, J = 12.6 Hz, 4H), 1.65-1.60 (m, 3H), 1.32-1.26 (m, 1H), 1.25-1.15 (m, 3H), 0.98-0.90 (m, 2H) | 3.23 (A) | 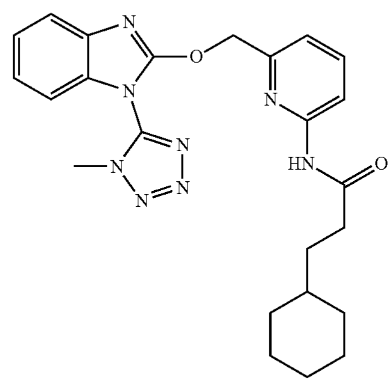 [SMILES: Cn1nnnc1-n1c(OCc2cccc(NC(=O)CCC3CCCCC3)n2)nc2ccccc21] |
| 48[e,g] | HC≡C-CH₂-CO₂H | 7% | 7.61 (d, J = 7.9 Hz, 1H), 7.44 (dd, J = 9.1, 6.8 Hz, 1H), 7.39-7.34 (m, 1H), 7.33 (d, J = 7.7 Hz, 1H), 7.31-7.27 (m, 1H), 7.10 (d, J = 7.8 Hz, 1H), 7.04 (d, J = 7.1 Hz, 1H), 6.36 (s, 1H), 5.84 (s, 2H), 3.93 (s, 3H), 2.65 (s, 3H) | 1.22 (E) | |

-continued

| Ex. | R' | Yield | $^1$H NMR δ(CDCl$_3$) | RT$^a$ | Structure |
|---|---|---|---|---|---|
| 49$^h$ | (isopentyl-CO$_2$H) | 40% | 8.17 (d, J = 8.3 Hz, 1H), 8.05 (s, 1H), 7.70 (t, J = 7.9 Hz, 1H), 7.60 (d, J = 7.9 Hz, 1H), 7.35-7.26 (m, 3H), 7.07 (d, J = 7.4 Hz, 1H), 5.62 (s, 2H), 4.04 (s, 3H), 2.50-2.37 (m, 2H), 1.68-1.56 (m, 3H), 0.93 (d, J = 6.4 Hz, 6H) | 1.89 (E) | |
| 50 | (allyl-CO$_2$H) | 18% | 8.27 and 8.16 (2 × d, J = 8.3 Hz, 1H), 8.02 (s, 1H), 7.71 (t, J = 7.9 Hz, 1H), 7.61 (d, J = 7.9 Hz, 1H), 7.36-7.26 (m, 3H), 7.09 (t, J = 7.3 Hz, 1H), 6.05-5.96 (m, 1H), 5.63 and 5.62 (2 × s, 2H), 5.40-5.29 (m, 1H), 4.055 and 4.05 (2 × s, 3H), 3.22 (d, J = 7.1 Hz, 1H), 1.95 (dd, J = 6.9, 1.5 Hz, 2H) | 1.68 (E) | |
| 51$^h$ | (sec-butyl-CO$_2$H) | 17% | 8.20 (d, J = 8.3 Hz, 1H), 7.95 (s, 1H), 7.70 (t, J = 7.9 Hz, 1H), 7.63-7.57 (m, 1H), 7.35-7.26 (m, 3H), 7.08 (d, J = 7.4 Hz, 1H), 5.62 (s, 2H), 4.05 (s, 3H), 2.43-2.29 (m, 1H), 1.84-1.70 (m, 1H), 1.53 (ddd, J = 13.7, 7.4, 6.3 Hz, 1H), 1.24 (d, J = 6.9 Hz, 3H), 0.95 (t, J = 7.4 Hz, 3H) | 1.81 (E) | |

$^a$RT = LCMS retention time in minutes using indicated Method (A-F);
$^b$DMF was used instead of THF;
$^c$10 equivalents of DIPEA were used instead of 5 equivalents;
$^d$A standard aqueous work-up, extracting product into EtOAc or DCM, was conducted before flash chromatography;
$^e$The reaction was stirred for 3 days; The reaction was stirred at 50° C. for 5 days;
$^g$Final purification by HPLC (basic eluent) gave the pure compound;
$^h$The reaction was stirred at 60° C.

Examples 52 and 53—N-(6-(((1-(1-Methyl-1H-tetrazol-5-yl)-1H-benzo[d]imidazol-2-yl)oxy)methyl)pyridin-2-yl)-2-(methylsulfinyl)acetamide 52 and N-(6-(((1-(1-methyl-1H-tetrazol-5-yl)-1H-benzo[d]imidazol-2-yl)oxy)methyl)pyridin-2-yl)-2-(methylsulfonyl)acetamide 53

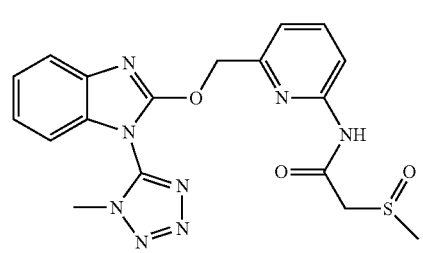

(±)-52

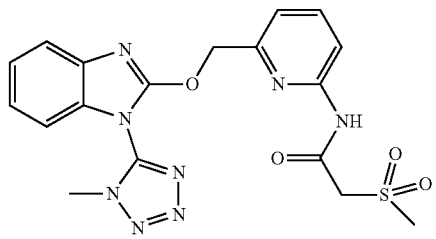

53

A solution of N-(6-(((1-(1-methyl-1H-tetrazol-5-yl)-1H-benzo[d]imidazol-2-yl)oxy)methyl)pyridin-2-yl)-2-(methylthio)acetamide 39 (150 mg, 0.37 mmol) in DCM (2 ml) was treated with 3-chloroperoxybenzoic acid (75% strength, 84 mg, 0.37 mmol), stirred at room temperature for 2 h, then chromatographed on silica (12 g Puriflash cartridge) eluting with 40-100% EtOAc/PE then with 0-50% MeOH/EtOAc to give, respectively: N-(6-(((1-(1-methyl-1H-tetrazol-5-yl)-

1H-benzo[d]imidazol-2-yl)oxy)methyl)pyridin-2-yl)-2-(methylsulfonyl)acetamide 53 (19.5 mg, 12%) as a white solid, $^1$H NMR (500 MHz, CDCl$_3$) δ 8.85 (s, 1H), 8.08 (d, J=8.1 Hz, 1H), 7.75 (t, J=7.9 Hz, 1H), 7.59 (dt, J=7.9, 0.9 Hz, 1H), 7.34-7.30 (m, 1H), 7.29-7.26 (m, 2H), 7.16 (d, J=7.1 Hz, 1H), 5.64 (s, 2H), 4.13 (d, J=1.6 Hz, 3H), 4.11 (d, J=8.3 Hz, 2H), 3.13 (s, 3H); LCMS (method E): 1.49 min (443.2, MH$^+$), and N-(6-(((1-(1-methyl-1H-tetrazol-5-yl)-1H-benzo[d]imidazol-2-yl)oxy)methyl)pyridin-2-yl)-2-(methylsulfinyl)acetamide 52 (105 mg, 67%) as a white solid.

$^1$H NMR (500 MHz, CDCl$_3$) δ 9.42 (s, 1H), 8.11 (d, J=8.3 Hz, 1H), 7.81-7.67 (m, 1H), 7.59 (dt, J=7.6, 0.9 Hz, 1H), 7.33-7.27 (m, 2H), 7.26-7.22 (m, 1H), 7.14 (d, J=7.5 Hz, 1H), 5.61 (s, 2H), 4.17 (s, 3H), 3.90 (d, =14.3 Hz, 1H), 3.43 (d, J=14.3 Hz, 1H), 2.75 (s, 3H); LCMS (method E): 1.40 min (427.2, MH$^+$).

Examples 54-68

Using the method described in Example 5, substituting either or both of alcohol or methylsulphonyl-heterocycle derivative S1 with the appropriate building block (ROH and Het-X in table), using up to 2.5 equiv. NaH with monitoring for at least ca. 70% conversion, and omitting the prep. LC-MS where it was not necessary, there were thus obtained the following Examples (Ex. 54-68)

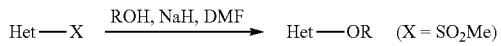

| Ex. | Het-X | ROH | Yield | $^1$H NMR δ(CDCl$_3$) | RT$^a$ | Structure |
|---|---|---|---|---|---|---|
| 54 | S8 | D | 50% | 9.25 (s, 1H), 8.16 (d, J = 8.2 Hz, 1H), 7.76 (t, J = 7.9 Hz, 1H), 7.58 (d, J = 7.8 Hz, 1H), 7.39 (t, J = 7.8 Hz, 2H), 7.31-7.27 (m, 3H), 7.23 (dd, J = 7.9, 1.2 Hz, 1H), 7.21 (d, J = 7.7 Hz, 1H), 7.19-7.15 (m, 2H), 7.10-7.06 (m, 1H), 7.04 (d, J = 1.4 Hz, 1H), 5.65 (s, 2H), 3.54 (s, 3H). | 3.06 (B) | 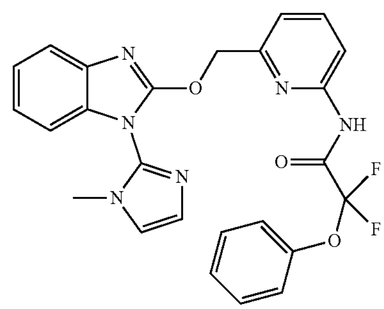 [SMILES: Cn1ccnc1-n1c(OCc2cccc(NC(=O)C(F)(F)Oc3ccccc3)n2)nc2ccccc21] |
| 55 | S9 | D | 48% | 8.86 (s, 1H), 8.24 (d, J = 8.2 Hz, 1H), 7.83 (t, J = 7.9 Hz, 1H), 7.45-7.39 (m, 2H), 7.33-7.28 (m, 3H), 7.24 (d, J = 7.5 Hz, 1H), 6.91-6.83 (m, 2H), 5.68 (s, 2H), 4.07 (s, 3H). | 3.45 (B) | 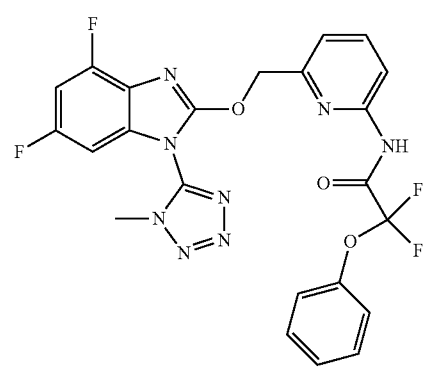 [SMILES: Cn1nnnc1-n1c(OCc2cccc(NC(=O)C(F)(F)Oc3ccccc3)n2)nc2c(F)cc(F)cc21] |
| 56 | S10 | D | 31%$^b$ | 8.82 (s, 1H), 8.67 (d, J = 2.4 Hz, 1H), 8.53 (dd, J = 2.5, 0.5 Hz, 1H), 8.20 (d, J = 8.2 Hz, 1H), 7.79 (t, J = 7.9 Hz, 1H), 7.65 (d, J = 8.0 Hz, 1H), 7.45-7.40 (m, 2H), 7.34-7.27 (m, 4H), 7.23 (d, J = 7.5 Hz, 1H), 7.21-7.17 (m, 1H), 7.02 (d, J = 7.8 Hz, 1H), 5.67 (s, 2H), 2.54 (s, 3H) | 3.25 (B) | 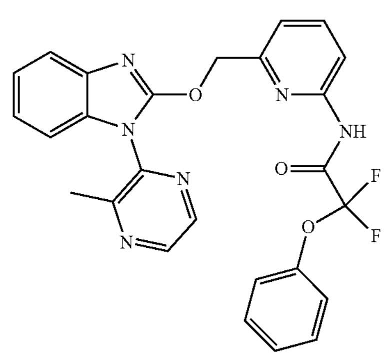 [SMILES: Cc1nccnc1-n1c(OCc2cccc(NC(=O)C(F)(F)Oc3ccccc3)n2)nc2ccccc21] |

| Ex. | Het-X | ROH | Yield | ¹H NMR δ(CDCl₃) | RT$^a$ | Structure |
|---|---|---|---|---|---|---|
| 57 | S8 | N | 78%$^b$ | 7.85 (d, J = 8.4 Hz, 1H), 7.66-7.61 (m, 1H), 7.59 (d, J = 7.8 Hz, 1H), 7.26 (br s, 1H), 7.23 (dd, J = 7.9, 1.2 Hz, 1H), 7.20-7.14 (m, 2H), 7.11-7.08 (m, 1H), 7.03 (dd, J = 4.3, 2.9 Hz, 2H), 5.56 (s, 2H), 3.51 (s, 3H), 1.52 (s, 9H). | 2.82 (B) | 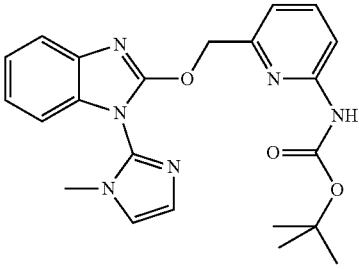 [SMILES: Cn1ccnc1-n1c(OCc2cccc(NC(=O)OC(C)(C)C)n2)nc2ccccc21] |
| 58 | S9 | N | 44%$^b$ | 7.95 (d, J = 8.4 Hz, 1H), 7.72-7.66 (m, 1H), 7.15 (s, 1H), 7.05 (d, J = 7.5 Hz, 1H), 6.92 (ddd, J = 7.7, 2.2, 0.7 Hz, 1H), 6.86 (td, J = 10.0, 2.3 Hz, 1H), 5.59 (s, 2H), 4.06 (s, 3H), 1.53 (s, 9H) | 3.40 (B) | 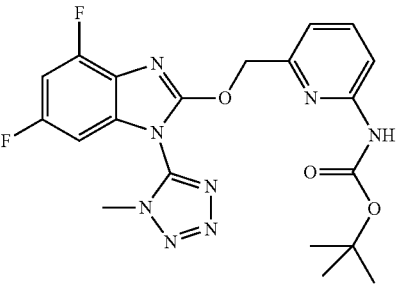 [SMILES: Cn1nnnc1-n1c(OCc2cccc(NC(=O)OC(C)(C)C)n2)nc2c(F)cc(F)cc21] |
| 59 | S10 | N | 40%$^b$ | 8.66 (d, J = 2.4 Hz, 1H), 8.53 (d, J = 2.1 Hz, 1H), 7.88 (d, J = 8.4 Hz, 1H), 7.68-7.62 (m, 2H), 7.30-7.27 (m, 1H), 7.23-7.16 (m, 2H), 7.03 (t, J = 8.5 Hz, 2H), 5.59 (s, 2H), 2.53 (s, 3H), 1.54 (s, 9H) | 3.14 (A) | 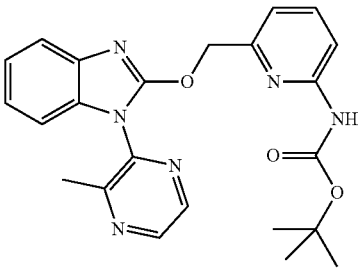 [SMILES: Cc1nccnc1-n1c(OCc2cccc(NC(=O)OC(C)(C)C)n2)nc2ccccc21] |
| 60 | S11 | D | 48%$^{b,d}$ | 8.82 (s, 1H), 8.24 (d, J = 8.2 Hz, 1H), 7.89-7.79 (m, 1H), 7.67 (dd, J = 7.9, 1.1 Hz, 1H), 7.61 (dd, J = 8.1, 1.3 Hz, 2H), 7.41 (ddd, J = 10.1, 5.8, 2.2 Hz, 2H), 7.31 (dt, J = 3.3, 1.4 Hz, 1H), 7.30-7.27 (m, 2H), 7.24 (d, J = 7.3 Hz, 1H), 5.70 (s, 2H), 4.09 (s, 3H) | 8.64 (D) | 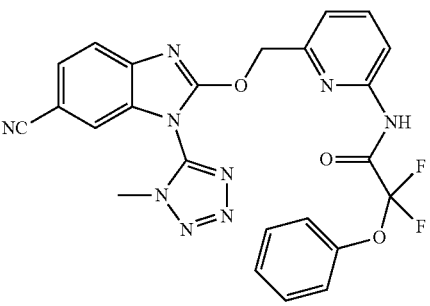 [SMILES: Cn1nnnc1-n1c(OCc2cccc(NC(=O)C(F)(F)Oc3ccccc3)n2)nc2ccc(C#N)cc21] |
| 61 | S12 | D | 42%$^{b,d}$ | 8.76 (s, 1H), 8.15 (d, J = 8.2 Hz, 1H), 7.80 (dd, J = 1.4, 0.5 Hz, 1H), 7.78-7.74 (m, 1H), 7.44 (dd, J = 8.3, 1.5 Hz, 1H), 7.37-7.31 (m, 2H), 7.28 (dd, J = 8.3, 0.5 Hz, 1H), 7.24 (dt, J = 3.3, 1.4 Hz, 1H), 7.21 (s, 1H), 7.19 (d, J = 3.6 Hz, 1H), 7.18 (d, J = 7.5 Hz, 1H), 5.62 (s, 2H), 4.01 (s, 3H) | 3.17 (B) | 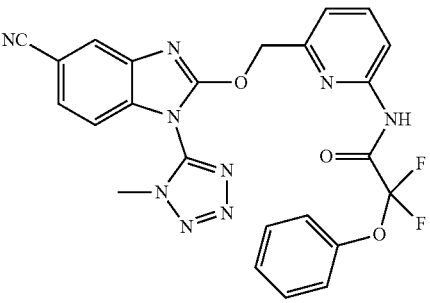 [SMILES: Cn1nnnc1-n1c(OCc2cccc(NC(=O)C(F)(F)Oc3ccccc3)n2)nc2cc(C#N)ccc21] |

-continued

| Ex. | Het-X | ROH | Yield | ¹H NMR δ(CDCl₃) | RT^a | Structure |
|---|---|---|---|---|---|---|
| 62 | S13 | D | 39%^c | 8.85 (s, 1H), 8.65 (dd, J = 4.6, 1.5 Hz, 1H), 8.19-8.13 (m, 2H), 7.76 (t, J = 8.0 Hz, 1H), 7.62 (d, J = 7.9 Hz, 1H), 7.44-7.35 (m, 3H), 7.32-7.26 (m, 4H), 7.25-7.22 (m, 1H), 7.18-7.13 (m, 1H), 7.00 (d, J = 7.9 Hz, 1H), 5.67 (d, J = 13.6 Hz, 1H), 5.63 (d, J = 13.6 Hz, 1H) | 2.20 (F) | 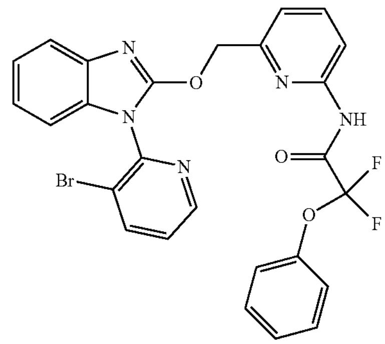 [SMILES: O=C(Nc1cccc(COc2nc3ccccc3n2-c2ncccc2Cl)n1)C(F)(F)Oc1ccccc1] |
| 63 | S14 | D | 36%^{b,d} | 8.83 (s, 1H), 8.60 (dd, J = 4.7, 1.6 Hz, 1H), 8.15 (d, J = 8.2 Hz, 1H), 7.99 (dd, J = 8.1, 1.6 Hz, 1H), 7.76 (t, J = 7.9 Hz, 1H), 7.61 (d, J = 7.9 Hz, 1H), 7.44 (dd, J = 8.1, 4.7 Hz, 1H), 7.42-7.37 (m, 2H), 7.32-7.25 (m, 4H), 7.23 (dd, J = 7.9, 1.1 Hz, 1H), 7.16 (td, J = 7.8, 1.1 Hz, 1H), 7.03 (d, J = 7.6 Hz, 1H), 5.81-5.46 (m, 2H). | 3.53 (B) | 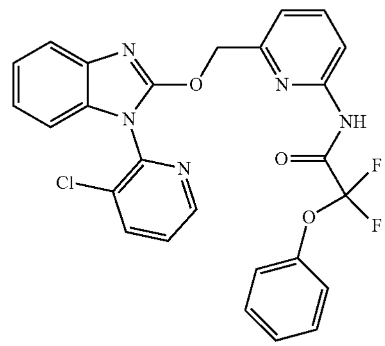 |
| 64 | V | D | 77%^{b,d} | 9.18 (s, 1H), 8.97 (s, 1H), 8.78 (br s, 1H), 8.18 (s, 1H), 7.79 (s, 1H), 7.61 (s, 1H), 7.40 (d, J = 8.3 Hz, 2H), 7.34-7.26 (m, 5H), 7.23-7.16 (m, 2H), 5.66 (s, 2H) | 3.48 (B) | 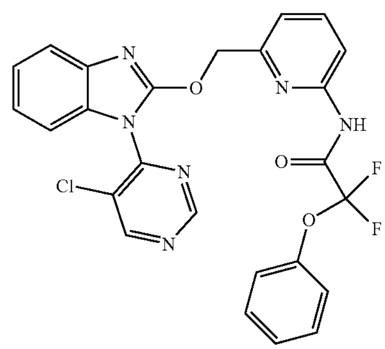 [SMILES: O=C(Nc1cccc(COc2nc3ccccc3n2-c2ncncc2Cl)n1)C(F)(F)Oc1ccccc1] |
| 65 | V1 | D | 77%^{b,e} | 8.92 (s, 1H), 8.83 (br s, 1H), 8.62 (s, 1H), 8.18 (d, J = 8.2 Hz, 1H), 7.78 (t, J = 7.9 Hz, 1H), 7.61-7.57 (m, 1H), 7.43-7.37 (m, 2H), 7.32-7.26 (m, 4H), 7.25-7.21 (m, 1H), 7.21-7.15 (m, 2H), 5.64 (s, 2H), 3.90 (s, 3H) | 3.22 (B) | 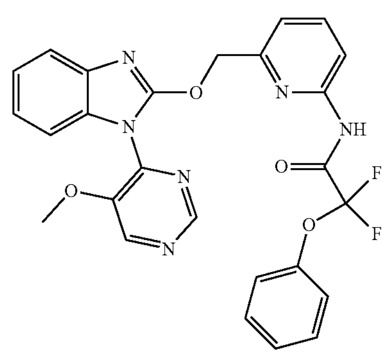 [SMILES: COc1cncnc1-n1c(OCc2cccc(NC(=O)C(F)(F)Oc3ccccc3)n2)nc2ccccc21] |

| Ex. | Het-X | ROH | Yield | ¹H NMR δ(CDCl₃) | RT$^a$ | Structure |
|---|---|---|---|---|---|---|
| 66 | AC | D | 69% | 8.87 (br s, 1H), 8.52 (dd, J = 4.7, 1.3 Hz, 1H), 8.42 (dd, J = 3.7, 1.4 Hz, 1H), 8.17 (d, J = 8.2 Hz, 1H), 7.80 (d, J = 8.3 Hz, 1H), 7.77 (t, J = 8.0 Hz, 1H), 7.44-7.37 (m, 4H), 7.32-7.27 (m, 4H), 7.18-7.12 (m, 1H), 5.74 (s, 2H), 2.23 (s, 3H) | 3.12 (A) | 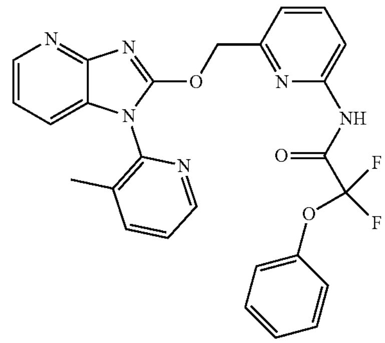 [SMILES: Cc1cccnc1-n1c(OCc2cccc(NC(=O)C(F)(F)Oc3ccccc3)n2)nc2ncccc21] |
| 67 | S2 | D1 | 64% | ¹H NMR (500 MHz, CDCl₃) δ 8.85 (s, 1H), 8.28 (d, J = 8.2 Hz, 1H), 7.80-7.75 (m, 1H), 7.53 (dd, J = 9.4, 4.6 Hz, 1H), 7.36 (dd, J = 8.7, 7.4 Hz, 2H), 7.18 (d, J = 7.5 Hz, 1H), 7.08 (dd, J = 7.4, 1.0 Hz, 1H), 7.06 (dd, J = 4.7, 2.3 Hz, 1H), 7.04 (dd, J = 4.6, 2.3 Hz, 1H), 7.01 (dd, J = 8.8, 0.9 Hz, 2H), 5.61 (s, 2H), 4.65 (s, 2H), 4.01 (s, 3H) | 3.08 (B) | 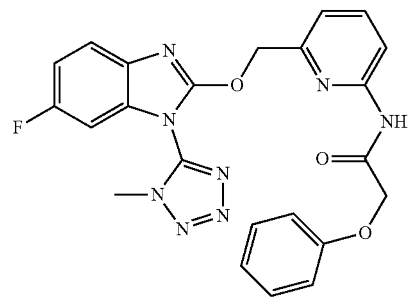 [SMILES: Cn1nnnc1-n1c(OCc2cccc(NC(=O)COc3ccccc3)n2)nc2ccc(F)cc21] |
| 68 | S2 | N1 | 79% | ¹H NMR (500 MHz, CDCl₃) δ 7.96 (d, J = 8.4 Hz, 1H), 7.74-7.68 (m, 1H), 7.53 (ddd, J = 8.2, 4.6, 1.2 Hz, 1H), 7.30 (s, 1H), 7.08-7.01 (m, 3H), 5.57 (s, 2H), 4.19 (t, J = 6.7 Hz, 2H), 4.06 (s, 3H), 1.71-1.63 (m, 2H), 1.47-1.38 (m, 2H), 0.96 (t, J = 7.4 Hz, 3H) | 3.25 (B) | 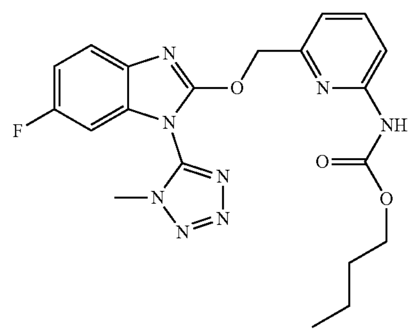 [SMILES: CCCCOC(=O)Nc1cccc(COc2nc3ccc(F)cc3n2-c2nnnn2C)n1] |

$^a$RT = LCMS retention time in minutes using indicated Method (A-D);
$^b$Eluent for chromatography was 0-100% EtOAc/PE;
$^c$Purified by preparative HPLC (acidic eluent);
$^d$Inverse addition, ie. the mixture of NaH and ROH in DMF was added to a cooled solution of Het-X in DMF;
$^e$NaH was added to a cooled solution of both ROH and Het-X in DMF.

Example 69—N-(6-(((3-(5-Chloropyrimidin-4-yl)-1H-indol-2-yl)oxy)methyl)pyridin-2-yl)-2,2-difluoro-2-phenoxyacetamide 69

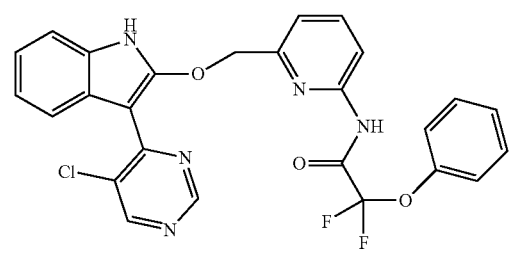

A solution of 3-(5-chloropyrimidin-4-yl)indolin-2-one W (27 mg, 0.11 mmol) in dry DMF (1 mL) was treated with caesium carbonate (50 mg, 0.15 mmol), stirred for 5 min and the resultant orange solution was treated with a solution of (6-(2,2-difluoro-2-phenoxyacetamido)pyridin-2-yl)methyl methanesulfonate X (45 mg, 0.11 mmol) in dry DMF (1 mL), stirred 2 min then heated to 85° C. for 1 h. The mixture was cooled, quenched with saturated aq. NH₄C solution (to pH 7), diluted with EtOAc (20 mL), washed with water (3×20 mL) and brine, dried (MgSO₄) and chromatographed on silica (12 g Puriflash cartridge) eluting with 50-100% PE/Et₂O to give N-(6-(((3-(5-chloropyrimidin-4-yl)-1H-indol-2-yl)oxy)methyl)pyridin-2-yl)-2,2-difluoro-2-phenoxyacetamide 69 (23 mg, 40%), as a pale yellow solid. ¹H NMR (500 MHz, CDCl₃) δ 9.58 (s, 1H), 9.12 (s, 1H), 8.77 (s, 1H), 8.72 (s, 1H), 8.04 (d, J=8.2 Hz, 1H), 7.82 (t, J=7.9 Hz, 1H), 7.73-7.59 (m, 1H), 7.42 (t, J=7.9 Hz, 2H), 7.37-7.27 (m, 5H), 7.23-7.10 (m, 2H), 5.26 (s, 2H); LCMS (Method B): 3.47 min (522.0, MH⁺).

Example 70—2-(4-Fluorophenoxy)-N-(6-(((1-(1-methyl-1H-tetrazol-5-yl)-1H-benzo[d]imidazol-2-yl)oxy)methyl)pyridin-2-yl)acetamide 70

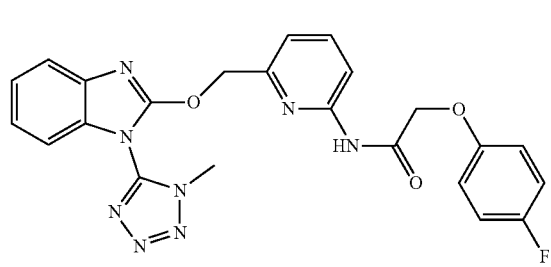

Triethylamine (0.086 mL, 0.62 mmol) and HATU (88 mg, 0.23 mmol) were added to a solution of 6-(((1-(1-methyl-1H-tetrazol-5-yl)-1H-benzo[d]imidazol-2-yl)oxy)methyl)pyridin-2-amine T (50 mg, 0.16 mmol) and (4-fluorophenoxy)acetyl chloride (29 mg, 0.16 mmol) in DCM (1 mL). The mixture was stirred at room temperature for 5 h then was diluted with water (10 mL) and extracted with ethyl acetate (2×10 mL). The organic extracts were combined, washed with water (2×10 mL) and brine, dried (MgSO$_4$) and chromatographed on silica (12 g Claricep cartridge) eluting with 0-100% EtOAc/PE to give 2-(4-fluorophenoxy)-N-(6-(((1-(1-methyl-1H-tetrazol-5-yl)-1H-benzo[d]imidazol-2-yl)oxy)methyl)pyridin-2-yl)acetamide 70 (57 mg, 77%) as a white foam.

$^1$H NMR (500 MHz, CDCl$_3$ plus d$_4$-MeOH) δ 8.21 (d, J=8.3 Hz, 1H), 7.79-7.74 (m, 1H), 7.58 (d, J=8.0 Hz, 1H), 7.30 (ddd, J=8.0, 5.8, 2.8 Hz, 1H), 7.25-7.21 (m, 2H), 7.18 (d, J=7.4 Hz, 1H), 7.04-6.98 (m, 2H), 6.96-6.91 (m, 2H), 5.60 (s, 2H), 4.57 (s, 2H), 4.01 (s, 3H); LCMS (method A): 3.02 min (475.2, MH$^+$).

Example 71—2,2-Difluoro-2-(4-fluorophenoxy)-N-(6-(((1-(1-methyl-1H-tetrazol-5-yl)-1H-benzo[d]imidazol-2-yl)oxy)methyl)pyridin-2-yl)acetamide 71

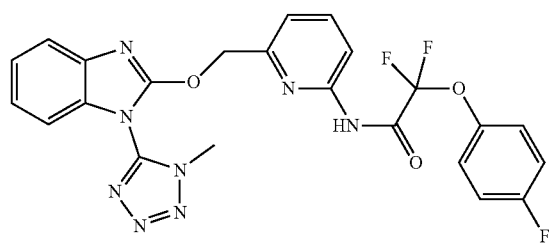

Using the method described in Example 5, except that Intermediates D2 (1 equivalent) was used in place of D, and S was used in place of S1 there was thus obtained 2,2-difluoro-2-(4-fluorophenoxy)-N-(6-(((1-(1-methyl-1H-tetrazol-5-yl)-1H-benzo[d]imidazol-2-yl)oxy)methyl)pyridin-2-yl)acetamide 71 as a white solid (62 mg, 68%).

$^1$H NMR (500 MHz, CDCl$_3$) δ 8.85 (s, 1H), 8.20 (d, J=8.3 Hz, 1H), 7.81 (t, J=7.9 Hz, 1H), 7.61 (d, J=7.9 Hz, 1H), 7.35-7.31 (m, 1H), 7.29-7.26 (m, 2H), 7.24 (dd, J=8.0, 6.7 Hz, 3H), 7.09 (dd, J=9.1, 8.0 Hz, 2H), 5.66 (s, 2H), 4.06 (s, 3H); LCMS (method B): 3.23 min (511.2, MH$^+$).

Example 72—Butyl (6-(((6-bromo-1-(1-methyl-1H-tetrazol-5-yl)-1H-benzo[d]imidazol-2-yl)oxy)methyl)pyridin-2-yl)carbamate 72

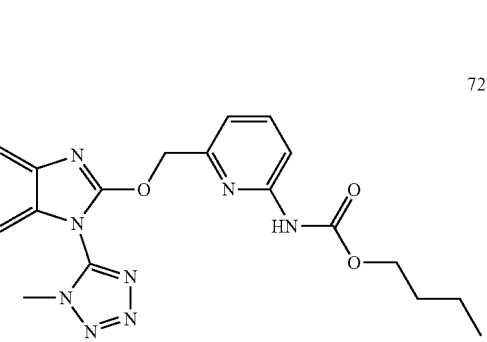

Potassium tert-butoxide (34.7 mg, 0.309 mmol) and 6-bromo-1-(1-methyl-1H-tetrazol-5-yl)-2-(methylsulfonyl)-1H-benzo[d]imidazole S17 (46.0 mg, 0.129 mmol) were added to a solution of butyl (6-(hydroxymethyl)pyridin-2-yl)carbamate N1 (28.9 mg, 0.129 mmol) in THF (2 mL) at 50° C. and the mixture was stirred for 16 h. Saturated aqueous ammonium chloride solution (5 mL) was then added and the mixture was partitioned between EtOAc (25 mL) and water (10 mL). The organic layer was washed further with water (3×20 mL) and brine, dried (MgSO$_4$) and chromatographed (10 g Biotage KP-Sil cartridge) eluting with 0-100% EtOAc/PE then further purified similarly but eluting with 10-60% (0.5% triethylamine/EtOAc)/heptane. The resultant gum crystallised slowly and was then triturated with diethyl ether to give butyl (6-(((6-bromo-1-(1-methyl-1H-tetrazol-5-yl)-1H-benzo[d]imidazol-2-yl)oxy)methyl)pyridin-2-yl)carbamate 72 (4.7 mg, 7%) as a white solid.

$^1$H NMR (500 MHz, CDCl$_3$) δ 7.91 (d, J=8.2 Hz, 1H), 7.70-7.64 (m, 1H), 7.60 (s, 1H), 7.33 (dd, J=8.4, 1.8 Hz, 1H), 7.19 (s, 1H), 6.96 (dd, J=10.0, 8.0 Hz, 2H), 5.07 (s, 2H), 4.22 (s, J=4.9 Hz, 3H), 4.18 (t, J=6.7 Hz, 2H), 1.70-1.62 (m, 2H), 1.47-1.36 (m, 2H), 0.95 (t, J=7.4 Hz, 3H); LCMS (method B): 3.52 min (503.1, MH$^+$).

Example 73—tert-Butyl (6-(((6-bromo-1-(1-methyl-1H-tetrazol-5-yl)-1H-benzo[d]imidazol-2-yl)oxy)methyl)pyridin-2-yl)carbamate 73

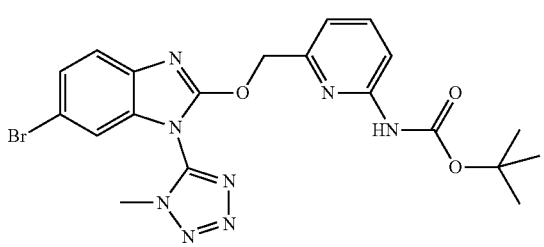

Following the procedure used for Example 72 except that Intermediate N was used as starting material in place of N1 and preparative HPLC (with acidic eluent) was used for purification, there was thus obtained tert-butyl (6-(((6- bromo-1-(1-methyl-1H-tetrazol-5-yl)-1H-benzo[d]imidazol-2-yl)oxy)methyl)pyridin-2-yl)carbamate 73 (2.5 mg, 4%) as a colourless oil.

$^1$H NMR (500 MHz, CDCl$_3$) δ 7.89 (d, J=8.4 Hz, 1H), 7.66 (t, J=7.9 Hz, 1H), 7.60 (s, 1H), 7.33 (dd, J=8.4, 1.8 Hz, 1H), 7.16 (s, 1H), 6.98-6.93 (m, 2H), 5.07 (s, 2H), 4.22 (s, 3H), 1.51 (s, 9H); LCMS (Method B): 3.40 min (403.1, MH$^+$—C$_4$H$_8$—CO$_2$).

Example 74—N-(6-((((6-Bromo-1-(1-methyl-1H-tetrazol-5-yl)-1H-benzo[d]imidazol-2-yl)oxy)methyl)pyridin-2-yl)-2,2-difluoro-2-phenoxyacetamide 74

74

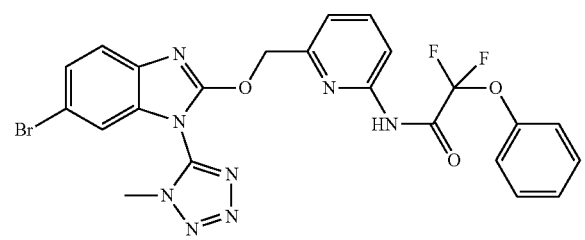

A brine/ice-cooled solution of 2,2-difluoro-N-(6-(hydroxymethyl)pyridin-2-yl)-2-phenoxyacetamide D (42.1 mg, 0.143 mmol) and 6-bromo-1-(1-methyl-1H-tetrazol-5-yl)-2-(phenylsulfonyl)-1H-benzo[d]imidazole V3 (59.7 mg, 0.142 mmol) in dry DMF (1 mL) was treated with a 60% mineral oil dispersion of sodium hydride (11.5 mg, 0.286 mmol), stirred for 45 min then quenched with saturated aqueous ammonium chloride solution (1 mL). The mixture was diluted with EtOAc (15 mL), washed with water (3×15 mL) and brine, dried (MgSO$_4$) and chromatographed on silica (12 g Puriflash cartridge) eluting with 30-70% EtOAc/PE to give N-(6-((((6-bromo-1-(1-methyl-1H-tetrazol-5-yl)-1H-benzo[d]imidazol-2-yl)oxy)methyl)pyridin-2-yl)-2,2-difluoro-2-phenoxyacetamide 74 (30.6 mg, 38%) as a colourless oil.

$^1$H NMR (500 MHz, CDCl$_3$) δ 8.85 (s, 1H), 8.22 (d, J=8.2 Hz, 1H), 7.82 (t, J=7.9 Hz, 1H), 7.49-7.38 (m, 5H), 7.33-7.25 (m, 4H), 7.22 (d, J=7.5 Hz, 1H), 5.65 (s, 2H), 4.06 (s, 3H); LCMS (method B): 3.42 min (571.0, MH$^+$).

Example 75—2-Cyclopentyl-N-(4-(((1-(1-methyl-1H-tetrazol-5-yl)-1H-benzo[d]imidazol-2-yl)oxy)methyl)thiazol-2-yl)acetamide 75

75

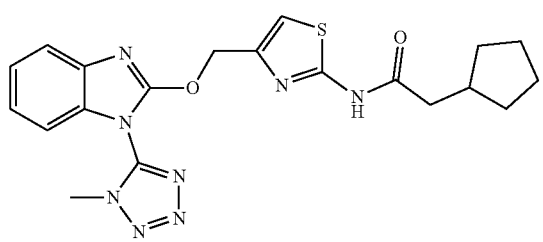

A solution of (2-aminothiazol-4-yl)methanol (40 mg, 0.31 mmol) and 1-(1-methyl-1H-tetrazol-5-yl)-2-(methylsulfonyl)-1H-benzo[d]imidazole (40 mg, 0.14 mmol) in triethylamine (0.5 mL) was heated at 110° C. in a sealed tube for 18 h. The resulting brown gum was chromatographed on silica (12 g Claricep cartridge) eluting with 0-25% MeOH/DCM to give 4-(((1-(1-methyl-1H-tetrazol-5-yl)-1H-benzo[d]imidazol-2-yl)oxy)methyl)thiazol-2-amine (47 mg, not pure). (Analysis of this intermediate: LCMS (method A): 1.76 min (329.0 MH$^+$), used without further purification.) A solution of this material in DCM (0.5 mL) was treated with cyclopentylacetyl chloride (0.019 mL, 0.14 mmol) and triethylamine (0.020 mL, 0.14 mmol) and stirred at RT for 18 h then was chromatographed on silica (12 g Claricep) to give an impure sample of 2-cyclopentyl-N-(4-(((1-(1-methyl-1H-tetrazol-5-yl)-1H-benzo[d]imidazol-2-yl)oxy)methyl)thiazol-2-yl)acetamide 75 (15 mg) as a yellow oil.

LCMS (method A): 2.71 min (439.1 MH$^+$).

Testing the Fungicidal Activity of Compounds of the Invention

The activity of example 1, along with comparative compounds A (see WO2012/136581) and B (WO2016/055802), were tested against certain oomycete fungal plant pathogens.

A

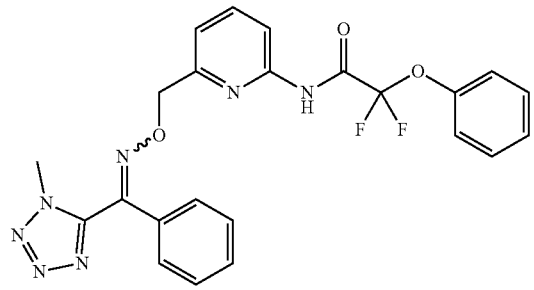

B

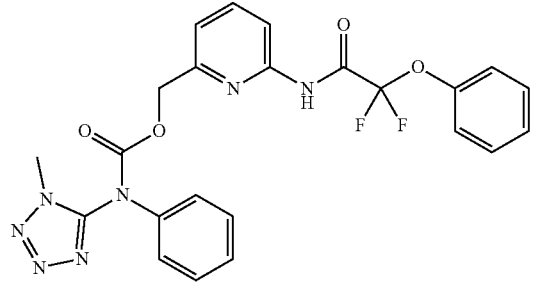

Amended Agar Assay

Testing was carried out on potato dextrose agar (PDA) amended with each compound at test concentrations of 20, 4 and 0.8, 0.16 and 0.032 ppm. Amended agar at each test concentration was poured into three replicate 9 cm petri dishes. Each replicate dish was inoculated in the centre with a 5 mm agar plug taken from the leading edge of a culture aged between 2 and 7 days old; the age of the culture was dependant on the growth rate of the pathogen being tested. The test pathogens were *Pythium ultimum* and *Phytophthora* cinnamomi. Plates were incubated at 18° C. and the diameter of each colony measured before growth on the fastest growing plate reached the plate edge. This varied between 2 and 7 days depending on the growth rate of test pathogens. The % reduction in colony growth compared to the control was calculated for each test concentration and pathogen combination.

The results are shown in Table 1 in which * represents an average control of up to 50% at said dosage;  represents an average control of 50% or greater but less than 80% at said dosage; and * represents an average control of 80% or greater at said dosage.

TABLE 1

| | average % control at given dosage- | | | | | | | | | |
|---|---|---|---|---|---|---|---|---|---|---|
| | Pathogen | | | | | | | | | |
| | Phytophthora cinnamomi | | | | | Pythium ultimum | | | | |
| | Dose | | | | | | | | | |
| | 0.032 | 0.16 | 0.8 | 4 | 20 | 0.032 | 0.16 | 0.8 | 4 | 20 |
| A | *** | *** | *** | *** | *** | *** | *** | *** | *** | *** |
| B | * | ** | ** | ** | ** | * | ** | ** | *** | *** |
| 1 | *** | *** | *** | *** | *** | *** | *** | *** | *** | *** |

Compound 1 exhibited excellent control over the tested oomycete fungal plant pathogens, even at low concentrations A primary screen was also conducted for a number of other compounds of the invention. The screen was conducted at 20 ppm and the results are provided in Table 2, in which D represents no control detected at this concentration; C represents up to 50% control; B from 50 to 99% control; and A represents a control of greater than 99%.

TABLE 2

| | % control at 20 ppm[a] | |
|---|---|---|
| Compound | Pythium ultimum | Phytophthora cinnamomi |
| A | A | A |
| 1 | A | A |
| 3 | B | B |
| 2 | A | A |
| 6 | A | A |
| 4 | B | B |
| 10 | C-B | B |
| 5 | B | C |
| 7 | D | D |
| 8 | C | D |
| 11 | A | B |
| 9 | D | D |
| 62 | C | C |
| 64 | A | nt |
| 66 | B | nt |

C-B represents a control of 45-55%
[a]nt = Not tested.

Thus, many of the compounds of the invention showed good control over the fungal pathogens tested and certain compounds (e.g. examples 1, 2, 6 and 11) showed excellent control.

Alternatively, or in addition, the same assay was conducted at descending test concentrations with 5-fold dilutions typically down to 0.032 ppm, and an $EC_{50}$ (the concentration at which 50% control would be achieved) was determined. The results are provided in Table 1 in which G represents an $EC_{50}$ above 20 ppm, F represents an $EC_{50}$ of 2-20 ppm and E represents and $EC_{50}$ less than 2 ppm.

TABLE 1

| Fungicidal Activity[a] - % control at 20 ppm and $EC_{50}$ | | | | | |
|---|---|---|---|---|---|
| Compound | Pythium ultimum ($EC_{50}$) | Phytophthora cirmamomi ($EC_{50}$) | Compound | Pythium ultimum ($EC_{50}$) | Phytophthora cinnamomi ($EC_{50}$) |
| 1 | E | E | 6 | E | E |
| 2 | E | E | 7 | G | G |
| 3 | E | E | 9 | G | G |
| 4 | E | E | 11 | E | E |
| 12 | E | E | 46 | E | E |

TABLE 1-continued

| Fungicidal Activity[a] - % control at 20 ppm and $EC_{50}$ | | | | | |
|---|---|---|---|---|---|
| Compound | Pythium ultimum ($EC_{50}$) | Phytophthora cirmamomi ($EC_{50}$) | Compound | Pythium ultimum ($EC_{50}$) | Phytophthora cinnamomi ($EC_{50}$) |
| 13 | E | E | 47 | E | E |
| 14 | E | E | 48 | G | G |
| 15 | E | E | 49 | E | E |
| 16 | E | E | 50 | E | E |
| 17 | E | E | 51 | E | E |
| 18 | E | E | 52 | G | F |
| 19 | E | E | 53 | F | E |
| 20 | E | E | 54 | E | E |
| 21 | E | E | 55 | E | E |
| 22 | E | E | 56 | E | F |
| 23 | E | E | 57 | E | E |
| 24 | E | E | 58 | E | E |
| 25 | E | E | 59 | G | G |
| 26 | E | E | 60 | E | E |
| 27 | E | E | 61 | E | E |
| 28 | E | E | 63 | F | F |
| 29 | E | E | 64 | nt | E |
| 30 | E | E | 66 | nt | G |
| 31 | E | E | 69 | G | G |
| 32 | E | E | | | |
| 33 | F | F | | | |
| 34 | E | E | | | |
| 35 | E | E | | | |
| 36 | E | E | | | |
| 37 | E | E | | | |
| 38 | E | E | | | |
| 39 | E | E | | | |
| 40 | E | E | | | |
| 41 | E | E | | | |
| 42 | E | E | | | |
| 43 | E | E | | | |
| 44 | E | E | | | |
| 45 | E | E | | | |

[a]nt = Not tested.

Thus many of the compounds of the invention showed good to excellent control over the fungal pathogens tested.

The invention claimed is:
1. A compound of formula (I):

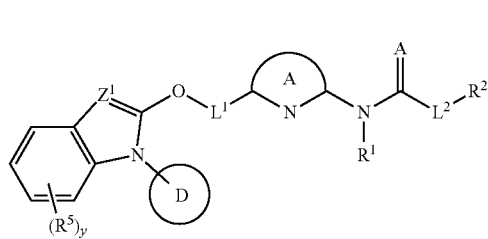

wherein Ring A is independently a 5- or 6-membered heteroaryl ring having a nitrogen in the position indicated, optionally further substituted with 1 to 3 $R^3$ groups;
Ring D is independently selected from the group consisting of 5- or 6-membered heteroaryl and phenyl, optionally further substituted with 1 to 5 $R^6$ groups;
y is an integer from 0 to 4;
$Z^1$ is independently selected from the group consisting of N and CH;
=$A^1$ is selected from the group consisting of =O and =S;
$L^1$- is —$C_1$-$C_3$-alkylene-;
-$L^2$- is absent or is independently selected from the group consisting of —O—, —S— and —$NR^9$—;
$R^9$ and $R^{10}$ are each independently at each occurrence selected from the group consisting of H and substituted or unsubstituted $C_1$-$C_4$-alkyl;
$R^1$ is selected from the group consisting of H and substituted $C_1$-$C_4$-alkyl;
$R^2$ is independently selected from the group consisting of: substituted or unsubstituted $C_1$-$C_6$-alkyl, $C_2$-$C_6$-alkenyl, $C_2$-$C_6$-alkynyl, substituted or unsubstituted $C_3$-$C_6$-cycloalkyl, substituted or unsubstituted 3- to 6-membered heterocycloalkyl, substituted or unsubstituted 5- or 6-membered heteroaryl, substituted or unsubstituted phenyl, —$CR^7R^7L^3R^8$, and substituted or unsubstituted —$C_1$-$C_3$-alkylene-$R^{2a}$; wherein $R^{2a}$ is independently selected from the group consisting of substituted or unsubstituted $C_3$-$C_6$-cycloalkyl, substituted or unsubstituted 3- to 6-membered heterocycloalkyl, substituted or unsubstituted 5- or 6-membered heteroaryl and substituted or unsubstituted phenyl;
-$L^3$- is independently selected from the group consisting of —O—, —S— and —$NR^9$—;
$R^3$, $R^5$ and $R^6$ are each independently at each occurrence selected from the group consisting of: halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, substituted or unsubstituted $C_1$-$C_4$-alkyl, $C_2$-$C_4$-alkenyl, $C_2$-$C_4$-alkynyl, substituted or unsubstituted phenyl, substituted or unsubstituted $C_3$-$C_6$-cycloalkyl, substituted or unsubstituted 3- to 6-membered heterocycloalkyl, substituted or unsubstituted 5- or 6-membered heteroaryl and substituted or unsubstituted C1-C4-haloalkyl;
$R^7$ is independently at each occurrence selected from the group consisting of F, H and substituted or unsubstituted $C_1$-$C_4$-alkyl;
$R^8$ is independently selected from the group consisting of H, substituted or unsubstituted $C_1$-$C_4$-alkyl, $C_3$-$C_4$-alkenyl, $C_3$-$C_4$-alkynyl, $C_3$-$C_6$-cycloalkyl, substituted or unsubstituted 3- to 6-membered heterocycloalkyl, substituted or unsubstituted 5- or 6-membered heteroaryl, substituted or unsubstituted phenyl and substituted or unsubstituted —$C_1$-$C_3$-alkylene-$R^{8a}$; wherein $R^{8a}$ is independently selected from the group consisting of substituted or unsubstituted $C_3$-$C_6$-cycloalkyl, substituted or unsubstituted 3- to 6-membered heterocycloalkyl, substituted or unsubstituted 5- or 6-membered heteroaryl and substituted or unsubstituted phenyl;
$R^{11}$ is independently at each occurrence selected from the group consisting of H, substituted or unsubstituted $C_3$-$C_6$-cycloalkyl, substituted or unsubstituted $C_1$-$C_4$-alkyl, substituted or unsubstituted C(O)—$C_1$-$C_4$-alkyl and substituted or unsubstituted $S(O)_2$—$C_1$-$C_4$-alkyl;
wherein any substituted alkyl, alkylene, haloalkyl, cycloalkyl, heterocycloalkyl, aryl or heteroaryl group substituted, where chemically possible, by 1 to 5 substituents which are each independently selected at each occurrence from the group consisting of: oxo, =$NR^a$, =$NOR^a$, halo, nitro, cyano, $NR^aR^a$, $NR^aS(O)_2R^a$, $NR^aC(O)R^a$, $NR^aCONR^aR^a$, $NR^aCO_2R^a$, $OR^a$, $SR^a$, $S(O)R^a$, $S(O)_2R^a$, $S(O)_2NR^aR^a$, $CO_2R^aC(O)R^a$, $CONR^aR^a$, unsubstituted $C_1$-$C_4$-alkyl, unsubstituted $C_2$-$C_4$-alkenyl, unsubstituted $C_2$-$C_4$-alkynyl and unsubstituted $C_1$-$C_4$-haloalkyl; wherein $R^a$ is independently at each occurrence selected from the group consisting of H, unsubstituted $C_1$-$C_4$ alkyl and unsubstituted $C_1$-$C_4$-haloalkyl;
or an agronomically acceptable salt or N-oxide thereof.
2. A compound of claim 1, wherein the group

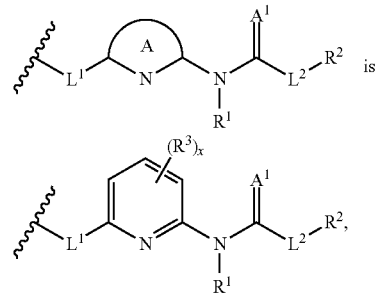

wherein x is an integer from 0 to 3.
3. A compound of claim 1, wherein the group

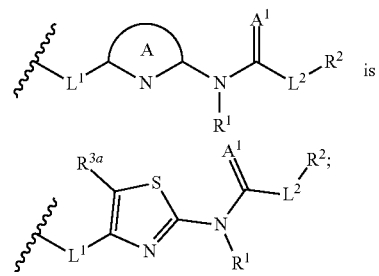

where $R^{3a}$ is independently selected from the group consisting of H and $R^3$.
4. A compound of claim 1, wherein $R^1$ is H.
5. A compound of claim 1, wherein -$L^2$- is absent and $R^2$ is —$CR^7R^7L^3R^8$.
6. A compound of claim 5, wherein -$L^3$- is —O—.

7. A compound of claim 5, wherein $R^7$ is at all occurrences selected from the group consisting of H and F.

8. A compound of claim 5, wherein $R^8$ is independently selected from the group consisting of substituted or unsubstituted $C_1$-$C_4$-alkyl, $C_3$-$C_4$-alkenyl, $C_3$-$C_4$-alkynyl, substituted or unsubstituted $C_3$-$C_6$-cycloalkyl, substituted or unsubstituted 3- to 6-membered heterocycloalkyl, substituted or unsubstituted 5- or 6-membered heteroaryl, substituted or unsubstituted phenyl and substituted or unsubstituted —$C_1$-$C_3$-alkylene-$R^{8a}$; wherein $R^{8a}$ is independently selected from the group consisting of substituted or unsubstituted $C_3$-$C_6$-cycloalkyl, substituted or unsubstituted 3- to 6-membered heterocycloalkyl, substituted or unsubstituted 5- or 6-membered heteroaryl and substituted or unsubstituted phenyl.

9. A compound of claim 1, wherein -$L^2$- is —O— and $R^2$ is independently selected from the group consisting of: substituted or unsubstituted $C_1$-$C_6$-alkyl, $C_3$-$C_6$-alkenyl, $C_3$-$C_6$-alkynyl, substituted or unsubstituted $C_3$-$C_6$-cycloalkyl, substituted or unsubstituted 3- to 6-membered heterocycloalkyl, substituted or unsubstituted 5- or 6-membered heteroaryl, substituted or unsubstituted phenyl and substituted or unsubstituted —$C_1$-$C_3$-alkylene-$R^{2a}$; wherein $R^a$ is independently selected from the group consisting of substituted or unsubstituted $C_3$-$C_6$-cycloalkyl, substituted or unsubstituted 3- to 6-membered heterocycloalkyl, substituted or unsubstituted 5- or 6-membered heteroaryl and substituted or unsubstituted phenyl.

10. A compound of claim 1, wherein -$L^2$- is absent and $R^2$ is independently selected from the group consisting of: substituted or unsubstituted $C_1$-$C_6$-alkyl, $C_2$-$C_6$-alkenyl, $C_2$-$C_6$-alkynyl, substituted or unsubstituted $C_3$-$C_6$-cycloalkyl, substituted or unsubstituted 3- to 6-membered heterocycloalkyl, substituted or unsubstituted 5- or 6-membered heteroaryl, substituted or unsubstituted phenyl and substituted or unsubstituted —$C_1$-$C_3$-alkylene-$R^{2a}$; wherein $R^{2a}$ is independently selected from the group consisting of substituted or unsubstituted $C_3$-$C_6$-cycloalkyl, substituted or unsubstituted 3- to 6-membered heterocycloalkyl, substituted or unsubstituted 5- or 6-membered heteroaryl and substituted or unsubstituted phenyl.

11. A compound of claim 1, wherein -$L^1$- is —$CH_2$—.

12. A compound of claim 1, wherein the group

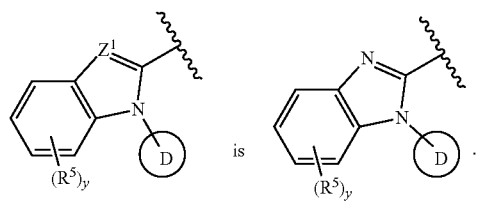

13. A compound of claim 1, wherein Ring D is a 5- or 6-membered heteroaryl group comprising 1, 2, 3 or 4 nitrogen atoms in the ring.

14. A compound of claim 1, wherein the compound of formula (I) is selected from the group of compounds consisting of:

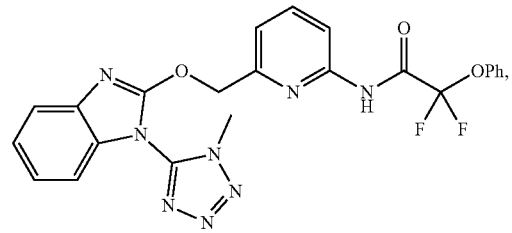

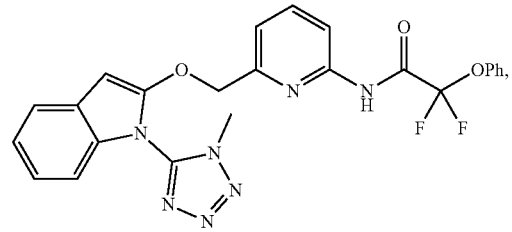

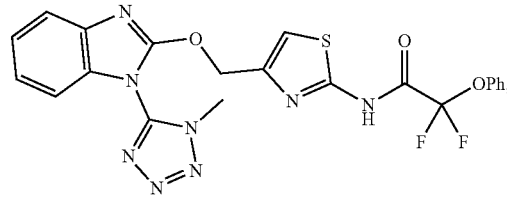

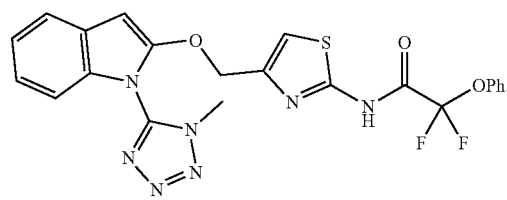

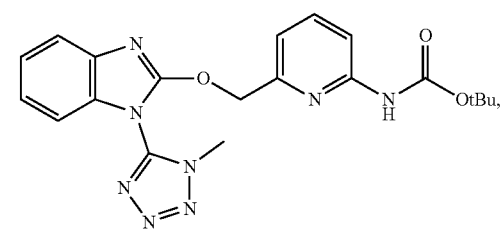

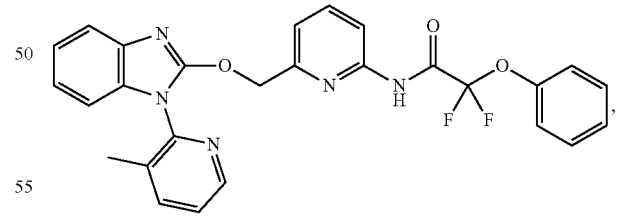

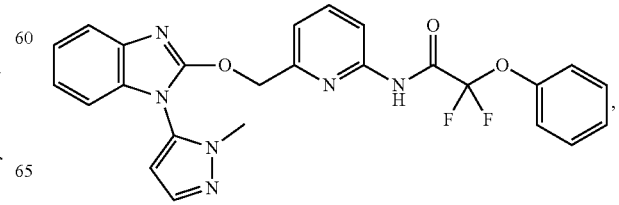

127
-continued
128
-continued
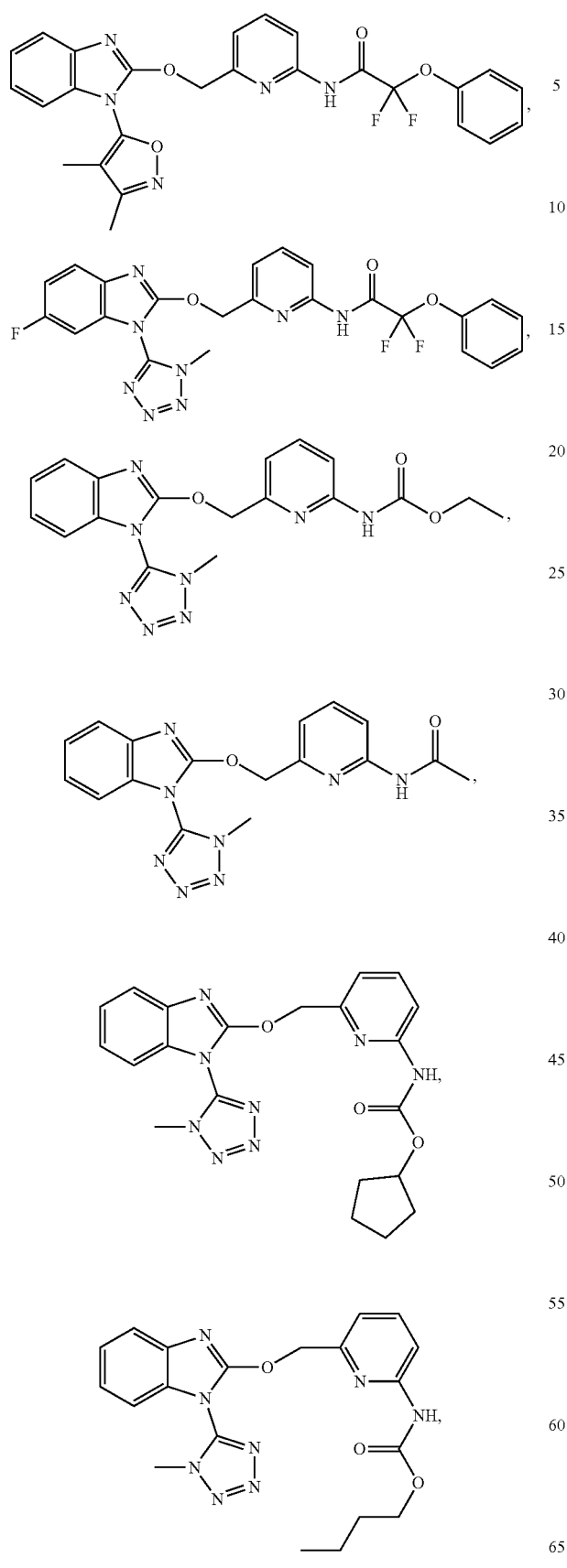
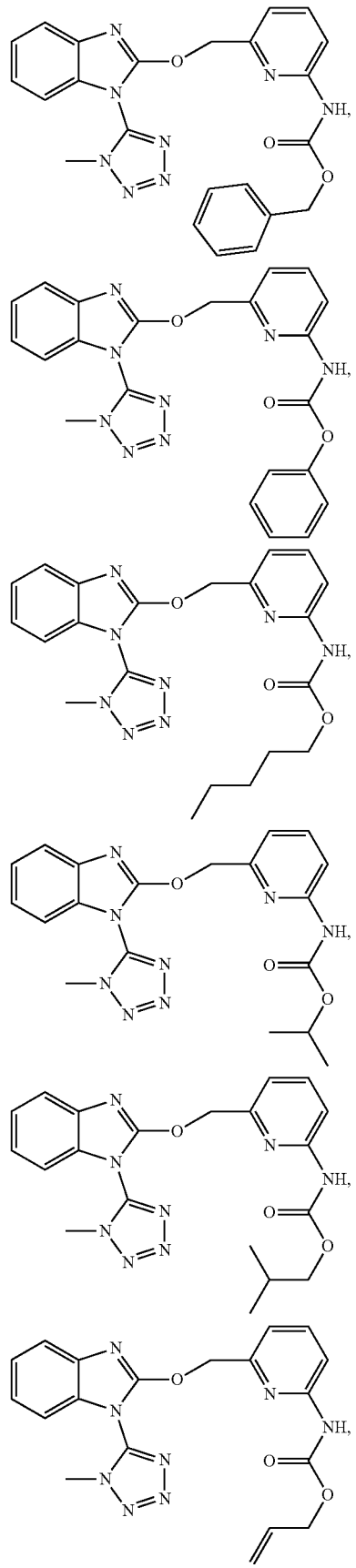

129
-continued
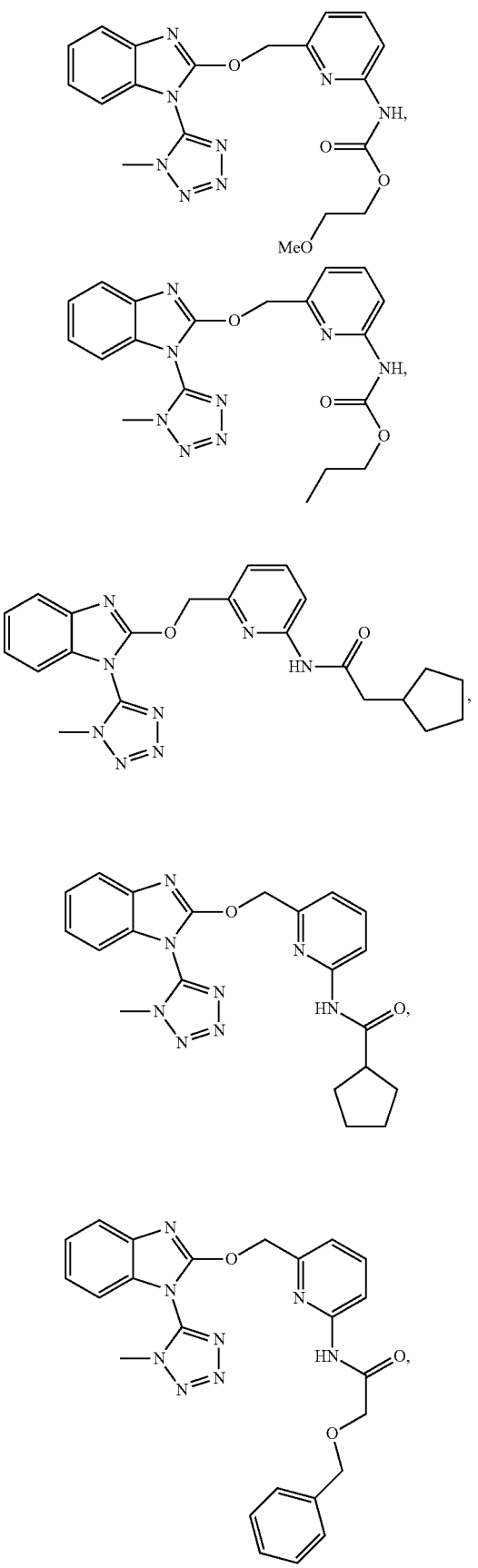
130
-continued
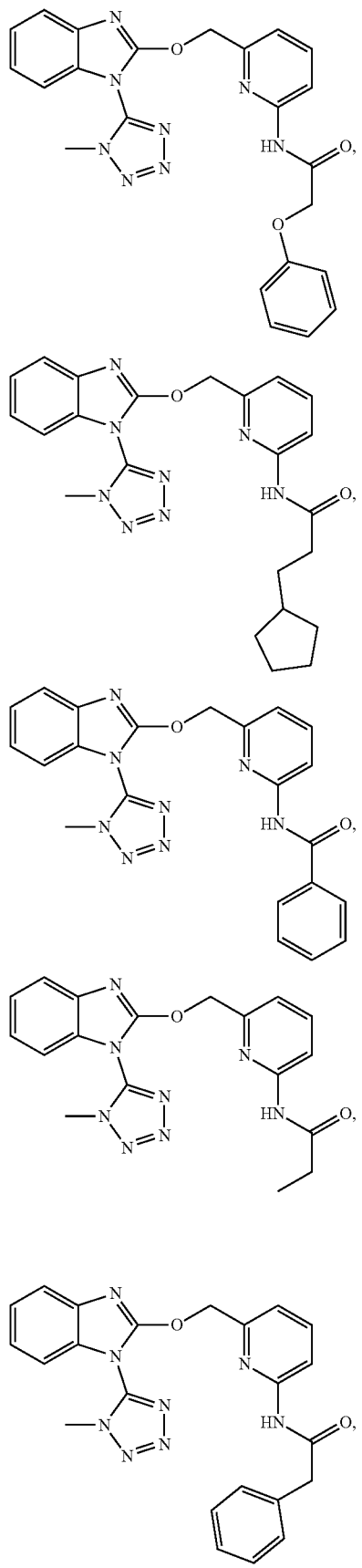

131
-continued
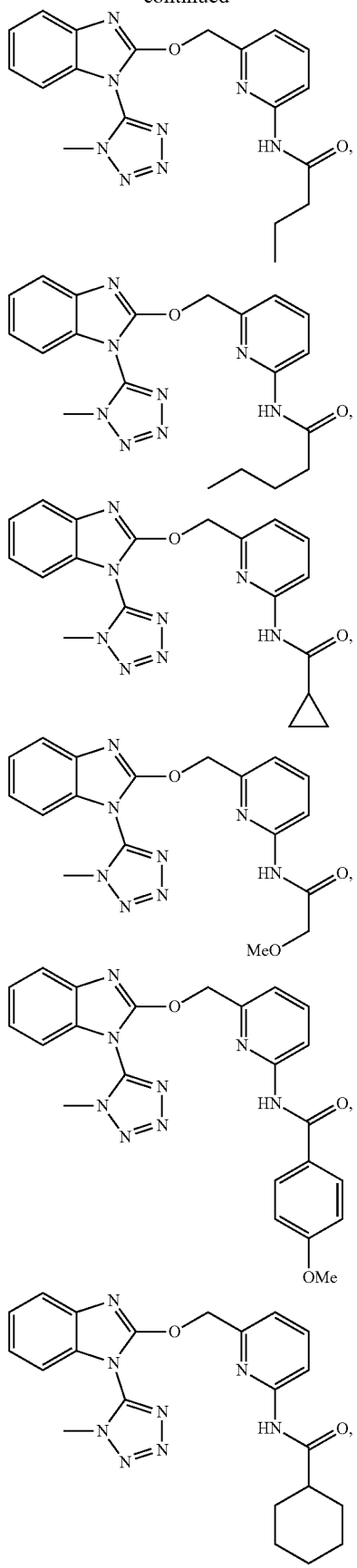
132
-continued
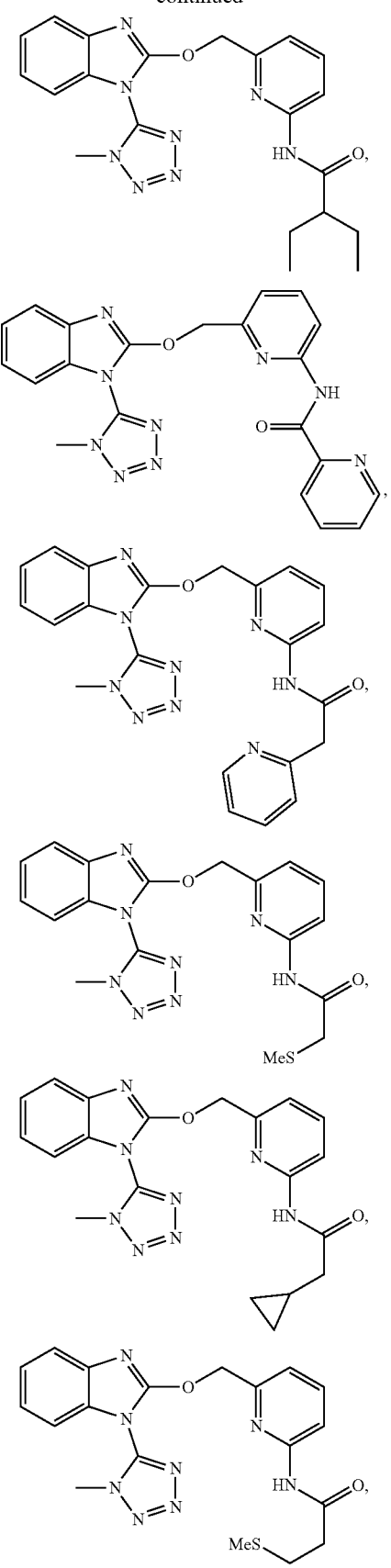

133
-continued
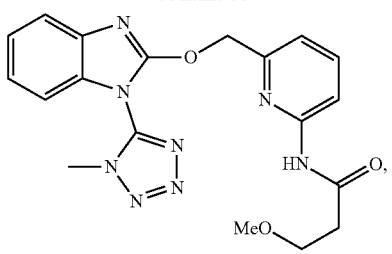
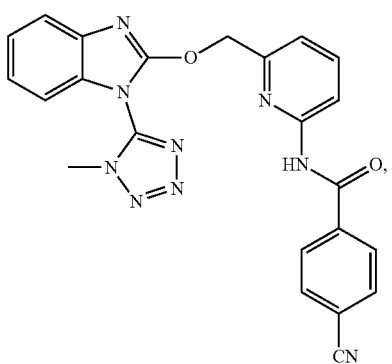
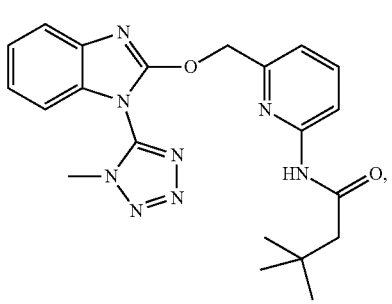
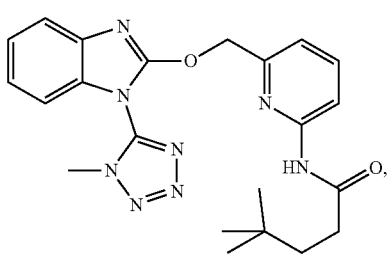
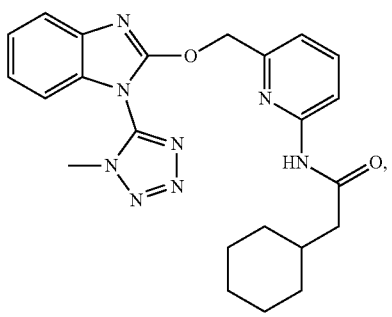
134
-continued
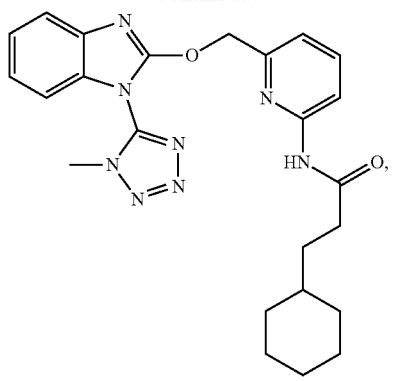
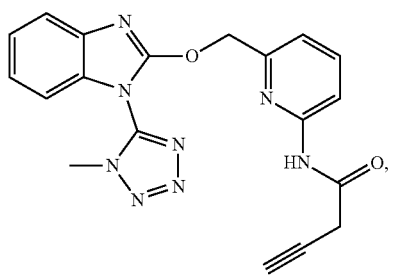
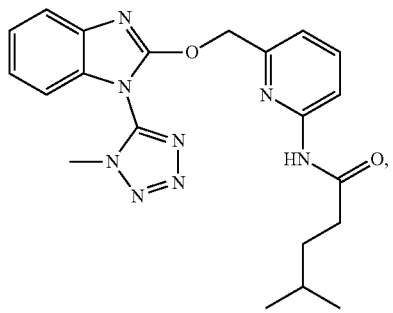
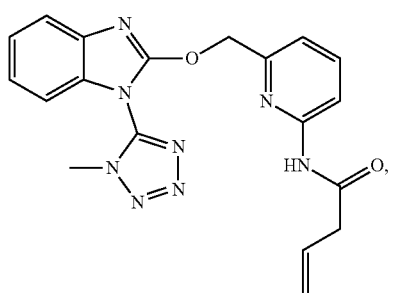
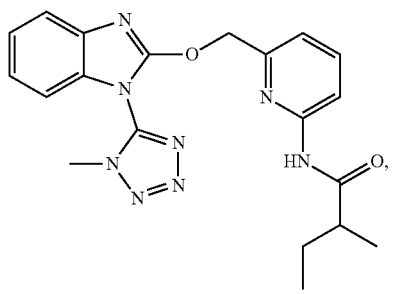

135
-continued
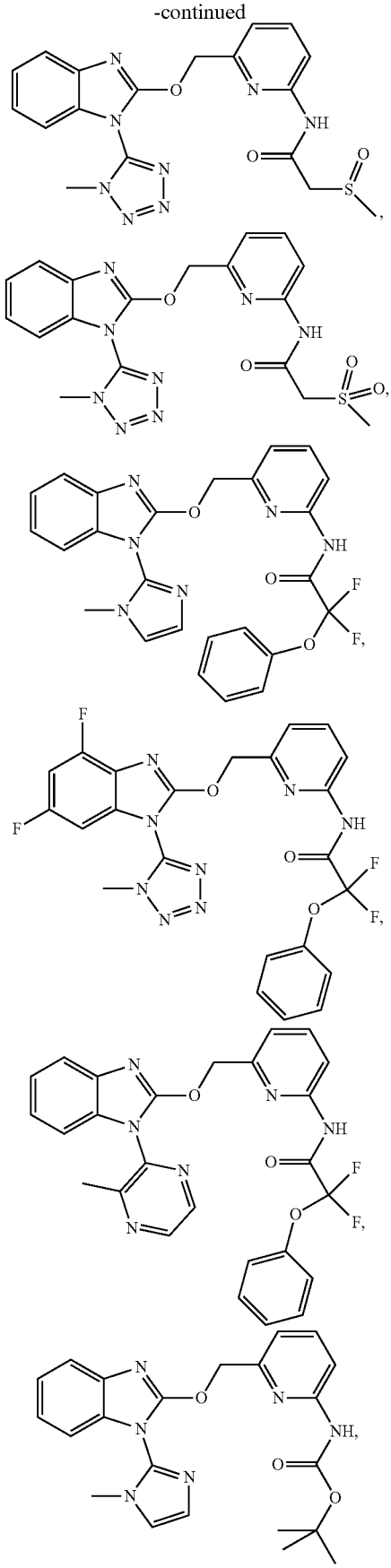
136
-continued
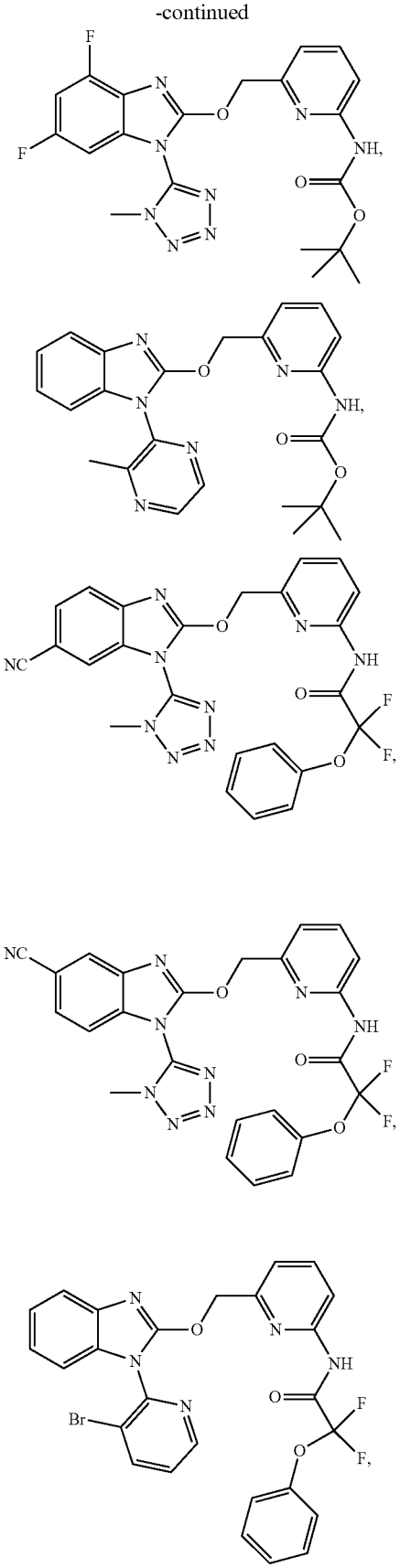

137
-continued
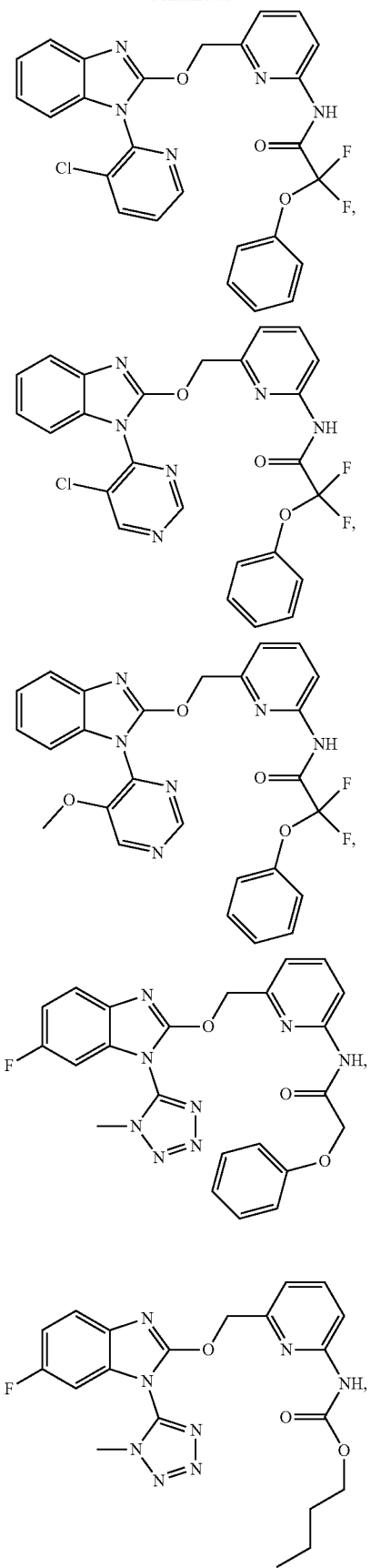
138
-continued
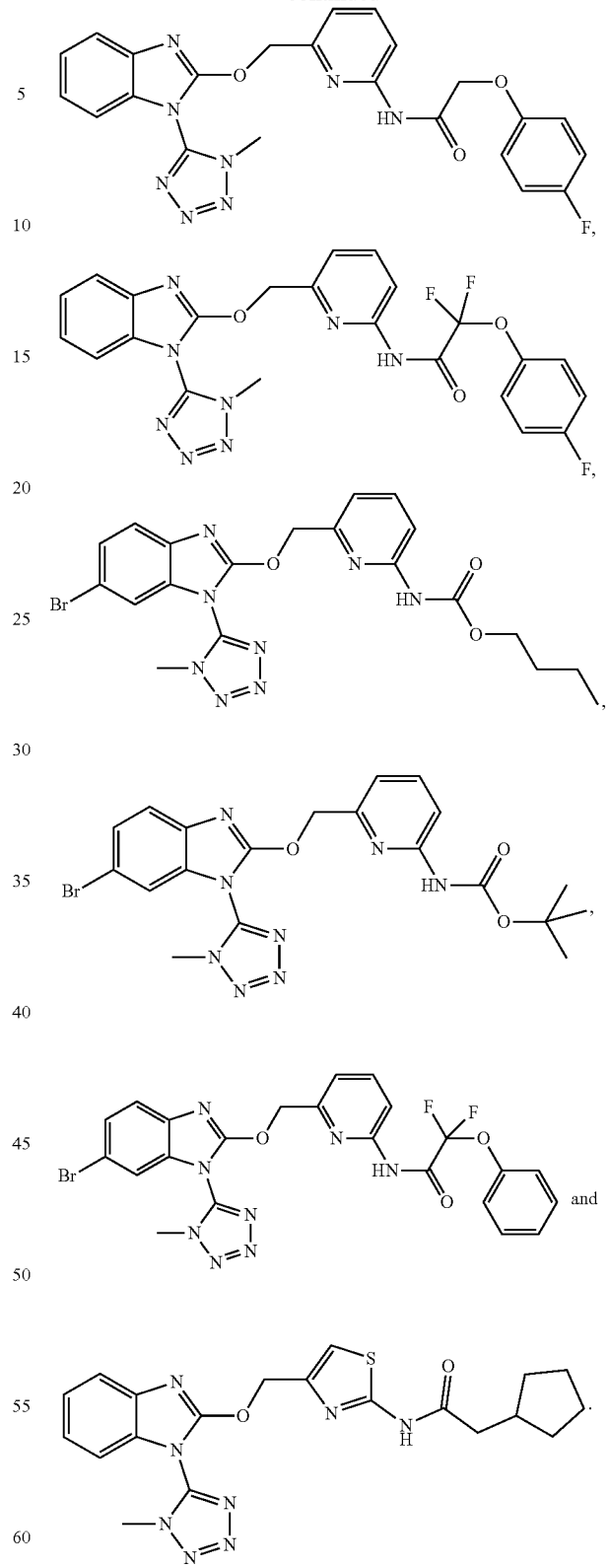
15. A compound of claim 1, wherein =A$^1$ is =O.
16. A compound of claim 1, wherein Ring D is substituted at a position adjacent to the point of connection of Ring D to the rest of the molecule with an R$^6$ group.

17. A compound of claim 16, wherein Ring D is

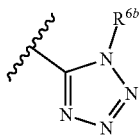

wherein $R^{6b}$ is independently selected from the group consisting of: substituted or unsubstituted $C_1$-$C_4$-alkyl, $C_3$-$C_4$-alkenyl and $C_3$-$C_4$-alkynyl.

18. A fungicidal composition comprising an effective and non-phytotoxic amount of an active compound of claim 1.

19. A method for controlling fungal diseases, the method comprising applying an agronomically effective and non-phytotoxic quantity of a compound of claim 1 to seeds of plants, to plants or to an area where it is intended that plants will grow.

20. A method for controlling oomycete diseases, the method comprising applying an agronomically effective and non-phytotoxic quantity of a compound of claim 1 to seeds of plants, to plants or to an area where it is intended that plants will grow.

21. A fungicidal composition comprising an effective and non-phytotoxic amount of an active compound of formula (I):

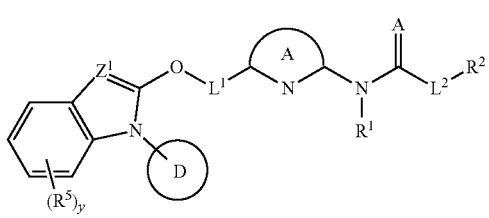

wherein Ring A is independently a 5- or 6-membered heteroaryl ring having a nitrogen in the position indicated, optionally further substituted with 1 to 3 $R^3$ groups;

Ring D is independently selected from the group consisting of 5- or 6-membered heteroaryl and phenyl, optionally further substituted with 1 to 5 $R^6$ groups;

y is an integer from 0 to 4;

$Z^1$ is independently selected from the group consisting of N and CH;

=$A^1$ is selected from the group consisting of =O and =S;

$L^1$- is -$C_1$-$C_3$-alkylene-;

-$L^2$- is absent or is independently selected from the group consisting of —O—, —S— and —$NR^9$—;

$R^1$, $R^9$ and $R^{10}$ are each independently at each occurrence selected from the group consisting of H and substituted or unsubstituted $C_1$-$C_4$-alkyl;

$R^2$ is independently selected from the group consisting of: substituted or unsubstituted $C_1$-$C_6$-alkyl, $C_2$-$C_6$-alkenyl, $C_2$-$C_6$-alkynyl, substituted or unsubstituted $C_3$-$C_6$-cycloalkyl, substituted or unsubstituted 3- to 6-membered heterocycloalkyl, substituted or unsubstituted 5- or 6-membered heteroaryl, substituted or unsubstituted phenyl, —$CR^7R^7L^3R^8$, and substituted or unsubstituted —$C_1$-$C_3$-alkylene-$R^{2a}$; wherein Rea is independently selected from the group consisting of substituted or unsubstituted $C_3$-$C_6$-cycloalkyl, substituted or unsubstituted 3- to 6-membered heterocycloalkyl, substituted or unsubstituted 5- or 6-membered heteroaryl and substituted or unsubstituted phenyl;

-$L^3$- is independently selected from the group consisting of —O—, —S— and —$NR^9$—;

$R^3$, $R^5$ and $R^6$ are each independently at each occurrence selected from the group consisting of: halo, nitro, cyano, $NR^{10}R^{11}$, $NR^{10}S(O)_2R^{10}$, $NR^{10}C(O)R^{10}$, $NR^{10}CONR^{10}R^{10}$, $NR^{10}CO_2R^{10}$, $OR^{10}$, $SR^{10}$, $S(O)R^{10}$, $S(O)_2R^{10}$, $S(O)_2NR^{10}R^{10}$, $CO_2R^{10}$, $C(O)R^{10}$, $CONR^{10}R^{10}$, substituted or unsubstituted $C_1$-$C_4$-alkyl, $C_2$-$C_4$-alkenyl, $C_2$-$C_4$-alkynyl, substituted or unsubstituted phenyl, substituted or unsubstituted $C_3$-$C_6$-cycloalkyl, substituted or unsubstituted 3- to 6-membered heterocycloalkyl, substituted or unsubstituted 5- or 6-membered heteroaryl and substituted or unsubstituted $C_1$-$C_4$-haloalkyl;

$R^7$ is independently at each occurrence selected from the group consisting of F, H and substituted or unsubstituted $C_1$-$C_4$-alkyl;

$R^8$ is independently selected from the group consisting of H, substituted or unsubstituted $C_1$-$C_4$-alkyl, $C_3$-$C_4$-alkenyl, $C_3$-$C_4$-alkynyl, $C_3$-$C_6$-cycloalkyl, substituted or unsubstituted 3- to 6-membered heterocycloalkyl, substituted or unsubstituted 5- or 6-membered heteroaryl, substituted or unsubstituted phenyl and substituted or unsubstituted —$C_1$-$C_3$-alkylene-$R^{8a}$; wherein $R^{8a}$ is independently selected from the group consisting of substituted or unsubstituted $C_3$-$C_6$-cycloalkyl, substituted or unsubstituted 3- to 6-membered heterocycloalkyl, substituted or unsubstituted 5- or 6-membered heteroaryl and substituted or unsubstituted phenyl;

$R^{11}$ is independently at each occurrence selected from the group consisting of H, substituted or unsubstituted $C_3$-$C_6$-cycloalkyl, substituted or unsubstituted $C_1$-$C_4$-alkyl, substituted or unsubstituted $C(O)$—$C_1$-$C_4$-alkyl and substituted or unsubstituted $S(O)_2$—$C_1$-$C_4$-alkyl;

wherein any substituted alkyl, alkylene, haloalkyl, cycloalkyl, heterocycloalkyl, aryl or heteroaryl group substituted, where chemically possible, by 1 to 5 substituents which are each independently selected at each occurrence from the group consisting of: oxo, =$NR^a$, =$NOR^a$, halo, nitro, cyano, $NR^aR^a$, $NR^aS(O)_2R^a$, $NR^aC(O)R^a$, $NR^aCONR^aR^a$, $NR^aCO_2R^a$, $OR^a$, $SR^a$, $S(O)R^a$, $S(O)_2R^a$, $S(O)_2NR^aR^a$, $CO_2R^a$ $C(O)R^a$, $CONR^aR^a$, unsubstituted $C_1$-$C_4$-alkyl, unsubstituted $C_2$-$C_4$-alkenyl, unsubstituted $C_2$-$C_4$-alkynyl and unsubstituted $C_1$-$C_4$-haloalkyl; wherein $R^a$ is independently at each occurrence selected from the group consisting of H, unsubstituted $C_1$-$C_4$ alkyl and unsubstituted $C_1$-$C_4$-haloalkyl;

or an agronomically acceptable salt or N-oxide thereof.

* * * * *